US012351625B2

(12) United States Patent
Leung et al.

(10) Patent No.: US 12,351,625 B2
(45) Date of Patent: Jul. 8, 2025

(54) THERAPEUTIC ANTIBODIES AGAINST OSTEOPONTIN

(71) Applicants: The Board of Trustees of the Leland Stanford Junior University, Stanford, CA (US); The United States Government as represented by the Department of Veterans Affairs, Washington, DC (US)

(72) Inventors: Lawrence L. K. Leung, Hillsborough, CA (US); Michael J. Morser, San Francisco, CA (US); Timothy Myles, Sunnyvale, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 822 days.

(21) Appl. No.: 17/633,797

(22) PCT Filed: Aug. 7, 2020

(86) PCT No.: PCT/US2020/045466
§ 371 (c)(1),
(2) Date: Feb. 8, 2022

(87) PCT Pub. No.: WO2021/030209
PCT Pub. Date: Feb. 18, 2021

(65) Prior Publication Data
US 2022/0324956 A1   Oct. 13, 2022

Related U.S. Application Data

(60) Provisional application No. 62/884,818, filed on Aug. 9, 2019.

(51) Int. Cl.
| A61K 39/395 | (2006.01) |
| A61K 31/397 | (2006.01) |
| A61K 31/4184 | (2006.01) |
| A61K 31/519 | (2006.01) |
| A61K 47/00 | (2006.01) |
| A61P 35/00 | (2006.01) |
| C07K 16/00 | (2006.01) |
| C07K 16/24 | (2006.01) |

(52) U.S. Cl.
CPC ............ *C07K 16/24* (2013.01); *A61K 31/397* (2013.01); *A61K 31/4184* (2013.01); *A61K 31/519* (2013.01); *A61K 47/00* (2013.01); *A61P 35/00* (2018.01)

(58) Field of Classification Search
None
See application file for complete search history.

(56) References Cited

U.S. PATENT DOCUMENTS

| 2005/0040570 | A1 | 3/2005 | Zhang |
| 2006/0002923 | A1 | 1/2006 | Uede et al. |
| 2012/0171699 | A1 | 7/2012 | Goodman et al. |
| 2017/0137509 | A1* | 5/2017 | Staffler .................... A61P 5/50 |
| 2018/0105598 | A1 | 4/2018 | Pfister et al. |

FOREIGN PATENT DOCUMENTS

| EP | 1375518 A1 | 1/2004 |
| EP | 2077325 A1 | 7/2009 |
| JP | 2009216567 | 9/2009 |
| WO | WO0171358 A1 | 9/2001 |
| WO | 2006043954 A1 | 4/2006 |
| WO | 2014/067642 A1 | 5/2014 |
| WO | 2015/200790 A2 | 12/2015 |
| WO | 2018/083237 A1 | 5/2018 |
| WO | 2018111852 A1 | 6/2018 |

OTHER PUBLICATIONS

Wanko, B et al. Antibody-mediated targeting of cleavage-specific OPN-T cell interactions. PLoS ONE. Apr. 5, 2019, 14(4):e0214938.
Shojaei et al., (2012) "Osteopontin induces growth of metastatic tumors in a preclinical model of non-small lung cancer", Journal Of Experimental & Clinical Cancer Research, Biomed Central Ltd, 31(26):1-12.

* cited by examiner

*Primary Examiner* — Meera Natarajan
(74) *Attorney, Agent, or Firm* — Jenny L. Buchbinder; Bozicevic, Field & Francis LLP

(57) ABSTRACT

Therapeutic antibodies specific for osteopontin and methods of using them for treating osteopontin-associated disorders are provided. In particular, antibodies, or antigen-binding fragments thereof, that inhibit thrombin-cleavage of osteopontin or block the activity of thrombin cleavage fragments of osteopontin are provided. Additionally, antibody conjugates and pharmaceutical compositions or formulations comprising the antibodies or antibody conjugates as well as kits including the antibodies, conjugates, or formulations are also provided.

19 Claims, 13 Drawing Sheets
Specification includes a Sequence Listing.

FIG. 7

Thrombin cleavage site

```
https://www.ebi.ac.uk
sp|P31097|OSTP_RABIT    DAATTVFTEWVPTVETYDGRGDSVAYRLKRSKSKMFHVSNAQYPGASEEDLSSHVDSEDL  60
sp|P10923|OSTP_MOUSE    STQADTFTPIVPTVDVPNGRGDSLAYGL-RSKSRSFQVSDEQYPDATDEDLTSHMKSGES  59
sp|P08721|OSTP_RAT      STQADVLTPIAPTVDVPPDGRGDSLAYGL-RSKSRSFPVSDEQYPDATDEDLTSRMKSQES  59
sp|P10451|OSTP_HUMAN    LPATEVFTPVVPTVDTYDGRGDSVVYGL-RSKSKKFRRPDIQYPDATDEDITSHMESEEL  59
tr|F6V2X3|F6V2X3_MACMU  LPATEVFTPVVPTVDTYDGRGDSVAYGL-RSKSKKFRRPDIQYPDATDEDITSHVESEEL  59
tr|A0A2K5WL52|A0A2K5WL52_MACFA LPATEVFTPVVPTVDIYDGRGDSVAYGL-RSKSKKFRRPDIQYPDATDEDITSHVESEEL  59
sp|P14287|OSTP_PIG      -TPATDVTPAVPTGDPNDGRGDSVVYGL-RSKSKKFRRSEAQQLDATEEDLTSHVESEET  58
                          .  : **  **  . * ******  ***  * ****   : * * ****:** *: *
```

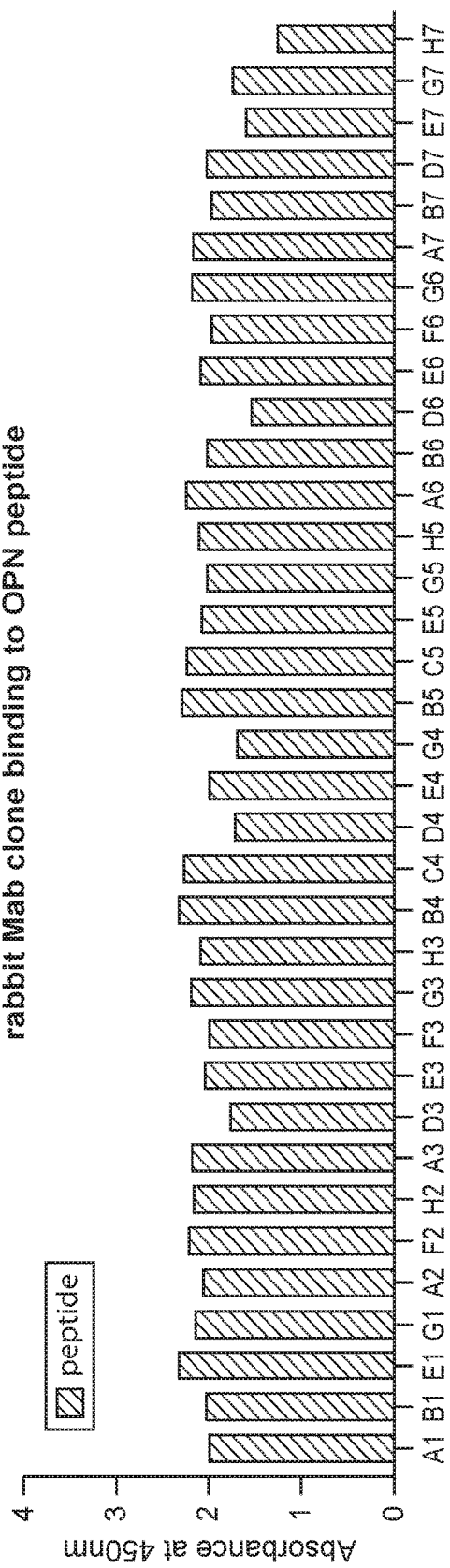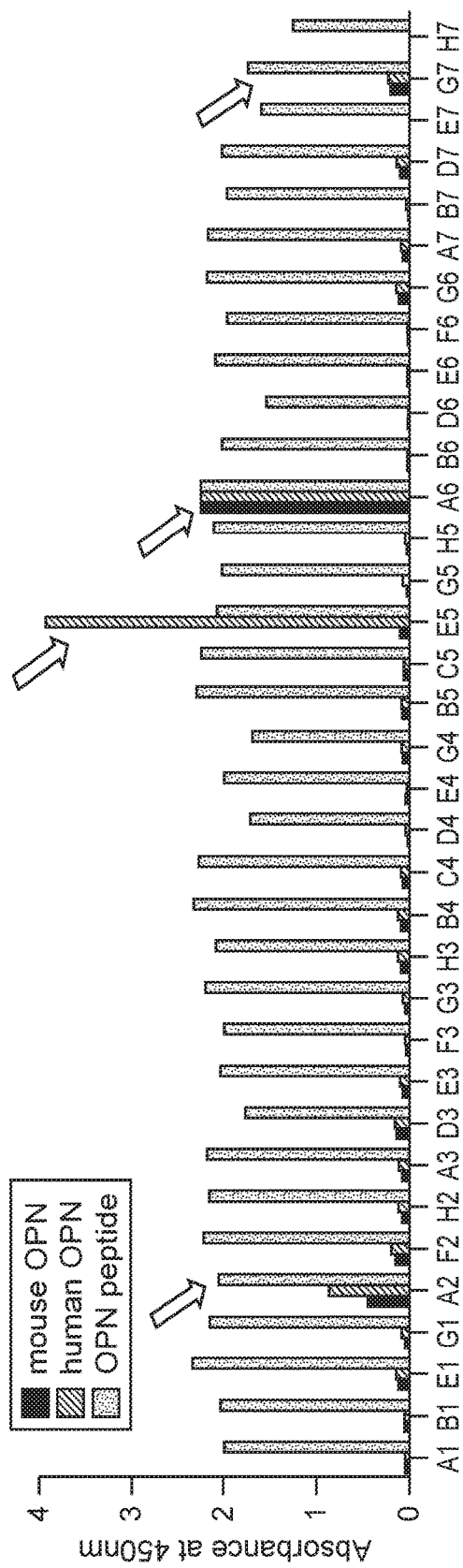

THERAPEUTIC ANTIBODIES AGAINST OSTEOPONTIN

BACKGROUND

Osteopontin (OPN) is a matricellular multifunctional protein with a highly conserved RGD domain that binds to a wide range of integrins. Thrombin cleavage at Arg153 in mouse (Arg168 in humans) generates OPN-Arg (OPN-R) and OPN-C-terminal fragment (OPN-CTF). OPN-R, which has SVVYGLR (SEQ ID NO:3) at its C-terminus, binds to a subset of integrins (α4β1 and α9β1) that full-length OPN does not bind to. The physiological role of the OPN-R fragment is thought to include a role as an immune modulator promoting cell adhesion, migration and survival (Kahles F. et. al. (2014) Mol. Metab. 3:384). The role of the OPN-CTF fragment is not as well studied but it has been shown to interact with dendritic cells promoting their chemotaxis in response to a chemokine (Shao Z. et. al. (2014) J. Biol. Chem. 289:27146). OPN-R has been implicated in inflammatory disorders such as rheumatoid arthritis (Song J J. et. al. (2011) J. Clin. Invest. 121:3517) but its role in cancers remains unknown (Castello L M. et. al. (2017) Mediators Inflamm. 2017: 4049098). Carboxypeptidase B2 (CPB2) or caboxypeptidase N (CPN) remove the C-terminal arginine from OPN-R, converting it to OPN-Leu (OPN-L), abrogating integrin binding to the SVVYGLR (SEQ ID NO:3) binding motif (Myles T. et al. (2003) J Biol Chem. 278(51):51059-51067, Shao Z. et. al. (2014) J. Biol. Chem. 289:27146). Elevated levels of OPN-R and OPN-L were found in synovial fluid samples from patients with rheumatoid arthritis but they were not as elevated in patients with osteoarthritis or psoriatic arthritis (Sharif S. et. al. (2009) Arthritis Rheum 60:2902). The role of OPN-CTF has also been demonstrated in a murine experimental autoimmune encephalitis (EAE) model that suggests that antibodies against the OPN-CTF have a protective effect (Clemente N. et. al. (2017) Front. Immunol. 8:321).

SUMMARY

Therapeutic antibodies specific for osteopontin and methods of using them for treating osteopontin-associated disorders are provided. In particular, antibodies that inhibit thrombin-cleavage of osteopontin or interactions of thrombin-cleavage fragments of osteopontin with integrins and/or other cellular receptors are useful for treating osteopontin-associated disorders such as inflammation, cardiac hypertrophy, myocardial fibrosis, and cancers over-expressing osteopontin, such as melanoma, glioblastoma, ovarian cancer, breast cancer, and lung cancer.

In one aspect, an isolated antibody or an antigen-binding fragment thereof is provided that specifically binds to osteopontin or a thrombin cleavage fragment thereof, wherein the antibody inhibits thrombin cleavage of osteopontin or integrin binding to a thrombin cleavage fragment of osteopontin. In certain embodiments, the antibody or antigen-binding fragment thereof specifically binds to an OPN-R fragment or an OPN-CTF fragment. In certain embodiments, the antibody or antigen-binding fragment thereof specifically binds to an epitope comprising Arg168 of osteopontin. In certain embodiments, the antibody or antigen-binding fragment thereof specifically binds to an osteopontin peptide comprising or consisting of a sequence selected from the group consisting of SEQ ID NOS:1-7, SEQ ID NOS:9-12, and SEQ ID NO:47.

In certain embodiments, the antibody or antigen-binding fragment thereof comprises a heavy chain complementarity-determining region 1 (CDR-H1) comprising the amino acid sequence of SEQ ID NO:29; a heavy chain complementarity-determining region 2 (CDR-H2) comprising the amino acid sequence of SEQ ID NO:30; a heavy chain complementarity-determining region 3 (CDR-H3) comprising the amino acid sequence of SEQ ID NO:31; a light chain complementarity-determining region 1 (CDR-L1) comprising the amino acid sequence of SEQ ID NO:32; a light chain complementarity-determining region 2 (CDR-L2) comprising the amino acid sequence of SEQ ID NO:33; and a light chain complementarity-determining region 3 (CDR-L3) comprising the amino acid sequence of SEQ ID NO:34. In some embodiments, the antibody or antigen-binding fragment thereof comprises a heavy chain comprising the amino acid sequence of SEQ ID NO:14 or SEQ ID NO:18, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:16 or SEQ ID NO:20, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the antibody or antigen-binding fragment thereof comprises a heavy chain complementarity-determining region 1 (CDR-H1) comprising the amino acid sequence of SEQ ID NO:35; a heavy chain complementarity-determining region 2 (CDR-H2) comprising the amino acid sequence of SEQ ID NO:36; a heavy chain complementarity-determining region 3 (CDR-H3) comprising the amino acid sequence of SEQ ID NO:37; a light chain complementarity-determining region 1 (CDR-L1) comprising the amino acid sequence of SEQ ID NO:38; a light chain complementarity-determining region 2 (CDR-L2) comprising the amino acid sequence of SEQ ID NO:39; and a light chain complementarity-determining region 3 (CDR-L3) comprising the amino acid sequence of SEQ ID NO:40. In some embodiments, the antibody or antigen-binding fragment thereof comprises a heavy chain comprising the amino acid sequence of SEQ ID NO:22, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:24, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the antibody or antigen-binding fragment thereof comprises a heavy chain complementarity-determining region 1 (CDR-H1) comprising the amino acid sequence of SEQ ID NO:41; a heavy chain complementarity-determining region 2 (CDR-H2) comprising the amino acid sequence of SEQ ID NO:42; a heavy chain complementarity-determining region 3 (CDR-H3) comprising the amino acid sequence of SEQ ID NO:43; a light chain complementarity-determining region 1 (CDR-L1) comprising the amino acid sequence of SEQ ID NO:44; a light chain complementarity-determining region 2 (CDR-L2) comprising the amino acid sequence of SEQ ID NO:45; and a light chain complementarity-determining region 3 (CDR-L3) comprising the amino acid sequence of SEQ ID NO:46. In some embodiments, the antibody or antigen-binding fragment thereof comprises a heavy chain comprising the amino acid sequence of SEQ ID NO:26, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:28, sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the antibody is a monoclonal antibody, a polyclonal antibody, a chimeric antibody, a humanized antibody, a nanobody, a bispecific antibody, a bispecific T cell engager antibody, a trispecific antibody, a Fab fragment, a Fab' fragment, a F(ab')$_2$ fragment, a F$_v$ fragment, or a scFv fragment.

In another aspect, a composition for treating an osteopontin-associated disorder is provided, the composition comprising an antibody or antigen-binding fragment thereof, described herein, that specifically binds to osteopontin or a thrombin cleavage fragment thereof, wherein the antibody or antigen-binding fragment thereof inhibits thrombin cleavage of osteopontin or integrin binding to the thrombin cleavage fragment of osteopontin. In some embodiments, the osteopontin-associated disorder is melanoma, glioblastoma, ovarian carcinoma, cardiac hypertrophy, myocardial fibrosis, or inflammation.

In certain embodiments, the composition further comprises a pharmaceutically acceptable excipient or carrier. In some embodiments, the pharmaceutically acceptable carrier is selected from the group consisting of a cream, emulsion, gel, liposome, nanoparticle, and an ointment.

In certain embodiments, the composition further comprises an anti-cancer therapeutic agent including, but not limited to, a chemotherapeutic agent, an immunotherapeutic agent, a biologic therapeutic agent, a pro-apoptotic agent, an angiogenesis inhibitor, a photoactive agent, a radiosensitizing agent, and a radioisotope, or a combination thereof.

In certain embodiments, the composition further comprises a B-Raf inhibitor, a MEK inhibitor, or a combination thereof. Exemplary B-Raf inhibitors include, without limitation, dabrafenib, vemurafenib, sorafenib, LGX818, GDC-0879, and PLX-4720. Exemplary MEK inhibitors include, without limitation, trametinib, cobimetinib, binimetinib, selumetinib, and PD-325901.

In another aspect, a method of treating an osteopontin-associated disorder is provided, the method comprising administering to a subject in need thereof a therapeutically effective amount of an antibody or an antigen-binding fragment thereof, described herein, that specifically binds to osteopontin at a thrombin cleavage site or to a thrombin cleavage fragment of osteopontin. In certain embodiments, the antibody specifically binds to an OPN-R fragment or an OPN-CTF fragment. In some embodiments, the antibody inhibits integrin binding to the OPN-R fragment. Preferably, the antibody does not interfere with thrombin procoagulant activity in the subject.

In certain embodiments, the osteopontin-associated disorder is a cancer that overexpresses osteopontin. For example, cancers overexpressing osteopontin include, without limitation, melanoma, glioblastoma, ovarian cancer, breast cancer, and lung cancer. In some embodiments, the method further comprises administering at least one additional anti-cancer therapeutic agent, including without limitation, a chemotherapeutic agent, an immunotherapeutic agent, a biologic therapeutic agent, a pro-apoptotic agent, an angiogenesis inhibitor, a photoactive agent, a radiosensitizing agent, and a radioisotope, or a combination thereof.

In certain embodiments, the method further comprises administering a B-Raf inhibitor. Exemplary B-Raf inhibitors include, without limitation, dabrafenib, vemurafenib, sorafenib, LGX818, GDC-0879, and PLX-4720.

In certain embodiments, the method further comprises administering a mitogen-activated protein kinase (MEK) inhibitor. Exemplary MEK inhibitors include, without limitation, trametinib, cobimetinib, binimetinib, selumetinib, and PD-325901.

In certain embodiments, the antibody or antigen-binding fragment thereof is administered according to a daily dosing regimen or intermittently. Multiple cycles of treatment may be administered to the subject for a time period sufficient to effect at least a partial tumor response or more preferably a complete tumor response. In some embodiments, the time period is at least 6 months, 7 months, 8 months, 9 months, 10 months, 11 months, 12 months, 1.5 years, 2 years or longer.

In another aspect, a method for inhibiting growth and/or proliferation of tumor cells in a subject is provided, the method comprising administering to the subject an effective amount of an antibody or antigen-binding fragment thereof, described herein, that specifically binds to osteopontin or a thrombin cleavage fragment thereof, wherein the antibody or antigen-binding fragment thereof inhibits thrombin cleavage of osteopontin or integrin binding to a thrombin cleavage fragment of osteopontin.

In another aspect, a conjugate is provided comprising an antibody or antigen-binding fragment thereof, described herein, and an agent selected from the group consisting of an anti-cancer therapeutic agent, a detectable label, and an imaging agent. Exemplary anti-cancer therapeutic agents include, without limitation, a cytotoxic agent, a drug, a toxin, a nuclease, a hormone, an immunomodulator, a pro-apoptotic agent, an anti-angiogenic agent, a boron compound, a photoactive agent, and a radioisotope.

In another aspect, a kit is provided, the kit comprising a composition comprising an antibody or an antigen-binding fragment thereof, described herein, and instructions for using the kit for treating an osteopontin-associated disorder. The kit may further comprise means for administering the composition to a subject.

In another aspect, a method of producing an antibody is provided, the method comprising eliciting an immune response in a subject against an immunogenic peptide comprising a sequence selected from the group consisting of SEQ ID NOS:5-7, SEQ ID NOS:9-12, and SEQ ID NO:47.

In another aspect, an isolated nucleic acid is provided comprising: a) a nucleotide sequence selected from the group consisting of SEQ ID NO:13, SEQ ID NO:17, SEQ ID NO:21, and SEQ ID NO:25; b) a nucleotide sequence encoding a heavy chain comprising an amino acid sequence selected from the group consisting of SEQ ID NO:14, SEQ ID NO:18, SEQ ID NO:22, and SEQ ID NO:26; c) a nucleotide sequence selected from the group consisting of SEQ ID NO:15, SEQ ID NO:19, SEQ ID NO:23, and SEQ ID NO:27; d) a nucleotide sequence encoding a light chain comprising an amino acid sequence selected from the group consisting of SEQ ID NO:16, SEQ ID NO:20, SEQ ID NO:24, and SEQ ID NO:28; e) a nucleotide sequence having 80-100% sequence identity to a nucleotide sequence of a)-d), including any percent identity within this range, such as 81, 82, 83, 84, 85, 86, 87, 88, 89, 90, 91, 92, 93, 94, 95, 96, 97, 98, 99% sequence identity; and f) complements of a)-e).

In another aspect, a recombinant nucleic acid comprising a promoter operably linked to a nucleic acid described herein is provided.

In another aspect, a vector system comprising one or more vectors encoding an antibody or antigen-binding fragment thereof, described herein, is provided.

In certain embodiments, the vector system comprises one or more vectors encoding an antibody or antigen-binding fragment thereof, wherein the antibody or antigen-binding fragment thereof comprises a heavy chain complementarity-determining region 1 (CDR-H1) comprising the amino acid sequence of SEQ ID NO:29; a heavy chain complementarity-determining region 2 (CDR-H2) comprising the amino acid sequence of SEQ ID NO:30; a heavy chain complementarity-determining region 3 (CDR-H3) comprising the amino acid sequence of SEQ ID NO:31; a light chain complementarity-determining region 1 (CDR-L1) comprising the amino acid sequence of SEQ ID NO:32; a light chain complementarity-determining region 2 (CDR-L2) comprising the amino acid sequence of SEQ ID NO:33; and a light chain complementarity-determining region 3 (CDR-L3) comprising the amino acid sequence of SEQ ID NO:34. In certain embodiments, the antibody or antigen-binding fragment thereof comprises a heavy chain comprising the amino acid sequence of SEQ ID NO:14 or SEQ ID NO:18, or a sequence having at least 80% identity to the amino acid sequence of SEQ ID NO:14 or SEQ ID NO:18; and a light chain comprising the amino acid sequence of SEQ ID NO:16 or SEQ ID NO:20, or a sequence having at least 80% identity to the amino acid sequence of SEQ ID NO:16 or SEQ ID NO:20.

In certain embodiments, the vector system comprises one or more vectors encoding an antibody or antigen-binding fragment thereof, wherein the antibody or antigen-binding fragment thereof comprises a heavy chain complementarity-determining region 1 (CDR-H1) comprising the amino acid sequence of SEQ ID NO:35; a heavy chain complementarity-determining region 2 (CDR-H2) comprising the amino acid sequence of SEQ ID NO:36; a heavy chain complementarity-determining region 3 (CDR-H3) comprising the amino acid sequence of SEQ ID NO:37; a light chain complementarity-determining region 1 (CDR-L1) comprising the amino acid sequence of SEQ ID NO:38; a light chain complementarity-determining region 2 (CDR-L2) comprising the amino acid sequence of SEQ ID NO:39; and a light chain complementarity-determining region 3 (CDR-L3) comprising the amino acid sequence of SEQ ID NO:40. In certain embodiments, the antibody or antigen-binding fragment thereof comprises a heavy chain comprising the amino acid sequence of SEQ ID NO:22, or a sequence having at least 80% identity to the amino acid sequence of SEQ ID NO:22; and a light chain comprising the amino acid sequence of SEQ ID NO:24 or a sequence having at least 80% identity to the amino acid sequence of SEQ ID NO:24.

In certain embodiments, the vector system comprises one or more vectors encoding an antibody or antigen-binding fragment thereof, wherein the antibody or antigen-binding fragment thereof comprises a heavy chain complementarity-determining region 1 (CDR-H1) comprising the amino acid sequence of SEQ ID NO:41; a heavy chain complementarity-determining region 2 (CDR-H2) comprising the amino acid sequence of SEQ ID NO:42; a heavy chain complementarity-determining region 3 (CDR-H3) comprising the amino acid sequence of SEQ ID NO:43; a light chain complementarity-determining region 1 (CDR-L1) comprising the amino acid sequence of SEQ ID NO:44; a light chain complementarity-determining region 2 (CDR-L2) comprising the amino acid sequence of SEQ ID NO:45; and a light chain complementarity-determining region 3 (CDR-L3) comprising the amino acid sequence of SEQ ID NO:46. In certain embodiments, the antibody or antigen-binding fragment thereof comprises a heavy chain comprising the amino acid sequence of SEQ ID NO:26, or a sequence having at least 80% identity to the amino acid sequence of SEQ ID NO:26; and a light chain comprising the amino acid sequence of SEQ ID NO:28, or a sequence having at least 80% identity to the amino acid sequence of SEQ ID NO:28.

In certain embodiments, a vector system described herein encodes an antibody or antigen-binding fragment thereof that is chimerized or humanized.

In another aspect, a host cell comprising a vector system described herein is provided.

In another aspect, a method of producing an antibody or antigen-binding fragment thereof is provided, the method comprising: a) culturing a host cell comprising a vector system described herein under conditions suitable for production of the antibody or antigen-binding fragment thereof; and b) isolating the antibody or antigen-binding fragment thereof from the host cell.

In another aspect, a hybridoma producing an antibody described herein is provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 7 shows the screening strategy to identify monoclonal antibodies (Mabs) that bind to full-length osteopontin (OPN-FL) and block its cleavage by thrombin. OPN protein sequences (in single letter amino acid code) from around the thrombin cleavage site are shown from the following species: rabbit, rat, mouse, human, rhesus macaque, cynomolgus, and pig are shown. The colors of the amino acids represent their chemical properties. The black box encloses the thrombin cleavage site. The asterisks mark conserved amino acids. The peptide antigen, YGLRSKS (SEQ ID NO:11, amino acid in bold is cleaved by thrombin), covalently bound to keyhole limpet hemocyanin, was used to raise antibodies in rabbits in order to develop rabbit monoclonal antibodies. Rabbits were chosen because their OPN sequence around the thrombin cleavage site is different from mouse or human sequence: YRLKRSKS (SEQ ID NO:47, amino acid in bold is cleaved by thrombin). Cells producing antibodies that bound to the peptide antigen had their heavy and light chain cDNA cloned and inserted into expression vectors that express rabbit IgG. Those expression vectors were then transfected into HEK293F cells and the medium assayed. Antibody screening was then used to identify clones producing antibodies reacting with mouse, rat and human osteopontin. Some selected clones (see FIG. 9 below) were then grown on a larger scale, the medium harvested and the IgG purified.

FIG. 8 shows results of screening rabbit monoclonal clones in a direct ELISA against the OPN antigen peptide. 35 positives (shown) were identified. For the assay to identify clones producing anti-OPN IgG, 96 well plates were coated with 2 ug/mL avidin overnight before addition of the OPN antigen peptide labeled with biotin for 30 minutes. Then supernatants from the clones were diluted 1:50 before detection with an anti-Rabbit IgG Fc labeled with horse radish peroxidase (HRP) diluted $10^3$ times. Substrate for HRP was added and color was measured. To determine the concentration of the IgG in the clone supernatants, 96 well plates were coated with 2 ug/mL anti-rabbit IgG overnight. Then supernatants from the clones were diluted 1:50 before detection with an anti-Rabbit IgG Fc labeled with horse radish peroxidase (HRP) diluted $10^3$ times. Substrate for HRP was added and color was measured. The concentration of IgG in the clone supernatants was calculated from a standard dilution curve of rabbit IgG.

FIG. 9 shows results of screening rabbit monoclonal antibodies in a direct ELISA against the antigen peptide (medium gray, data from FIG. 8), mouse OPN-FL (light gray) and human OPN-FL (dark gray). Clones were identified that bound human OPN-FL or mouse OPN-FL. Four clones were selected for further investigation based on their binding to mouse or human OPN-FL (arrows).

DETAILED DESCRIPTION OF EMBODIMENTS

Figure 1:
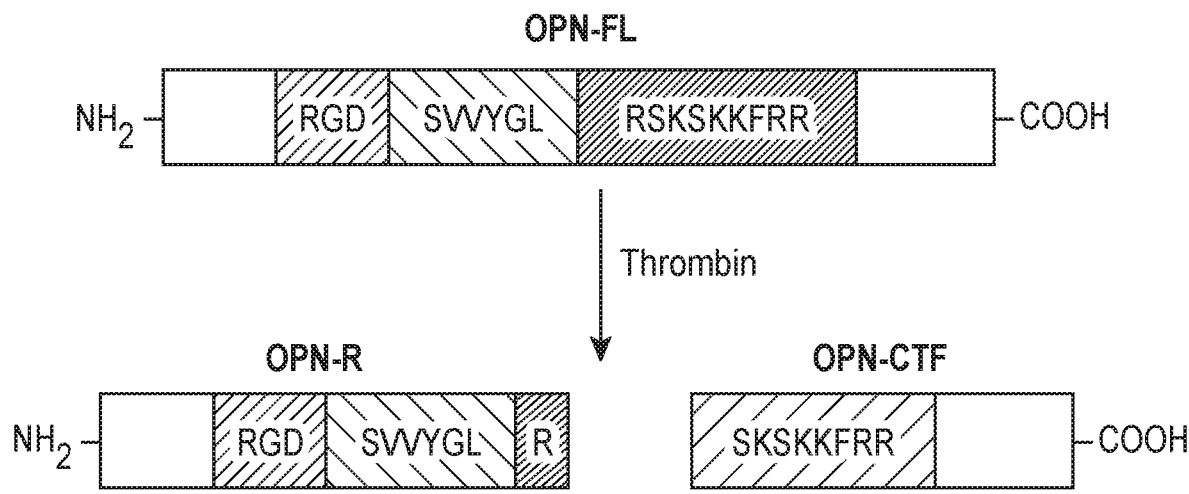
FIG. 1 shows a schematic representation of thrombin and CPB2-mediated OPN cleavages.

Therapeutic antibodies specific for osteopontin and methods of using them for treating osteopontin-associated disorders are provided. In particular, antibodies, or antigen-binding fragments thereof, that inhibit thrombin-cleavage of osteopontin or block the activity of thrombin cleavage fragments of osteopontin are provided. Additionally, antibody conjugates and pharmaceutical compositions or formulations comprising the antibodies or antibody conjugates as well as kits including the antibodies, conjugates, or formulations are also provided.

Before the therapeutic antibodies and methods of using them in treating osteopontin-associated disorders are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "an antibody" includes a plurality of such antibodies and reference to "the cancerous cell" includes reference to one or more cancerous cells and equivalents thereof, such as cancer cells, tumor cells, neoplastic cells, and malignant cells, known to those skilled in the art, and so forth.

The term "antibody" encompasses monoclonal antibodies, polyclonal antibodies, as well as hybrid antibodies, altered antibodies, chimeric antibodies, and humanized antibodies. The term antibody includes: hybrid (chimeric) antibody molecules (see, for example, Winter et al. (1991) Nature 349:293-299; and U.S. Pat. No. 4,816,567); bispecific antibodies, bispecific T cell engager antibodies (BiTE), trispecific antibodies, and other multispecific antibodies (see, e.g., Fan et al. (2015) J. Hematol. Oncol. 8:130, Krishnamurthy et al. (2018) Pharmacol Ther. 185:122-134), F(ab')$_2$ and F(ab) fragments; F$_v$ molecules (noncovalent heterodimers, see, for example, Inbar et al. (1972) Proc Natl Acad Sci USA 69:2659-2662; and Ehrlich et al. (1980) Biochem 19:4091-4096); single-chain F$_v$ molecules (scFv) (see, e.g., Huston et al. (1988) Proc Natl Acad Sci USA 85:5879-5883); nanobodies or single-domain antibodies (sdAb) (see, e.g., Wang et al. (2016) Int J Nanomedicine 11:3287-3303, Vincke et al. (2012) Methods Mol Biol 911: 15-26; dimeric and trimeric antibody fragment constructs; minibodies (see, e.g., Pack et al. (1992) Biochem 31:1579-1584; Cumber et al. (1992) J Immunology 149B:120-126); humanized antibody molecules (see, e.g., Riechmann et al. (1988) Nature 332:323-327; Verhoeyan et al. (1988) Science 239:1534-1536; and U.K. Patent Publication No. GB 2,276, 169, published 21 Sep. 1994); and, any functional fragments obtained from such molecules, wherein such fragments retain specific antigen-binding properties of the parent antibody molecule.

The phrase "specifically (or selectively) binds" with reference to binding of an antibody to an antigen (e.g., osteopontin or thrombin cleavage fragment thereof) refers to a binding reaction that is determinative of the presence of the antigen in a heterogeneous population of proteins and other biologics. Thus, under designated immunoassay conditions, the specified antibodies bind to a particular antigen at least two times over the background and do not substantially bind in a significant amount to other antigens present in the sample. Specific binding to an antigen under such conditions may require an antibody that is selected for its specificity for a particular antigen. For example, antibodies raised to an antigen from specific species such as rat, mouse, or human can be selected to obtain only those antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "conjugated" refers to the joining by covalent or noncovalent means of two compounds or agents.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer) as well as those in which prevention is desired (e.g., those with increased susceptibility to cancer, those suspected of having cancer, those with a risk of recurrence, etc.).

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

An "osteopontin-associated disorder" includes any disease or disorder associated with elevated levels of osteopontin or thrombin cleavage fragments thereof, including, without limitation, inflammation, cardiac hypertrophy, myocardial fibrosis, and cancers over-expressing osteopontin, such as melanoma, glioblastoma, ovarian cancer, breast cancer, and lung cancer.

The terms "tumor," "cancer" and "neoplasia" are used interchangeably and refer to a cell or population of cells in a mammal, whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma, and include cancers such as, but are not limited to, head and neck cancer, skin cancer, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

In particular, the term "melanoma" includes, any type of melanoma at any stage, including metastatic melanoma. For example, the term "melanoma" includes, without limitation, lentigo maligna, lentigo maligna melanoma, superficial spreading melanoma, acral lentiginous melanoma, mucosal melanoma, nodular melanoma, polypoid melanoma, and desmoplastic melanoma. Melanomas may contain changes (mutations) in their genomic DNA sequence that mean that the proteins encoded by a melanoma cell differ from those elsewhere in the patient's body. As an example, the protein, B-RAF, which is involved in signaling growth to the cell, can have mutations. Thus, the term also includes B-RAF-mutated melanoma, including without limitation, melanoma comprising a V600E mutation or a V600K mutation.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of an antibody, or antigen-binding fragment thereof, that specifically binds to osteopontin or a thrombin cleavage fragment thereof is intended an amount that, when administered as described herein, brings about a positive therapeutic response, such as anti-tumor activity or anti-inflammatory activity. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

The terms "polypeptide," "peptide" and "protein" are used interchangeably to refer to a polymer of amino acid residues. The terms also apply to amino acid polymers in which one or more amino acids are chemical analogues or modified derivatives of corresponding naturally-occurring amino acids.

"Substantially purified" generally refers to isolation of a substance (e.g., antibody, conjugate, compound, drug, nucleic acid, polynucleotide, protein, polypeptide, or peptide) such that the substance comprises the majority of the sample in which it resides and be defined as a percentage of the total sample. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

As used herein, the terms "detectable label", "detection agent", "imaging agent", "diagnostic agent", and "detectable moiety" are used interchangeably and refer to a molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of detectable labels which may be used in the practice of the invention include isotopic labels, including radioactive and non-radioactive isotopes, such as, $^3$H, $^2$H, $^{120}$I, $^{123}$I, $^{124}$I, $^{125}$I, $^{131}$I, $^{35}$S, $^{11}$C, $^{13}$C, $^{14}$C, $^{32}$P, $^{15}$N, $^{13}$N, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94m}$Tc, $^{99m}$Tc, $^{154}$Gd, $^{155}$Gd, $^{156}$Gd, $^{157}$Gd, $^{158}$Gd, $^{15}$O, $^{186}$Re, $^{188}$Re, $^{51}$M, $^{52m}$Mn, $^{55}$Co, $^{72}$As, $^{75}$Br, $^{76}$Br, $^{82m}$Rb, and $^{83}$Sr. In particular, detectable labels may comprise positron-emitting radionuclides suitable for PET imaging such as, but not limited to, $^{64}$Cu, $^{89}$Zr, $^{68}$Ga, $^{177}$Lu, $^{82}$Rb, $^{11}$C, $^{13}$N, $^{15}$O, and $^{18}$F; or gamma-emitting radionuclides suitable for single photon emission computed tomography (SPECT) imaging such as, but not limited to, $^{67}$Ga, $^{99m}$Tc, $^{123}$I, and $^{131}$I. Detectable labels may also include non-radioactive, paramagnetic metal ions suitable for MRI imaging such as, but not limited to, $Mn^{2+}$, $Fe^{3+}$, $Fe^{2+}$, $Gd^{3+}$, $Ti^{2+}$, $Cr^{3+}$, $Co^{2+}$, $Ni^{2+}$, and $Cu^{2+}$. Detectable labels may also include fluorophores including without limitation, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2',4',5',7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, Renilla luciferase, and aequorin. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. The terms also include contrast agents such as ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate). The detectable label or imaging agent may be attached indirectly or directly to an antibody, wherein the label or contrast agent facilitates the use of the antibody in imaging.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence. In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a donor polynucleotide, plasmid, or viral vector construct. In addition to the components of the expression cassette, the construct may also include, one or more selectable markers, a signal which allows the construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be apparent to one of ordinary skill in the art that various changes and modifications can be made without departing from the spirit or scope of the invention.

Anti-Osteopontin Antibodies

Anti-osteopontin antibodies are provided that specifically bind to one or more epitopes of osteopontin. In some embodiments, the anti-osteopontin antibodies specifically bind at a thrombin cleavage site and inhibit thrombin cleavage of osteopontin and/or specifically bind to a thrombin cleavage fragment of osteopontin (e.g., OPN-R fragment or an OPN-CTF fragment) and reduce biological activity of the thrombin cleavage fragment. In certain embodiments, the anti-osteopontin antibodies specifically bind to an epitope comprising Arg168 of osteopontin. The foregoing numbering is relative to the reference amino acid sequence of human osteopontin (SEQ ID NO:8), and it is to be understood that the corresponding positions in osteopontin proteins obtained from other species are also intended to be encompassed by the present disclosure.

The term "anti-osteopontin antibody" as used herein encompasses full-length antibodies as well as antigen-binding fragments thereof that include the antigen-binding region of an antibody, e.g., a molecule that includes the CDRs of an anti-osteopontin antibody such as a Fab, F(ab')$_2$, or F$_v$ fragment, a single-chain variable fragment (scFv), or any other type of antibody fragment of interest fragment (see definition of the term "antibody" above). Anti-osteopontin antibodies that may be used in the practice of the subject methods include, without limitation, monoclonal antibodies, polyclonal antibodies, hybrid antibodies, altered antibodies, chimeric antibodies and humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911: 15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276, 169, published 21 Sep. 1994); and, any functional fragments obtained from such molecules, wherein such fragments retain specific-binding properties of the parent antibody molecule.

In certain embodiments, an anti-osteopontin antibody or antigen-binding fragment thereof specifically binds to an osteopontin peptide comprising or consisting of a sequence selected from the group consisting of SEQ ID NOS:1-7, SEQ ID NOS:9-12, and SEQ ID NO:47.

In certain embodiments, an anti-osteopontin antibody or antigen-binding fragment thereof comprises a heavy chain complementarity-determining region 1 (CDR-H1) comprising the amino acid sequence of SEQ ID NO:29; a heavy chain complementarity-determining region 2 (CDR-H2) comprising the amino acid sequence of SEQ ID NO:30; a heavy chain complementarity-determining region 3 (CDR-H3) comprising the amino acid sequence of SEQ ID NO:31; a light chain complementarity-determining region 1 (CDR-L1) comprising the amino acid sequence of SEQ ID NO:32; a light chain complementarity-determining region 2 (CDR-L2) comprising the amino acid sequence of SEQ ID NO:33; and a light chain complementarity-determining region 3 (CDR-L3) comprising the amino acid sequence of SEQ ID NO:34. In some embodiments, the antibody or antigen-binding fragment thereof comprises a heavy chain comprising the amino acid sequence of SEQ ID NO:14 or SEQ ID NO:18, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:16 or SEQ ID NO:20, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, an anti-osteopontin antibody or antigen-binding fragment thereof comprises a heavy chain complementarity-determining region 1 (CDR-H1) comprising the amino acid sequence of SEQ ID NO:35; a heavy chain complementarity-determining region 2 (CDR-H2) comprising the amino acid sequence of SEQ ID NO:36; a heavy chain complementarity-determining region 3 (CDR-H3) comprising the amino acid sequence of SEQ ID NO:37; a light chain complementarity-determining region 1 (CDR-L1) comprising the amino acid sequence of SEQ ID NO:38; a light chain complementarity-determining region 2 (CDR-L2) comprising the amino acid sequence of SEQ ID NO:39; and a light chain complementarity-determining region 3 (CDR-L3) comprising the amino acid sequence of SEQ ID NO:40. In some embodiments, the antibody or antigen-binding fragment thereof comprises a heavy chain comprising the amino acid sequence of SEQ ID NO:22, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:24, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, an anti-osteopontin antibody or antigen-binding fragment thereof comprises a heavy chain complementarity-determining region 1 (CDR-H1) comprising the amino acid sequence of SEQ ID NO:41; a heavy chain complementarity-determining region 2 (CDR-H2) comprising the amino acid sequence of SEQ ID NO:42; a heavy chain complementarity-determining region 3 (CDR-H3) comprising the amino acid sequence of SEQ ID NO:43; a light chain complementarity-determining region 1 (CDR-L1) comprising the amino acid sequence of SEQ ID NO:44; a light chain complementarity-determining region 2 (CDR-L2) comprising the amino acid sequence of SEQ ID NO:45; and a light chain complementarity-determining region 3 (CDR-L3) comprising the amino acid sequence of SEQ ID NO:46. In some embodiments, the antibody or antigen-binding fragment thereof comprises a heavy chain comprising the amino acid sequence of SEQ ID NO:26, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:28, sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

Antibodies that specifically bind to osteopontin at a thrombin cleavage site or to a thrombin cleavage fragment of osteopontin (e.g., OPN-R fragment or an OPN-CTF fragment) can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). For example, an antigen comprising a peptide fragment of osteopontin including an osteopontin thrombin cleavage site or a thrombin cleavage fragment of osteopontin (e.g., OPN-R fragment or an OPN-CTF fragment) can be used to elicit an immune response in a mammal, such as a mouse, rat, rabbit, guinea pig, monkey, or human, to produce polyclonal antibodies. Exemplary peptides that can be used to elicit an immune response to produce anti-osteopontin antibodies include, without limitation, osteopontin peptides comprising or consisting of a sequence selected from the group consisting of SEQ ID NOS:1-7, SEQ ID NOS:9-12, and SEQ ID NO:47 (see also Examples). If desired, an antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface-active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and Corynebacterium parvum are especially useful.

Monoclonal antibodies which specifically bind to an osteopontin antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 31 42, 1985; Cote et al., Proc. Natl. Acad. Sci. 80, 2026-30, 1983; Cole et al., Mol. Cell Biol. 62, 109-20, 1984).

In addition, techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, Proc. Natl. Acad. Sci. 88, 11120-23, 1991). Single-chain antibodies also can be constructed using a DNA amplification method, such as PCR, using hybridoma cDNA as a template (Thirion et al., Eur. J. Cancer Prey. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J Cancer 61, 497-501, 1995; Nicholls et al., J. Immunol. Meth. 165, 81-91, 1993).

Antibodies which specifically bind to an osteopontin antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

In some embodiments, anti-osteopontin antibodies from B lymphocytes are obtained from blood donors and cloned. Nucleic acids encoding antibody light and heavy chains or fragments thereof containing variable domain complementarity-determining regions (e.g., Fab) can be amplified by PCR and cloned into vectors. ScFv antibodies can be generated by cloning into a vector a construct that connects the light and heavy chains via a linker in one open reading frame. The blood donor can be of any species. In some embodiments, human blood donors are used for generation of human antibodies. In other embodiments, camelid blood donors are used for generation of camelid antibodies. Camelid antibodies may be derived, for example, from Dromedary camels, bactrian camels, llamas and alpacas. Such camelids produce a unique type of antibody that lacks a light chain. Heavy-chain antibodies (HCAbs) or variable domain fragments thereof (e.g., single-domain antibodies or nanobodies) can also be used in the subject methods (see, e.g., Vincke et al. (2012) Methods Mol. Biol. 911:15-26, Krah et al. (2016) Immunopharmacol. Immunotoxicol. 38(1):21-8; herein incorporated by reference).

Antibodies can be purified by methods well known in the art. For example, antibodies can be affinity purified by passage over a column to which the relevant antigen is bound. The bound antibodies can then be eluted from the column using a buffer with a high salt concentration.

Chimeric and Humanized Antibodies

Suitable anti-osteopontin antibodies include fully human, humanized or chimeric versions of such antibodies. For example, humanized antibodies are useful for in vivo applications in humans due to their low antigenicity. Similarly, caninized, felinized, etc. antibodies are useful for applications in dogs, cats, and other species respectively. Antibodies of interest include humanized antibodies, or caninized, felinized, equinized, bovinized, porcinized, etc., antibodies, and variants thereof.

Chimeric monoclonal antibodies, in which the variable Ig domains of a non-human (e.g., mouse) monoclonal antibody are fused to human constant Ig domains, can be generated using standard procedures known in the art (See Morrison et al., Proc. Natl. Acad. Sci. USA 81, 6841-6855 (1984); and, Boulianne et al, Nature 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"); (2) transplanting the entire non-human variable domains, but "cloaking" them with a human-like surface by replacement of surface residues (a process referred to in the art as "veneering"); or (3) substituting human amino acids at positions determined to be unlikely to adversely effect either antigen binding or protein folding, but likely to reduce immunogenicity in a human environment (e.g., HUMAN ENGINEERING). In the present disclosure, humanized antibodies may include "humanized," "veneered," and/or "HUMAN ENGINEERED" antibodies. These methods are disclosed in, e.g., Jones et al., Nature 321:522 525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31:169-217 (1994); Studnicka et al. U.S. Pat. No. 5,766,886; Studnicka et al., (Protein Engineering 7: 805-814, 1994; Co et al., J. Immunol. 152, 2968-2976 (1994); Riechmann, et al., Nature 332:323-27 (1988); and Kettleborough et al., Protein Eng. 4:773-783 (1991) each of which is incorporated herein by reference.

CDR grafting involves introducing one or more of the six CDRs from the mouse heavy and light chain variable Ig domains into the appropriate four framework regions of human variable Ig domains. This technique (Riechmann, et al., Nature 332:323-27 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co et al., J. Immunol. 152, 2968-2976 (1994)).

Antibody Fragments

Anti-osteopontin antibodies may be in the form of an antibody fragment. Antibody fragments comprise a portion of an intact full-length antibody and can include an antigen binding or variable region of the intact antibody. Examples of antibody fragments include Fab; Fab'; F(ab')$_2$; Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See, e.g., Holliger & Hudson (Nat. Biotech. 23:1126-36 (2005)).

Papain digestion of antibodies produces two identical antigen-binding fragments, called "Fab" fragments, monovalent fragments consisting of the VL, VH, CL and CH domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the VH and VL domains of antibody, wherein these domains are present in a single polypeptide chain. The Fv polypeptide can further comprise a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., Science 242:423-426, 1988, and Huston et al., Proc. Natl. Acad. Sci. USA 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., Nature 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

Methods of Production of Anti-Osteopontin Antibodies

As discussed above, the present disclosure provides antibodies that specifically bind to osteopontin or a thrombin cleavage fragment thereof, wherein the antibody inhibits thrombin cleavage of osteopontin or interactions of thrombin-cleavage fragments of osteopontin with integrins and/or other cellular receptors. Exemplary methods of making an anti-osteopontin antibody are presented below.

Antibodies can be prepared using a wide variety of techniques known in the art including the use of hybridoma, recombinant, and phage display technologies, or a combination thereof. For example, antibodies may be made and isolated using methods of phage display. The antibody may also be isolated from sera of an animal host immunized with an immunogenic composition comprising osteopontin, which encompasses whole proteins and fragments thereof. Exemplary antibodies include an isolated antibody capable of specifically binding to osteopontin (e.g., at a thrombin cleavage site of osteopontin) or a thrombin cleavage fragment of osteopontin.

The antigen that coats the wells for phage display panning or the immunogenic composition used to elicit the antibody of the present disclosure may comprise an aggregate of one or more antigens. The method may involve exposing antigens to an aggregating condition so as to form an aggregate. Thus, the methods of production described above may further include a step of forming an aggregate of the isolated antigens. Examples of the aggregating conditions include heating, addition of an excipient that facilitates aggregation, and the like.

Antigens used to coat the wells for phage panning or to elicit antibodies of the present disclosure may be conjugated to another molecule. For example, the antigen can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., cancer cell, cardiomyocytes, etc.) or cellular location (e.g., plasma membrane, lysosome, endosome, mitochondria etc.), tissue or other bodily location (e.g., blood, particular organs, tumors, etc.).

A particular embodiment of an antigen conjugated to a second molecule is where the second molecule is an immunomodulator. "Immunomodulator" is a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid.

Phage Display

Phage display is used for the high-throughput screening of protein interactions. Phages may be utilized to display antigen-binding domains expressed from a repertoire or combinatorial antibody library (e.g., human or murine). Phage expressing an antigen binding domain that binds osteopontin or a thrombin cleavage fragment thereof can be selected or identified, e.g., using labeled osteopontin or osteopontin bound or captured to a solid surface or bead. Phage used in these methods are typically filamentous phage including fd and M13 binding domains expressed from phage with Fab, Fv (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, Immunol. Today 2000, 21:371; Nagy et al. Nat. Med. 2002, 8:801; Huie et al., Proc. Natl. Acad. Sci. USA 2001, 98:2682; Lui et al., J. Mol. Biol. 2002, 315:1063, each of which is incorporated herein by reference. Several publications (e.g., Marks et al., Bio/Technology 1992, 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., Nat. Biotechnol. 2000, 18:1287; Wilson et al., Proc. Natl. Acad. Sci. USA 2001, 98:3750; or Irving et al., J. Immunol. Methods 2001, 248:31). Cell surface libraries may be screened for antibodies (Boder et al., Proc. Natl. Acad. Sci. USA 2000, 97:10701; Daugherty et al., J. Immunol. Methods 2000, 243:211). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding heavy chain variable (VH) and light chain variable (VL) regions are amplified or otherwise isolated from animal cDNA libraries (e.g., human or murine cDNA libraries of lymphoid tissues) or synthetic cDNA libraries. The DNA encoding the VH and VL regions may be joined together by an scFv linker by PCR and cloned into a phagemid vector (e.g., p CANTAB 6 or pComb 3 HSS). The vector is electroporated in $E.\ coli$ and the $E.\ coli$ is infected with helper phage. The VH or VL regions are usually recombinantly fused to either the phage gene III or gene VIII. Phage expressing an antigen binding domain that binds to an antigen of interest (e.g., the serine protease domain of osteopontin) can be selected or identified with antigen, e.g., using labeled antigen or antigen bound or captured to a solid surface or bead.

Additional examples of phage display methods that may be used to make the antibodies include those disclosed in PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the references listed above, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and $F(ab')_2$ fragments can also be employed using methods known in the art such as those disclosed in PCT publication WO 92/22324; Mullinax et al., BioTechniques 1992, 12:864-869; and Sawai et al., AJRI 1995, 34:26-34; and Better et al., Science 1988, 240:1041-1043 (said references incorporated by reference in their entireties).

Immunization and Antibody Production

The method of eliciting antibodies in a host animal involves administering an effective amount of osteopontin or a fragment thereof as antigens to the host animal (i.e., a suitable mammal such as a mouse, rabbit or guinea pig, suitable avian, such as a chicken, or camelid) to elicit production of an antibody that specifically binds to osteopontin or a thrombin cleavage fragment thereof. Exemplary immunogenic peptides that may be used in eliciting an immune response in a host animal to produce anti-osteopontin antibodies include, without limitation, immunogenic peptides comprising or consisting of a sequence selected from the group consisting of SEQ ID NOS:5-7, SEQ ID NOS:9-12, and SEQ ID NO:47 (see also Examples). Methods of immunizing an animal, including the adjuvants used, booster schedules, sites of injection, suitable animals, etc. are well understood in the art, e.g., Harlow et al. (Antibodies: A Laboratory Manual, First Edition (1988) Cold spring Harbor, N.Y.), and administration of living cells to animals has been described for several mammals and birds, e.g., McKenzie et al (Oncogene 4:543-8, 1989), Scuderi et al (Med. Oncol. Tumor Pharmacother 2:233-42, 1985), Roth et al (Surgery 96:264-72, 1984) and Drebin et al (Nature 312:545-8, 1984). Next, a population of antibody producing cells is generated. In one embodiment, the population of cells is produced using hybridoma methods that well known to one of skill in the art (see, e.g., Harlow Antibodies: A Laboratory Manual, First Edition (1988) Cold Spring Harbor, N.Y.). Cells are fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). In alterative embodiments, populations of cells expressing monoclonal antibodies may be made using phage display methods.

Anti-osteopontin antibodies, including antigen binding fragments of anti-osteopontin antibodies, may also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Phage Panning and Screening

Once the population of antibody-producing cells or phages is produced, the antibodies are screened using one or a combination of a variety of assays. In general, these assays are functional assays, and may be grouped as follows: assays that detect an antibody's binding affinity or specificity, and assays that detect the ability of an antibody to initialize or inhibit a process.

For example, the antigen is coupled to beads or wells or other solid support and incubated with phage displaying the antibody of interest. After washings, bound phage is then recovered by inoculation of log phase $E.\ coli$ cells. The cells are grown and expanded with helper phage. Steps are repeated for the amplification of tightly bound phages. The phage-infected $E.\ coli$ colonies after several round of enrichment are harvested and Fab antibodies are purified from the periplasmic fractions. The purified antibodies are then analyzed in accordance with methods known in the art. Certain exemplary examples are detailed below.

The population of antibody isolated from phage-infected cells or hybridomas is further analyzed and/or screened for binding to a single antigen (i.e., antigens that are not mixed with other antigens of the plurality of antigens) of the plurality of antigens in vitro or in situ (e.g. on cells). Immunospecific binding may be carried out according to methods routine and known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. See, e.g., Ausubel et al, eds, 1994, Current Protocols in Molecular Biology, Vol. 1, John Wiley & Sons, Inc., New York, which is incorporated by reference herein in its entirety.

Antibodies of the present disclosure may also be screened in vivo. The method involves administering an anti-osteopontin antibody to an animal model for a disease or condition (i.e., osteopontin-associated disorder) and determining the effect of the antibody on the disease or condition of the model animal. In vivo assays of the invention include controls, where suitable controls include a sample in the absence of the antibody. Generally, a plurality of assay mixtures is run in parallel with different antibody concentrations to obtain a differential response to the various concentrations. Typically, one of these concentrations serves as a negative control, i.e., at zero concentration or below the level of detection.

A monoclonal antibody of interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Antibodies that have therapeutic value that have been identified using the methods and compositions of the invention are termed "therapeutic" antibodies.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

Methods of Screening

A screening method provided by the present disclosure may involve the use of a phage library to screen for an antibody that specifically binds to osteopontin or a thrombin cleavage fragment thereof, and optionally having any of the additional features described herein (e.g., inhibits thrombin cleavage of osteopontin or integrin binding to a thrombin cleavage fragment of osteopontin). The binding agent may be selected for its potent inhibition of osteopontin and/or its specific binding affinity. The method may be executed according to the phage display method described above.

Briefly, osteopontin or a fragment thereof may be immobilized on an ELISA plate or on beads through a covalent or non-covalent interaction, such as hydrophobic adsorption, biotin-avidin interaction, and $Ni^{2+}$-6xHis interaction. The phage library is then incubated with the immobilized antigen/protease, washed, and recovered. During panning and selection, the bound phage is recovered and amplified in *E. coli*. Multiple successive selection rounds ensure a selection of a phage displaying a polypeptide that acts as an antibody specific for osteopontin or a thrombin cleavage fragment thereof. The stringency of the washes increases over a number of rounds (e.g. three). Many techniques well known in the art may be employed to increase the specificity of the recovered phage. Examples include increased wash times, increased detergent concentrations, increased salt concentrations, and inclusion of known macromolecular inhibitors (e.g., small peptidic substrates, BPTI, Ecotin, and/or previously identified antibody inhibitors). Identification of inhibitory antibodies may include ELISAs and inhibition assays. Details on the assays to be performed in the method for selecting and isolating an anti-osteopontin antibody are discussed above.

Also contemplated by the present disclosure is a library of nucleic acid constructs encoding the candidate anti-osteopontin antibodies described herein. The library encodes a plurality of candidate anti-osteopontin antibodies that may have one or more polypeptide regions in common (e.g. at least one heavy chain or light chain CDR) and at least one other polypeptide region that varies among the population.

Nucleic Acids, Vectors, and Vector Systems Encoding Anti-Osteopontin Antibodies

In certain embodiments, anti-osteopontin antibody heavy chains and light chains or antibody fragments thereof (e.g., a Fab fragment, a Fab' fragment, a F(ab')$_2$ fragment, a $F_v$ fragment, or a scFv fragment) are produced from a vector. A "vector" is a composition of matter which can be used to deliver a nucleic acid of interest to the interior of a cell. Polynucleotides encoding an antibody light chain and/or heavy chain, or fragments thereof, can be introduced into a cell with a single vector or in separate vectors (i.e., vector system). The ability of constructs to produce anti-osteopontin antibodies can be empirically determined.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an anti-osteopontin antibody comprises a promoter "operably linked" to a polynucleotide encoding an anti-osteopontin heavy chain and/or light chain, or fragments thereof (e.g., comprising their variable domain CDRs). The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences may include UTRs comprising an internal ribosome entry site (IRES).

Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., *BioTechniques* (1997 22 150-161. A multitude of IRES sequences are known and include sequences derived from a wide variety of viruses, such as from leader sequences of picornaviruses such as the encephalomyocarditis virus (EMCV) UTR (Jang et al. *J. Virol.* (1989) 63:1651-1660), the polio leader sequence, the hepatitis A virus leader, the hepatitis C virus IRES, human rhinovirus type 2 IRES (Dobrikova et al., *Proc. Natl. Acad. Sci.* (2003) 100(25): 15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279(5):3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24(17):7622-7635), vascular endothelial growth factor IRES (Baranick et al. (2008) *Proc. Natl. Acad. Sci. U.S.A.* 105(12):4733-4738, Stein et al. (1998) *Mol. Cell. Biol.* 18(6):3112-3119, Bert et al. (2006) RNA 12(6):1074-1083), and insulin-like growth factor 2 IRES (Pedersen et al. (2002) *Biochem. J.* 363(Pt 1):37-44). These elements are readily commercially available in plasmids sold, e.g., by Clontech (Mountain View, CA), Invivogen (San Diego, CA), Addgene (Cambridge, MA) and GeneCopoeia (Rockville, MD). See also IRESite: The database of experimentally verified IRES structures (iresite.org). An IRES sequence may be included in a vector, for example, to express an anti-osteopontin antibody heavy chain or fragment thereof in combination with an anti-osteopontin antibody light chain or fragment thereof from an expression cassette.

Alternatively, a polynucleotide encoding a viral T2A peptide can be used to allow production of multiple protein products (e.g., an anti-osteopontin antibody heavy chain or fragment thereof in combination with an anti-osteopontin antibody light chain or fragment thereof) from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, Thosea asigna virus and porcine teschovirus-1. See, e.g., Kim et al. (2011) PLoS One 6(4):e18556, Trichas et al. (2008) BMC Biol. 6:40, Provost et al. (2007) Genesis 45(10):625-629, Furler et al. (2001) Gene Ther. 8(11):864-873; herein incorporated by reference in their entireties.

An expression vector or vector system comprising one or more vectors can be used to transform an isolated cell, a cell line, or a population of cells, wherein the gene products of interest (e.g., antibody light chain and heavy chain, or fragments thereof) are selectively expressed by the cell or cells. In some embodiments, anti-osteopontin antibodies are produced and secreted. The transformed cells secrete the antibodies into the surrounding media. Certain regulatory sequences can be included in the vector to enhance secretion, for example using a tissue plasminogen activator (TPA) leader sequence, an interferon (γ or α) signal sequence or other signal peptide sequences from known secretory proteins. The secreted antibodies can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the proteins are not secreted, and transformed cells are disrupted, using chemical, physical or mechanical means, which lyse the cells yet keep the recombinant proteins substantially intact. Intracellular proteins can also be obtained by removing components from the cell membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulfate, Triton, NP40 and CHAPS. The particular technique used to disrupt the cells is largely a matter of choice and will depend on the cell type in which a polypeptide is expressed, culture conditions and any pre-treatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

Antibodies including heavy and light chains, or fragments thereof can be purified using affinity purification, such as by Protein A affinity chromatography, immunoaffinity chromatography using antibodies that bind to an anti-osteopontin heavy chain or light chain epitope), or antigen-specific affinity chromatography with an immobilized osteopontin antigen. The choice of a suitable affinity resin is within the skill in the art. After affinity purification, expressed antibodies can be further purified using conventional techniques well known in the art, such as by any of the techniques described above.

Antibody Conjugates

Anti-osteopontin antibodies also find use in therapeutic and diagnostic (e.g., in vivo imaging, etc.) applications. For example, such an antibody may be conjugated to a payload, such as a therapeutic agent (e.g., a cytotoxic payload) or labeling agent (e.g., an in vivo imaging agent), where upon binding of the antibody to osteopontin or a thrombin cleavage fragment thereof, the therapeutic or labeling agent is delivered selectively to a target cell having elevated levels of osteopontin or thrombin cleavage fragments thereof (e.g., cancerous cell overexpressing osteopontin). The selective targeting of the therapeutic or imaging agent to cells overexpressing osteopontin reduces unwanted exposure of non-target cells to the therapeutic agent, and can reduce toxicity upon administration. Moreover, in imaging applications (e.g., in vivo imaging for diagnostic, prognostic, and/or any other purpose), selective binding of the antibody to cells overexpressing osteopontin concentrates the imaging agent in such cells, thereby increasing the signal-to-noise ratio and diagnostic/prognostic value of the resulting images.

Accordingly, any anti-osteopontin antibody described herein may be in unconjugated form, or may be conjugated directly to an agent, such as a therapeutic and/or imaging (e.g., diagnostic) agent, or may be conjugated indirectly to carrier polymers comprising such other therapeutic or imaging agents.

In some embodiments, the antibody is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., 1986) supra). Suitable toxins include: bacterial toxins such as diphtheria toxin; plant toxins such as ricin; small molecule toxins such as geldanamycin (Mandler et al J. Natl. Cancer Inst. 92(19):1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-84 (2003) and calicheamicin (Lode et al., Cancer Res. 58:2928 (1998); Hinman et al., Cancer Res. 53:3336-3342 (1993)).

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are known; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

In certain aspects, the imaging agent of an anti-osteopontin antibody conjugate of the present disclosure is an imaging agent that finds use in in vivo imaging, such as near-infrared (NIR) optical imaging, single-photon emission computed tomography (SPECT)/CT imaging, or the like. Labeling agents that find use in such applications include, but are not limited to, fluorescent labels and radioisotopes, or the like. In certain aspects, the labeling agent is a multi-modal in vivo imaging agent that permits in vivo imaging using two or more imaging approaches (e.g., see Thorp-Greenwood and Coogan (2011) Dalton Trans. 40:6129-6143).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agents. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, and can be about 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agents. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic, chemotherapeutic agents described herein.

Conjugated antibodies can be prepared by directly conjugating an antibody component with a therapeutic agent or labeling agent. The general procedure is analogous to the indirect method of conjugation except that a therapeutic or labeling agent is directly attached to an oxidized antibody component. For example, a carbohydrate moiety of an antibody can be attached to polyethylene glycol to extend half-life.

A therapeutic or labeling agent can be attached at the hinge region of a reduced antibody component via disulfide bond formation, or using a heterobifunctional cross-linker, such as N-succinyl 3-(2-pyridyldithio)propionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Pharmaceutical Compositions

An anti-osteopontin antibody or antigen-binding fragment thereof (or conjugate including the same) can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the antibodies or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include:

polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral or localized delivery.

The pharmaceutical preparations herein can also be housed in a syringe, an implantation device, or the like, depending upon the intended mode of delivery and use. Preferably, the compositions comprising anti-osteopontin antibodies or antigen-binding fragments thereof (or conjugates including the same) described herein are in unit dosage form, meaning an amount of the anti-osteopontin antibodies or antigen-binding fragments thereof (or conjugates including the same) appropriate for a single dose, in a premeasured or pre-packaged form.

The compositions herein may optionally include one or more additional agents, such as drugs for treating an osteopontin-associated disorder or other medications used to treat a subject for a condition or disease. For example, compounded preparations may include anti-osteopontin antibodies or antigen-binding fragments thereof (or conjugates including the same) and one or more drugs for treating cancer, such as, but not limited to, chemotherapeutic agents, immunotherapeutic agents, biologic therapeutic agents, pro-apoptotic agents, angiogenesis inhibitors, photoactive agents, radiosensitizing drugs, and radioisotopes. For treating melanoma, compounded preparations may include a B-Raf inhibitor, a MEK inhibitor, or a combination thereof. Exemplary B-Raf inhibitors include, without limitation, dabrafenib, vemurafenib, sorafenib, LGX818, GDC-0879, and PLX-4720. Exemplary MEK inhibitors include, without limitation, trametinib, cobimetinib, binimetinib, selumetinib, and PD-325901. Alternatively, such agents can be contained in a separate composition from the composition comprising the anti-osteopontin antibodies or antigen-binding fragments thereof (or conjugates including the same) and co-administered concurrently, before, or after the composition comprising the anti-osteopontin antibodies or antigen-binding fragments thereof (or conjugates including the same).

Methods of Treating an Osteopontin-Associated Disorder

The present disclosure provides methods of treating an osteopontin-associated disorder related to the activity of osteopontin. Exemplary osteopontin-associated disorders include any disease or disorder associated with elevated levels of osteopontin or thrombin cleavage fragments thereof, including, without limitation, inflammation, cardiac hypertrophy, myocardial fibrosis, and cancers over-expressing osteopontin, such as melanoma, glioblastoma, ovarian cancer, breast cancer, and lung cancer.

The methods generally involve administering to a subject in need thereof a therapeutically effective amount of any anti-osteopontin antibody, antigen-binding fragment, or conjugate described herein, either alone (e.g., monotherapy) or in combination (e.g., combination therapy) with one or more additional therapeutic agents (e.g., anti-cancer therapeutic agents, B-Raf inhibitors, and/or MEK inhibitors). In certain aspects, the methods include treating an osteopontin-associated disorder by administering to a patient in need thereof a therapeutically effective amount of an anti-osteopontin antibody (e.g., an antibody of the present disclosure that specifically binds to osteopontin or a thrombin cleavage fragment thereof, wherein the antibody inhibits thrombin cleavage of osteopontin or integrin binding to a thrombin cleavage fragment of osteopontin).

A variety of hosts are treatable according to the methods. Generally, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Prodrugs of the antibody composition of the present disclosure are also contemplated in the methods described herein. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Dosage

In the methods of the present disclosure, an effective amount of anti-osteopontin antibody or antigen-binding fragment thereof (or conjugate including the same) is administered to a subject in need thereof. The amount administered varies depending upon the goal of the administration, the particular osteopontin-associated disorder being treated, the health and physical condition of the individual to be treated, age, the taxonomic group of individual to be treated (e.g., human, non-human primate, primate, etc.), the degree of resolution desired, the formulation of the anti-osteopontin antibody or conjugate, the treating clinician's assessment of the medical situation, and other relevant factors. It is expected that the amount will fall in a relatively broad range that can be determined through routine trials. For example, the amount of the anti-osteopontin antibody or conjugate employed to inhibit inflammation, cardiac hypertrophy, myocardial fibrosis, or cancer cell growth, metastasis and/or invasiveness is not more than about the amount that could otherwise be irreversibly toxic to the subject (i.e., maximum tolerated dose). In other cases, the amount is around or even well below the toxic threshold, but still in an effective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the antibody or conjugate, and thus based on the disposition of the composition within the subject. This includes consideration of the route of administration as well as dosage amount, which can be adjusted for, e.g., parenteral (applied by routes other than the digestive tract for systemic or local effects) applications. For instance, administration of an anti-osteopontin antibody or conjugate is typically topical or via injection (e.g., intravenous, intramuscular, or intratumoral), or a combination thereof.

Disposition of the antibody or conjugate and its corresponding biological activity within a subject is typically gauged against the fraction of antibody present at a target of interest. For example, an antibody, once administered, can accumulate at a biological target (e.g., osteopontin) that concentrates the material in diseased cells with elevated levels of osteopontin or thrombin cleavage fragments thereof. Thus, dosing regimens in which the antibody is administered so as to accumulate in a target of interest over time can be part of a strategy to allow for lower individual doses. This can also mean, for example, that a dose of an antibody that is cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC50 of a given antibody for inhibiting thrombin cleavage of osteopontin or integrin binding to thrombin cleavage fragments of osteopontin. By "IC50" is intended the concentration required for 50% inhibition in vitro. Alternatively, the effective amount can be gauged from the EC50 of a given antibody concentration. By "EC50" is intended the plasma concentration required for obtaining 50% of a maximum effect in vivo.

In general, with respect to the anti-osteopontin antibody or conjugate of the present disclosure, an effective amount is usually not more than 200× the calculated IC50. Typically, the amount of an antibody or conjugate that is administered is less than about 200×, less than about 150×, less than about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

An effective amount may not be more than 100× the calculated EC50. For instance, the amount of antibody or conjugate that is administered is less than about 100×, less than about 50×, less than about 40×, 35×, 30×, or 25× and many embodiments less than about 20×, less than about 15× and even less than about 10×, 9.times, 9×, 7×, 6.times, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays.

Administration

At least one therapeutically effective dose of an anti-osteopontin antibody or antigen-binding fragment thereof (or conjugate thereof) that inhibits thrombin cleavage of osteopontin or integrin binding to a thrombin cleavage fragment of osteopontin will be administered. By "therapeutically effective dose or amount" of an anti-osteopontin antibody or antigen-binding fragment thereof is intended an amount that when administered brings about a positive therapeutic response with respect to treatment of an individual for an osteopontin-associated disorder. Of particular interest is an amount of an anti-osteopontin antibody, or antigen-binding fragment thereof, that provides an anti-tumor or anti-inflammatory effect or reduces cardiac hypertrophy or myocardial fibrosis. By "positive therapeutic response" is intended the individual undergoing the treatment according to the invention exhibits an improvement in one or more symptoms of the osteopontin-associated disorder for which the individual is undergoing therapy.

Thus, for example, a "positive therapeutic response" would be an improvement in the disease in association with the therapy, and/or an improvement in one or more symptoms of the disease in association with the therapy. For example, a positive therapeutic response for treatment of a cancer would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements (for patients with evaluable response only, partial response does not apply).

In certain embodiments, multiple therapeutically effective doses of compositions comprising an anti-osteopontin antibody or antigen-binding fragment thereof (or conjugate thereof), and/or one or more other therapeutic agents, such as other drugs for treating cancer, inflammation, cardiac hypertrophy, myocardial fibrosis or other medications will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, an anti-osteopontin antibody or antigen-binding fragment thereof (or conjugate thereof) will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7-day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7-day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

The compositions comprising an anti-osteopontin antibody, or antigen-binding fragment thereof (of conjugate thereof), are typically, although not necessarily, administered orally, via injection (subcutaneously, intravenously, or intramuscularly), by infusion, topically, or locally. Additional modes of administration are also contemplated, such as intra-arterial, intraperitoneal, pulmonary, nasal, transdermal, intralesion, intrapleural, intraparenchymatous, rectal, transdermal, transmucosal, intrathecal, pericardial, intra-arterial, intraocular, and so forth. When administering an anti-osteopontin antibody, or antigen-binding fragment thereof (of conjugate thereof) by injection, the administration may be by continuous infusion or by single or multiple boluses.

For example, the anti-osteopontin antibody or conjugate may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g., by infusion) can be repeated over a desired period, e.g., repeated over a period of about 1 day to about 5 days or once every several days, for example, about five days, over about 1 month, about 2 months, etc.

The preparations according to the invention are also suitable for local treatment. In a particular embodiment, a composition is used for localized delivery of an anti-osteopontin antibody or antigen-binding fragment thereof (or conjugate thereof) for the treatment of cancer. For example, compositions may be administered directly into a tumor or cancerous cells. Administration may be by perfusion through a regional catheter or direct intralesional injection. For treatment of melanoma, compositions may be administered topically, for example, in a cream or gel containing the anti-osteopontin antibody or antigen-binding fragment thereof (or conjugate thereof) that is applied to the skin at the site of a lesion.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising an anti-osteopontin antibody or antigen-binding fragment thereof (or conjugate thereof) and other agents may be administered using the same or different routes of administration in accordance with any medically acceptable method known in the art.

In another embodiment, the pharmaceutical compositions comprising an anti-osteopontin antibody or antigen-binding fragment thereof (or conjugate thereof) and/or other agents are administered prophylactically, e.g., to prevent development or progression of an osteopontin-associated disorder. Such prophylactic uses will be of particular value for subjects at high risk of cancer progression or cardiac hypertrophy or fibrosis.

In another embodiment of the invention, the pharmaceutical compositions comprising an anti-osteopontin antibody or antigen-binding fragment thereof (or conjugate thereof) and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising a an anti-osteopontin antibody or antigen-binding fragment thereof (e.g., conjugated to a therapeutic agent, detectable label, or imaging agent) as provided herein to a patient with an osteopontin-associated disorder. The method comprises administering, via any of the herein described modes, a therapeutically effective amount of the conjugate or drug delivery system, preferably provided as part of a pharmaceutical composition. The method of administering may be used to treat any osteopontin-associated disorder that is responsive to treatment with an anti-osteopontin antibody. More specifically, the compositions herein are effective in treating inflammation, cardiac hypertrophy/fibrosis and cancers associated with elevated expression of osteopontin.

Those of ordinary skill in the art will appreciate which conditions an anti-osteopontin antibody can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Generally, a therapeutically effective amount will range from about 0.50 mg to 5 grams of an anti-osteopontin antibody or antigen-binding fragment thereof (or conjugate thereof) daily, more preferably from about 5 mg to 2 grams daily, even more preferably from about 7 mg to 1.5 grams daily. Preferably, such doses are in the range of 10-600 mg four times a day (QID), 200-500 mg QID, 25-600 mg three times a day (TID), 25-50 mg TID, 50-100 mg TID, 50-200 mg TID, 300-600 mg TID, 200-400 mg TID, 200-600 mg TID, 100 to 700 mg twice daily (BID), 100-600 mg BID, 200-500 mg BID, or 200-300 mg BID. The amount of compound administered will depend on the potency of the specific anti-osteopontin antibody or antigen-binding fragment thereof (or conjugate thereof) and the magnitude or effect desired and the route of administration.

A purified anti-osteopontin antibody or antigen-binding fragment thereof or conjugate thereof (again, preferably provided as part of a pharmaceutical preparation) can be administered alone or in combination with one or more other therapeutic agents for treating an osteopontin-associated disorder, such as anti-cancer therapeutic agents, such as chemotherapy, immunotherapy, biologic or targeted therapy agents, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

An anti-osteopontin antibody or antigen-binding fragment thereof or conjugate thereof can be administered prior to, concurrent with, or subsequent to other agents. If provided at the same time as other agents, the anti-osteopontin antibody or antigen-binding fragment thereof or conjugate thereof can be provided in the same or in a different composition. Thus, the anti-osteopontin antibody or antigen-binding fragment thereof or conjugate thereof and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising an anti-osteopontin antibody or antigen-binding fragment thereof or conjugate thereof and a dose of a pharmaceutical composition comprising at least one other agent, such as another drug for treating cancer, which in combination comprise a therapeutically effective dose, according to a particular dosing regimen. Similarly, the anti-osteopontin antibody or antigen-binding fragment thereof or conjugate thereof and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Where a subject undergoing therapy in accordance with the previously mentioned dosing regimens exhibits a partial response or a relapse following a prolonged period of remission, subsequent courses of concurrent therapy may be needed to achieve complete remission of the disease. Thus, subsequent to a period of time off from a first treatment period, a subject may receive one or more additional treatment periods with an anti-osteopontin antibody or antigen-binding fragment thereof or conjugate thereof. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these therapeutic agents.

In patients with cancer, treatment with an anti-osteopontin antibody or antigen-binding fragment thereof or conjugate thereof may be combined with any other medical treatment for cancer, such as, but not limited to, surgery, radiation therapy, chemotherapy, hormonal therapy, immunotherapy, or molecularly targeted or biologic therapy. Any combination of these other medical treatment methods with an anti-osteopontin antibody or antigen-binding fragment thereof or conjugate thereof may be used to effectively treat cancer in a subject.

For example, treatment with an anti-osteopontin antibody or antigen-binding fragment thereof or conjugate thereof may be combined with chemotherapy with one or more chemotherapeutic agents such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

In another example, treatment with an anti-osteopontin antibody or antigen-binding fragment thereof or conjugate thereof may be combined with targeted therapy with one or more small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax and gossypol; PARP inhibitors, such as Iniparib and Olaparib; PI3K inhibitors, such as perifosine; VEGF receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar); and monoclonal antibodies, such as Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

In a further example, treatment with an anti-osteopontin antibody or antigen-binding fragment thereof or conjugate thereof may be combined with immunotherapy, including, but not limited to, using any of the following: a cancer vaccine (e.g., E75 HER2-derived peptide vaccine, nelipepimut-S (NeuVax), Sipuleucel-T), antibody therapy (e.g., Trastuzumab, Ado-trastuzumab emtansine, Alemtuzumab, Ipilimumab, Ofatumumab, Nivolumab, Pembrolizumab, or Rituximab), cytokine therapy (e.g., interferons, including type I (IFNα and IFNβ), type II (IFNγ) and type III (IFNλ) and interleukins, including interleukin-2 (IL-2)), adjuvant immunochemotherapy (e.g., polysaccharide-K), adoptive T-cell therapy, and immune checkpoint blockade therapy.

In a further example, treatment with an anti-osteopontin antibody or antigen-binding fragment thereof or conjugate thereof may be combined with radiation therapy with a radioisotope, including, but not limited to, iodine-131, strontium-89, samarium-153, and radium-223. In addition, radiation therapy may be combined with administration of a radiosensitizing drug such as, but not limited to, Cisplatin, Nimorazole, and Cetuximab.

For patients with melanoma, treatment with an anti-osteopontin antibody or antigen-binding fragment thereof or conjugate thereof may be combined with administration of a B-Raf inhibitor, a MEK inhibitor, or a combination thereof. Exemplary B-Raf inhibitors include, without limitation, dabrafenib, vemurafenib, sorafenib, LGX818, GDC-0879, and PLX-4720. Exemplary MEK inhibitors include, without limitation, trametinib, cobimetinib, binimetinib, selumetinib, and PD-325901.

Kits

Any of the compositions described herein may be included in a kit. For example, kits may include compositions comprising anti-osteopontin antibodies, antigen-binding fragments thereof, conjugates of anti-osteopontin antibodies, pharmaceutical formulations comprising anti-osteopontin antibodies and/or conjugates thereof, recombinant nucleic acids or vector systems encoding the anti-osteopontin antibodies and/or host cells (either transfected with the recombinant nucleic acids or vector systems encoding the anti-osteopontin antibodies or separate).

In some embodiments, the kit comprises an anti-osteopontin antibody or an antigen-binding fragment thereof that specifically binds to osteopontin or a thrombin cleavage fragment thereof, wherein the antibody inhibits thrombin cleavage of osteopontin or integrin binding to a thrombin cleavage fragment of osteopontin. In certain embodiments, the kit comprises anti-osteopontin antibody conjugates or formulations including the antibodies and/or conjugates.

In certain embodiments, the antibody or antigen-binding fragment thereof included in the kit specifically binds to an OPN-R fragment or an OPN-CTF fragment. In certain embodiments, the antibody or antigen-binding fragment thereof specifically binds to an epitope comprising Arg168 of osteopontin. In certain embodiments, the antibody or antigen-binding fragment thereof specifically binds to an osteopontin peptide comprising a sequence selected from the group consisting of SEQ ID NOS:1-7, SEQ ID NOS:9-12, and SEQ ID NO:47.

In certain embodiments, the antibody or antigen-binding fragment thereof included in the kit comprises a heavy chain complementarity-determining region 1 (CDR-H1) comprising the amino acid sequence of SEQ ID NO:29; a heavy chain complementarity-determining region 2 (CDR-H2) comprising the amino acid sequence of SEQ ID NO:30; a heavy chain complementarity-determining region 3 (CDR-H3) comprising the amino acid sequence of SEQ ID NO:31; a light chain complementarity-determining region 1 (CDR-L1) comprising the amino acid sequence of SEQ ID NO:32; a light chain complementarity-determining region 2 (CDR-L2) comprising the amino acid sequence of SEQ ID NO:33; and a light chain complementarity-determining region 3 (CDR-L3) comprising the amino acid sequence of SEQ ID NO:34. In some embodiments, the antibody or antigen-binding fragment thereof comprises a heavy chain comprising the amino acid sequence of SEQ ID NO:14 or SEQ ID NO:18, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:16 or SEQ ID NO:20, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the antibody or antigen-binding fragment thereof included in the kit comprises a heavy chain complementarity-determining region 1 (CDR-H1) comprising the amino acid sequence of SEQ ID NO:35; a heavy chain complementarity-determining region 2 (CDR-H2) comprising the amino acid sequence of SEQ ID NO:36; a heavy chain complementarity-determining region 3 (CDR-H3) comprising the amino acid sequence of SEQ ID NO:37; a light chain complementarity-determining region 1 (CDR-L1) comprising the amino acid sequence of SEQ ID NO:38; a light chain complementarity-determining region 2 (CDR-L2) comprising the amino acid sequence of SEQ ID NO:39; and a light chain complementarity-determining region 3 (CDR-L3) comprising the amino acid sequence of SEQ ID NO:40. In some embodiments, the antibody or antigen-binding fragment thereof comprises a heavy chain comprising the amino acid sequence of SEQ ID NO:22, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:24, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the antibody or antigen-binding fragment thereof included in the kit comprises a heavy chain complementarity-determining region 1 (CDR-H1) comprising the amino acid sequence of SEQ ID NO:41; a heavy chain complementarity-determining region 2 (CDR-H2) comprising the amino acid sequence of SEQ ID NO:42; a heavy chain complementarity-determining region 3 (CDR-H3) comprising the amino acid sequence of SEQ ID NO:43; a light chain complementarity-determining region 1 (CDR-L1) comprising the amino acid sequence of SEQ ID NO:44; a light chain complementarity-determining region 2 (CDR-L2) comprising the amino acid sequence of SEQ ID NO:45; and a light chain complementarity-determining region 3 (CDR-L3) comprising the amino acid sequence of SEQ ID NO:46. In some embodiments, the antibody or antigen-binding fragment thereof comprises a heavy chain comprising the amino acid sequence of SEQ ID NO:26, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the antibody or antigen-binding fragment thereof comprises a light chain comprising the amino acid sequence of SEQ ID NO:28, sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In certain embodiments, the anti-osteopontin antibody included in the kit is a monoclonal antibody, a polyclonal antibody, a chimeric antibody, a humanized antibody, a nanobody, a bispecific antibody, a bispecific T cell engager antibody, a trispecific antibody, a Fab fragment, a Fab' fragment, a F(ab')$_2$ fragment, a F$_v$ fragment, or a scFv fragment.

The kit may include one or more pharmaceutical formulations that include the antibody compositions described herein. As such, the kits may include a single pharmaceutical composition present as one or more unit dosages. In yet other embodiments, the kits may include two or more separate pharmaceutical compositions. In some embodiments, the pharmaceutical composition is suitable for topical delivery (e.g., a gel or cream comprising an antibody or conjugate for treatment of melanoma).

In some embodiments, the kit may further include a composition comprising a B-Raf inhibitor, a MEK inhibitor, or a combination thereof.

In some embodiments, the kit may further include a composition comprising one or more anti-cancer therapeutic agents including, but not limited to, a chemotherapeutic agent, an immunotherapeutic agent, a biologic therapeutic agent, a pro-apoptotic agent, an angiogenesis inhibitor, a photoactive agent, a radiosensitizing agent, and a radioisotope, or a combination thereof.

Compositions can be in liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may also provide a delivery device pre-filled with the anti-osteopontin antibody or antigen-binding fragment thereof (or conjugate thereof).

In addition to the above components, the subject kits may further include (in certain embodiments) instructions for practicing the subject methods (i.e., instructions for treating an osteopontin-associated disorder as described herein). These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), DVD, Blu-ray, flash drive, and the like, on which the information has been recorded. Yet another form of these instructions that may be present is a website address which may be used via the internet to access the information at a removed site.

Utility

The anti-osteopontin antibodies or antigen-binding fragments thereof (or conjugates thereof), described herein, are useful for treating an osteopontin-associated disorder, including any disease or disorder associated with elevated levels of osteopontin or thrombin cleavage fragments thereof, such as inflammation, cardiac hypertrophy, myocardial fibrosis, and cancers over-expressing osteopontin, such as melanoma, glioblastoma, ovarian cancer, breast cancer, and lung cancer.

In particular, anti-osteopontin antibodies or antigen-binding fragments thereof (or conjugates thereof) are useful for treating melanoma, including, without limitation, lentigo maligna, lentigo maligna melanoma, superficial spreading melanoma, acral lentiginous melanoma, mucosal melanoma, nodular melanoma, polypoid melanoma, and desmoplastic melanoma. The melanoma cells may contain changes (mutations) in their genomic DNA sequence that mean that the proteins encoded by melanoma cells differ from those elsewhere in the patient's body. As an example, the protein, B-RAF, which is involved in signaling growth to the cell, can have mutations. In particular, an anti-osteopontin antibody or antigen-binding fragments thereof (or conjugates thereof) can be used to treat B-RAF-mutated melanoma, including without limitation, melanoma comprising a V600E mutation or a V600K mutation. Anti-osteopontin antibodies (or antigen-binding fragments thereof) can be used to treat melanoma at any stage, including metastatic melanoma.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Thrombin Cleavage of Osteopontin Enhances Melanoma Growth and Progression

Osteopontin (OPN) is a matricellular multifunctional protein with a highly conserved RGD domain that binds to a wide range of integrins. Thrombin cleaves OPN into two fragments, OPN-R, which has a new integrin binding site, and a C-terminal fragment (CTF), which enhances chemotaxis (FIG. 1). OPN-R, which has SVVYGLR (SEQ ID NO:3) at its C-terminus, binds to integrins α4β1 and α9β1. Mutation of the arginine at the thrombin cleavage site into alanine (R153A) renders OPN resistant to thrombin cleavage. It has been reported by Nemoto et al (J. Bone Mineral Res. 2001) that growth of B16 melanoma is suppressed in mice lacking OPN (OPN knock-out [KO] mice). However, despite extensive studies on the importance of OPN in cancer progression, the role of thrombin cleavage of OPN is unknown.

To further understand the role of thrombin cleavage of OPN in the pathology of inflammatory disorders and cancers, the thrombin cleavage site of OPN was abrogated by introducing an Arg153Ala mutation into the OPN gene in experimental mouse models. Mice with OPN resistant to thrombin cleavage were generated by replacing Arg153 with Ala (OPNR153A; OPN knock in [KI]). Mice were inoculated subcutaneously on their flanks with B16 melanoma cells, and tumor growth was monitored and, tumor weight was measured after sacrifice. In a model of metastasis, mice were injected with B16 melanoma cells intravenously through the tail vein and after sacrifice, the melanoma in the lungs was quantitated by visually counting the numbers of nodules and by determining the melanin content (melanin is an accepted measure of the amount of melanoma cells in the lungs). Some mice were fed a chow containing the thrombin inhibitor, dabigatran etexilate.

Figure 2A:
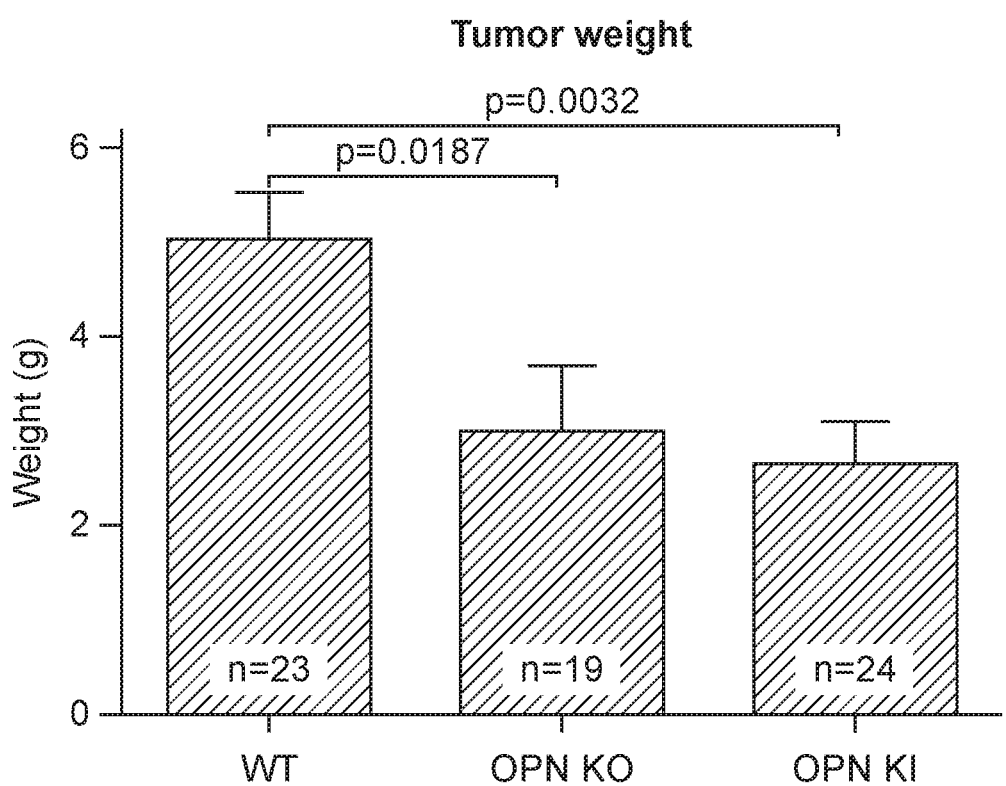
FIGS. 2A-2B show decreased B16 tumor growth in OPN KO and OPNR153A KI mice compared to WT mice.
Figure 2B:
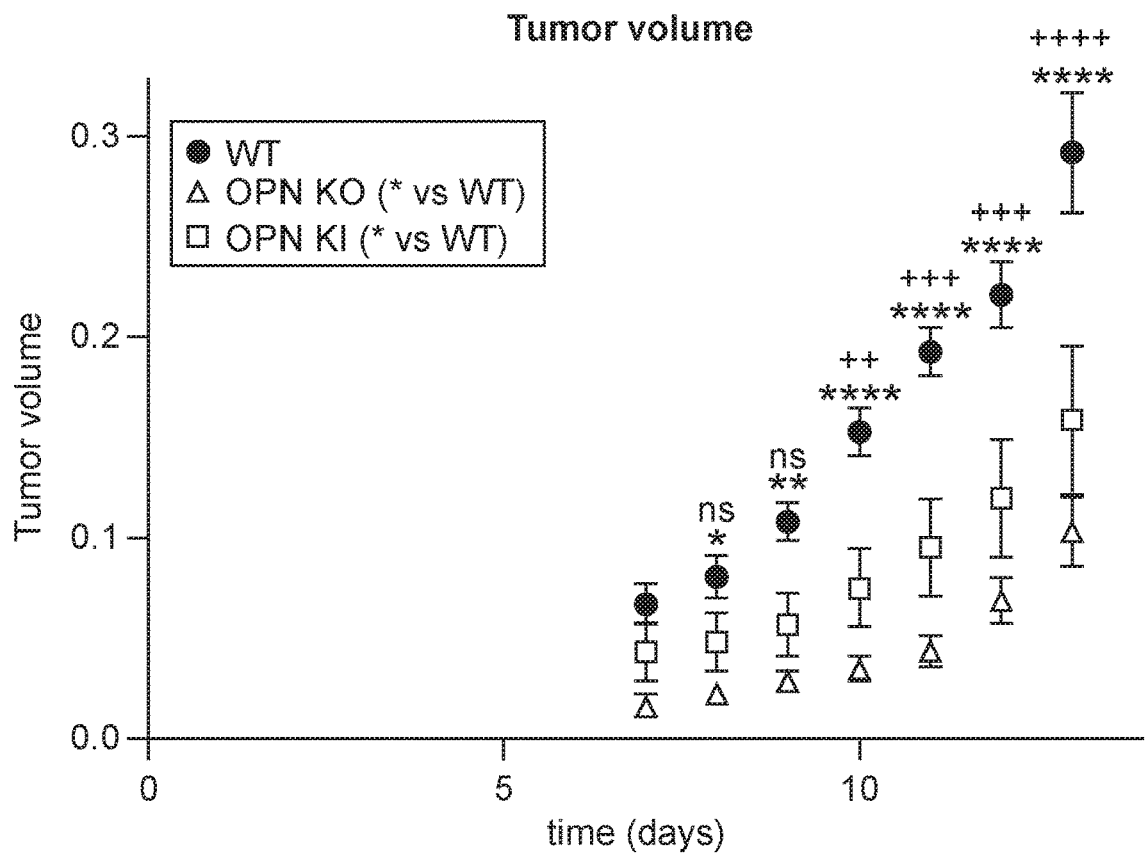
Figure 3A:
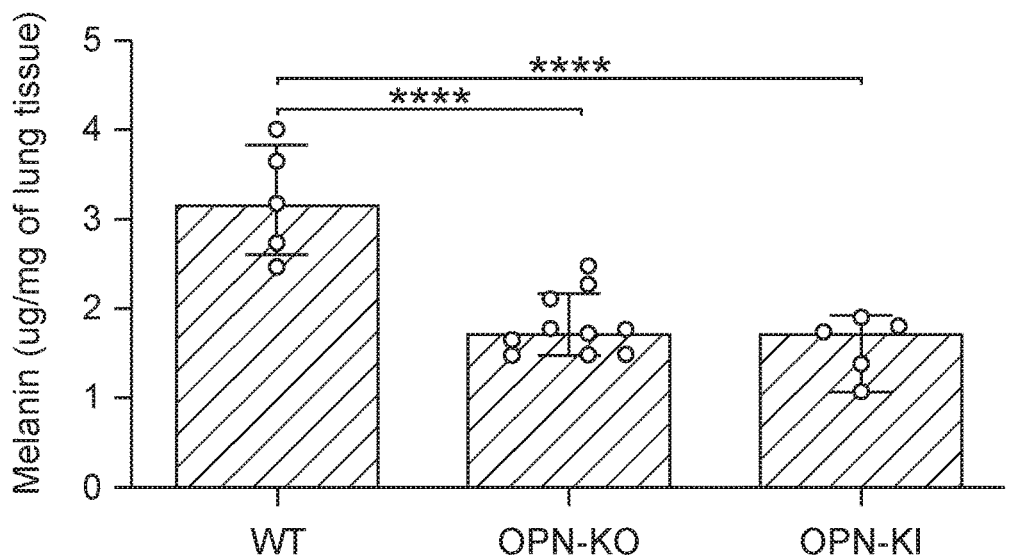
FIGS. 3A-3B show that B16 tumor growth was suppressed similarly in metastasis models for OPN KO and OPN KI mice.
Figure 3B:
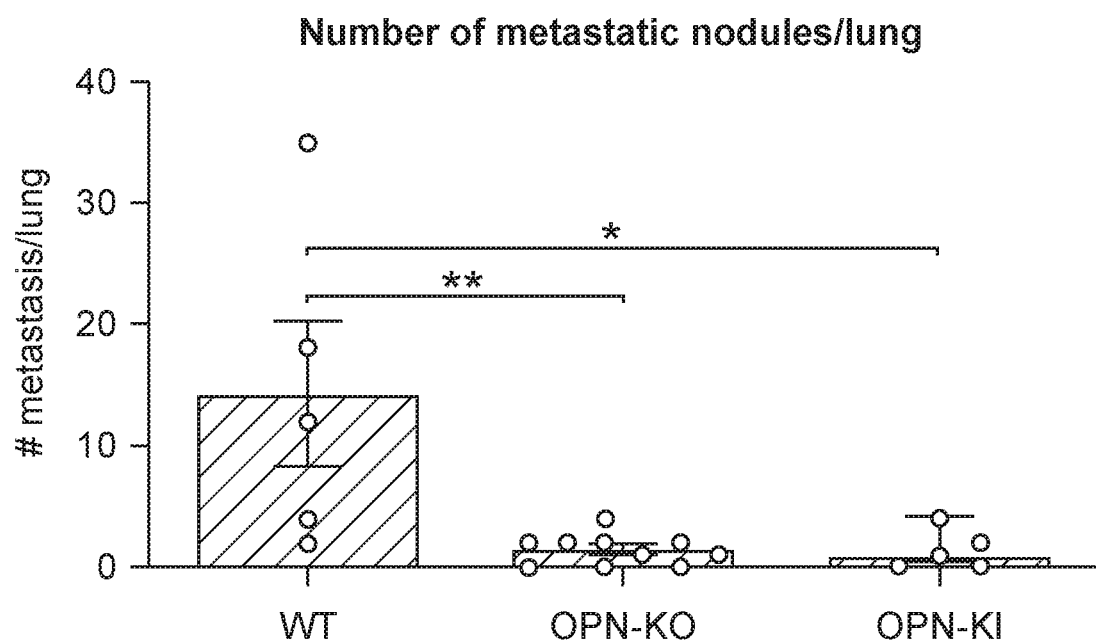

Robust tumor growth was observed in wild-type (WT) mice whereas tumor growth was suppressed in both OPN knock-out (KO) and OPNR153A-KI mice to about the same extent when monitored as volume over time or weight upon sacrifice (FIGS. 2A-2B). In the metastasis model, WT mice had more tumor nodules in the lungs and there was more melanin in the lungs than in OPN KI mice (FIGS. 3A-3B).

Figure 4A:
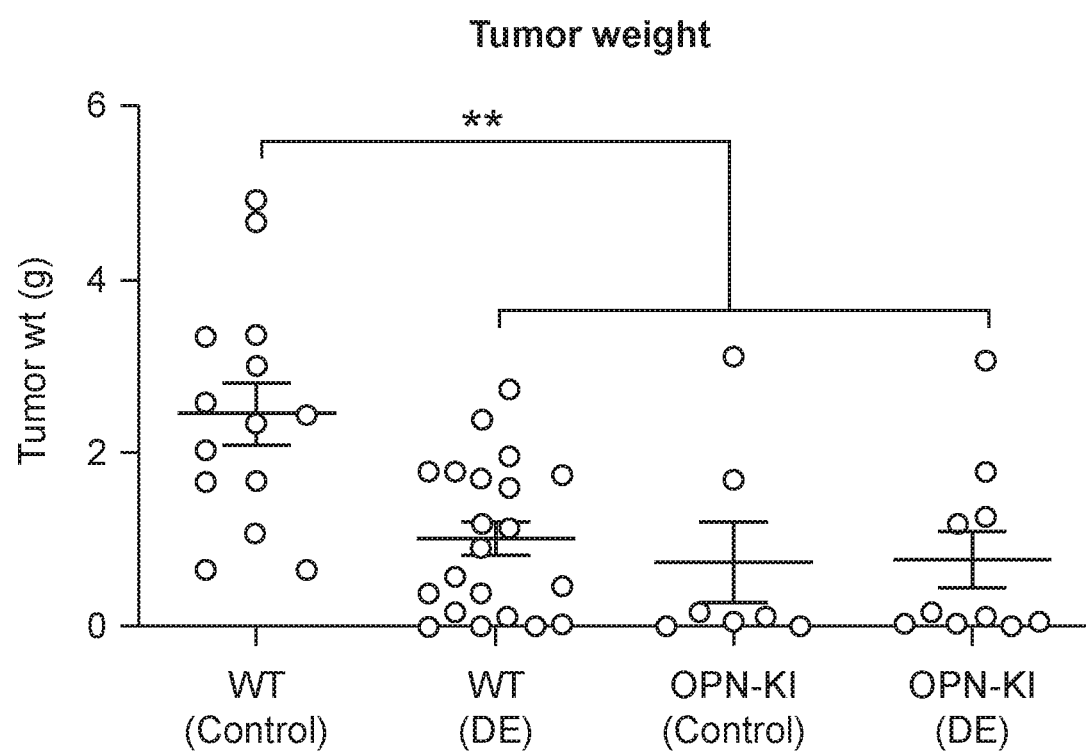
FIGS. 4A-4B show dabigatran etexilate treatment of mice carrying B16 melanomas on their flank suppressed tumor growth in WT but not OPN-KI mice.
Figure 4B:
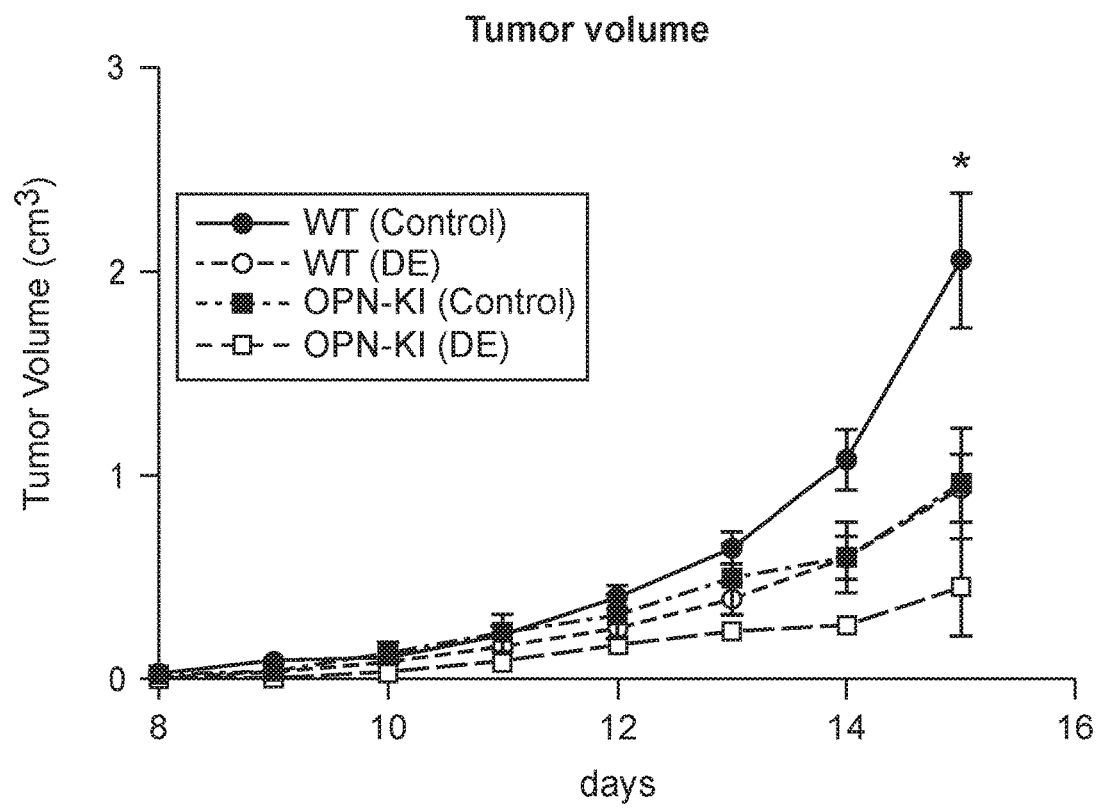
Figure 5A:
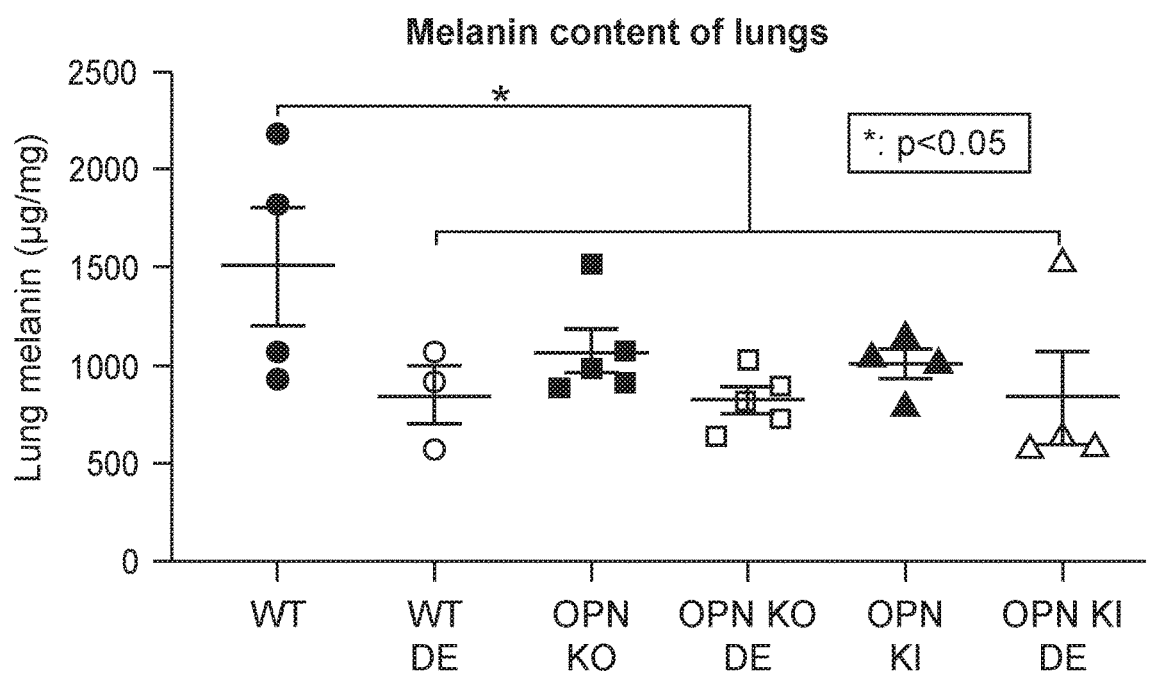
FIGS. 5A-5B show dabigatran etexilate treatment of mice with B16 melanoma metastases in their lungs suppressed tumor growth in WT but not OPN-KO or OPN-KI mice.
Figure 5B:
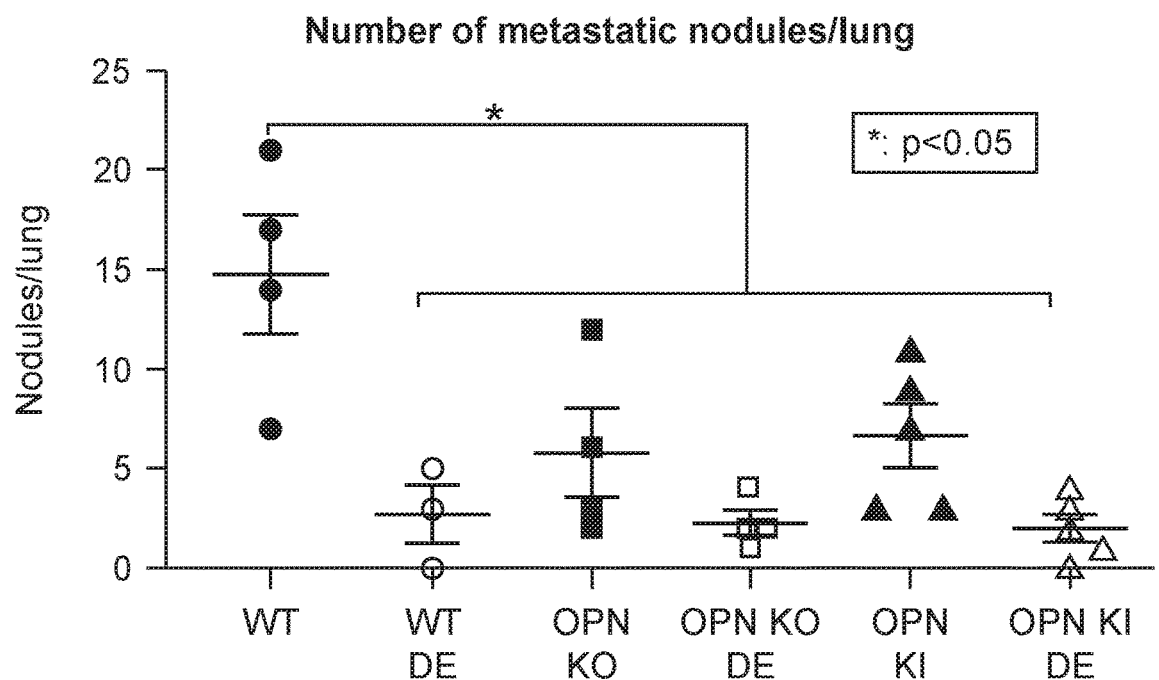
Figure 6:
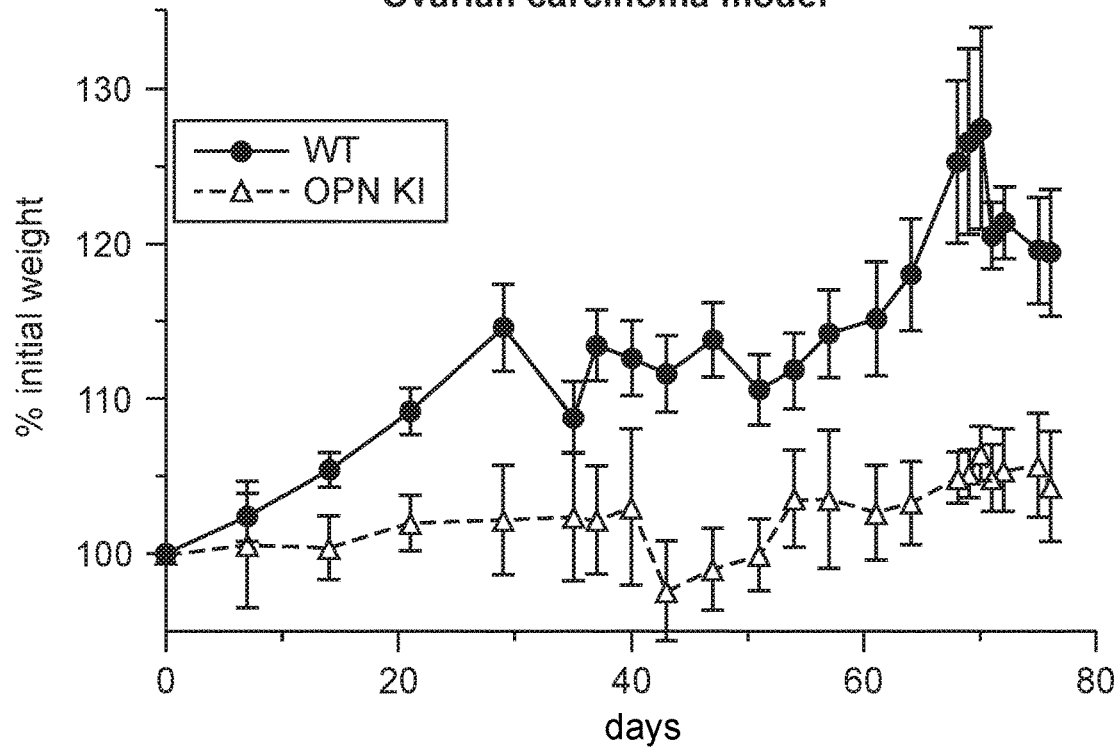
FIG. 6 shows decreased Id8 ovarian carcinoma growth in OPN-KI mice compared to WT mice.

The role of thrombin-cleavage of OPN was confirmed by treating mice with a specific oral thrombin inhibitor, dabigatran etexilate (DE). In wild type mice (WT) treated with DE, tumor growth on the flanks (FIGS. 4A-4B) was reduced to the same level found in OPN-KI mice. Similarly, in the metastasis model, metastasis was reduced in WT mice to the same level found in OPN-KI and OPN-KO mice (FIGS. 5A-5B).

To demonstrate that thrombin cleavage of OPN was important in other cancers, an ovarian carcinoma model was used in which Id8 cells (ovarian carcinoma) were injected interperitoneally. The mice were weighed as an increase in weight represents growth of the tumor. Growth of Id8 ovarian carcinoma tumors in OPN-KI mice was significantly reduced compared to that in WT mice.

Our data provides the first demonstration of the importance of thrombin cleavage of OPN in cancer biology. The OPN KI mice demonstrated diminished B16 tumor growth equal to the absence of OPN, indicating that thrombin cleavage of the host OPN plays a critical role in melanoma growth in vivo. In addition, Id8 ovarian carcinoma growth was suppressed in OPN KI mice versus WT mice. Treatment with the thrombin inhibitor, dabigatran etexilate, reduced the growth of B16 melanomas in both the subcutaneous implant and metastasis models to a level similar to that observed in mice lacking OPN or in mice with OPN that could not be cleaved by thrombin.

Example 2

Therapeutic Monoclonal Antibodies

Results from the melanoma and ovarian carcinoma studies (Example 1) using the OPN-KI mice indicate that blockade of OPN cleavage and/or blocking of OPN fragments has potential for therapeutic intervention in melanoma and other cancers. Monoclonal antibodies in different formats (mAB, bispecific, trispecific, nanobody etc.) are generated against the following targets:

OPN-FL: Antibody blocking Cleavage of OPN:
  Antibodies against SVVGLR (SEQ ID NO:1) or SKSKKF (SEQ ID NO:2) in human OPN or the OPN sequences that bind to the thrombin anion binding exosites 1 and 2.
OPN-R: Antibody blocking Integrin binding to OPN-R using antibodies against the exposed SVVYGLR (SEQ ID NO:3) in human OPN
OPN-CTF: Antibody blocking the SKSKKFRR (SEQ ID NO:4) sequences in human OPN blocking CTF multimerization Applications:

Melanoma and other cancers may be treated with the antibodies either as a monotherapy or in combination with a standard therapy. Therapeutic benefit is obtained by the generation of monoclonal antibodies for functional blocking of the OPN thrombin cleavage site (SVVYGLRSKSKKF, SEQ ID NO:9), the OPN-R SVVYGLR (SEQ ID NO:3) integrin binding motif, and the OPN-CTF region SKSKKFRRPD (SEQ ID NO:10), which is implicated in CTF multimerization in cancer. Antibodies targeted to the binding sites of OPN on thrombin, exosites 1 and 2, may also be useful to reduce OPN cleavage by thrombin. Peptides that specifically bind thrombin binding exosites 1 and 2, but do not interfere with thrombin procoagulant activity, may also be useful.

The antibodies are useful in achieving the beneficial effects of prevention of OPN cleavage without the side-effects of the bleeding risk if a thrombin inhibitor or other anticoagulant is used.

Example 3

Production of Monoclonal Antibodies that Inhibit Thrombin Cleavage of Osteopontin Our goal was to identify monoclonal antibodies (Mabs) that bind to full-length osteopontin (OPN-FL) and block its cleavage by thrombin. FIG. 7 shows an alignment of the OPN protein sequences around the thrombin cleavage site from rabbit, rat, mouse, human, rhesus macaque, cynomolgus, and pig. The peptide antigen, YGLRSKS (SEQ ID NO:11, amino acid in bold is cleaved by thrombin), covalently bound to keyhole limpet hemocyanin (KLH), was used to raise antibodies in rabbits in order to develop rabbit monoclonal antibodies. The peptide antigen was modified with polyethylene glycol to increase solubility and a 6-aminohexanoic acid (Ahx) linker with a C-terminal Cys linked by the Ahx $(PEG)_3$-YGLRSKS-Ahx-C). Rabbits were chosen because their OPN sequence around the thrombin cleavage site is different from the mouse and human sequence: YRLKRSKS (SEQ ID NO:47, amino acid in bold is cleaved by thrombin). Cells producing antibodies that bound to the peptide antigen had their heavy and light chain cDNA cloned and inserted into expression vectors that express rabbit IgG. Those expression vectors were then transfected into HEK293F cells and the medium assayed. Antibody screening was then used to identify clones producing antibodies reacting with mouse, rat and human OPN.

The rabbit monoclonal clones were screened using a direct ELISA against the OPN antigen peptide (FIG. 8). 35 positives (shown) were identified. For the assay to identify clones producing anti-OPN IgG, 96 well plates were coated with 2 µg/mL avidin overnight before addition of the OPN antigen peptide labeled with biotin for 30 minutes. Then supernatants from the clones were diluted 1:50 before detection with an anti-Rabbit IgG Fc labeled with horse radish peroxidase (HRP) diluted $10^3$ times. Substrate for HRP was added and color was measured.

To determine the concentration of the IgG in the clone supernatants, 96 well plates were coated with 2 µg/mL anti-rabbit IgG overnight. Then supernatants from the clones were diluted 1:50 before detection with an anti-Rabbit IgG Fc labeled with horse radish peroxidase (HRP) diluted $10^3$ times. Substrate for HRP was added and color was measured. The concentration of IgG in the clone supernatants was calculated from a standard dilution curve of rabbit IgG.

Figure 10:
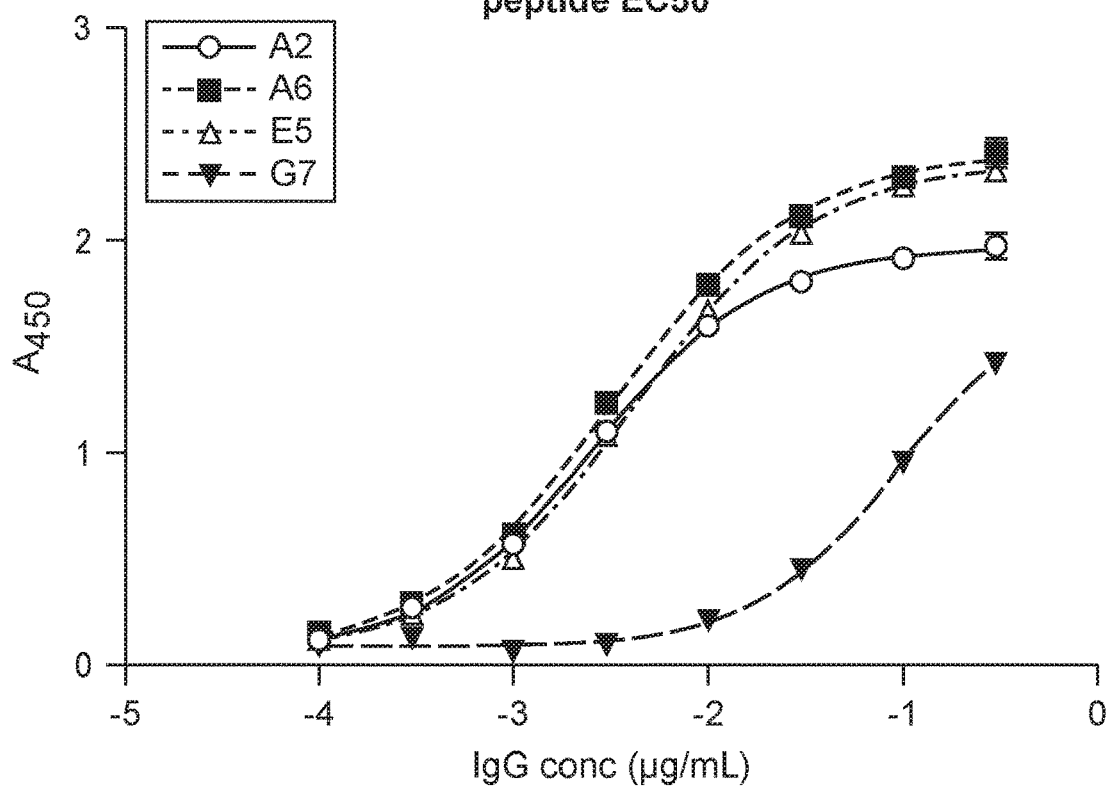
FIG. 10 shows the determination of $EC_{50}$ for the four clones in the peptide antigen binding assay. To determine $EC_{50}$ for purified anti-OPN IgG, 96 well plates were coated with 2 ug/mL avidin overnight before addition of the OPN antigen peptide labeled with biotin for 30 minutes. Then IgG in the supernatants from the selected clones was purified by binding to protein A/G Sepharose beads and elution. The purified IgG was serially then diluted before detection with an anti-Rabbit IgG Fc labeled with horse radish peroxidase (HRP) diluted $10^3$ times. Substrate for HRP was added and color was measured.

FIG. 9 shows the results of screening the rabbit monoclonal antibodies in a direct ELISA against the antigen peptide, mouse OPN-FL, and human OPN-FL. Clones were identified that bound OPN-FL from human or mouse. Four clones (A2, A6, E5, and G7) were selected for further investigation. The $EC_{50}$ was determined for these four clones in the peptide antigen binding assay (FIG. 10). To determine the $EC_{50}$ for the purified anti-OPN IgG, 96 well plates were coated with 2 µg/mL avidin overnight before addition of the OPN antigen peptide labeled with biotin for 30 minutes. Then, IgG in the supernatants from the selected clones was purified by binding to protein A/G Sepharose beads and elution. The purified IgG was serially diluted before detection with an anti-Rabbit IgG Fc labeled with horse radish peroxidase (HRP) diluted $10^3$ times. The substrate for HRP was added and color was measured.

Figure 11:
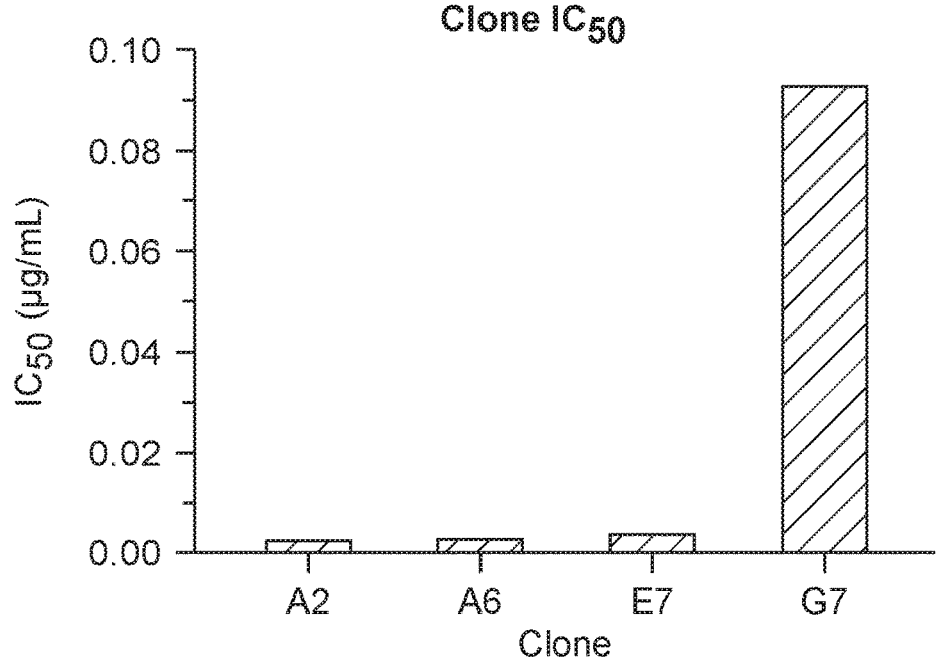
FIG. 11 shows the $EC_{50}$ values for the four clones for binding to the OPN antigen peptide. Based on the data from FIG. 4, $EC_{50}$ values were calculated from the 4-parameter fit equation using Prism Graphpad using the data from FIG. 10. A2=2.6 ng/mL, A6=3.2 ng/mL; E5=4.0 ng/mL and G7=93.2 ng/mL.

FIG. 11 shows the $EC_{50}$ values for the four clones for binding to the OPN antigen peptide. Based on the data from FIG. 10, the $EC_{50}$ values were calculated from a 4 parameter fit equation using Prism Graphpad. The $EC_{50}$ values were 2.6 ng/mL for the A2 clone, 3.2 ng/mL for the A6 clone; 4.0 ng/mL for the E5 clone, and 93.2 ng/mL for the G7 clone.

Figure 12:
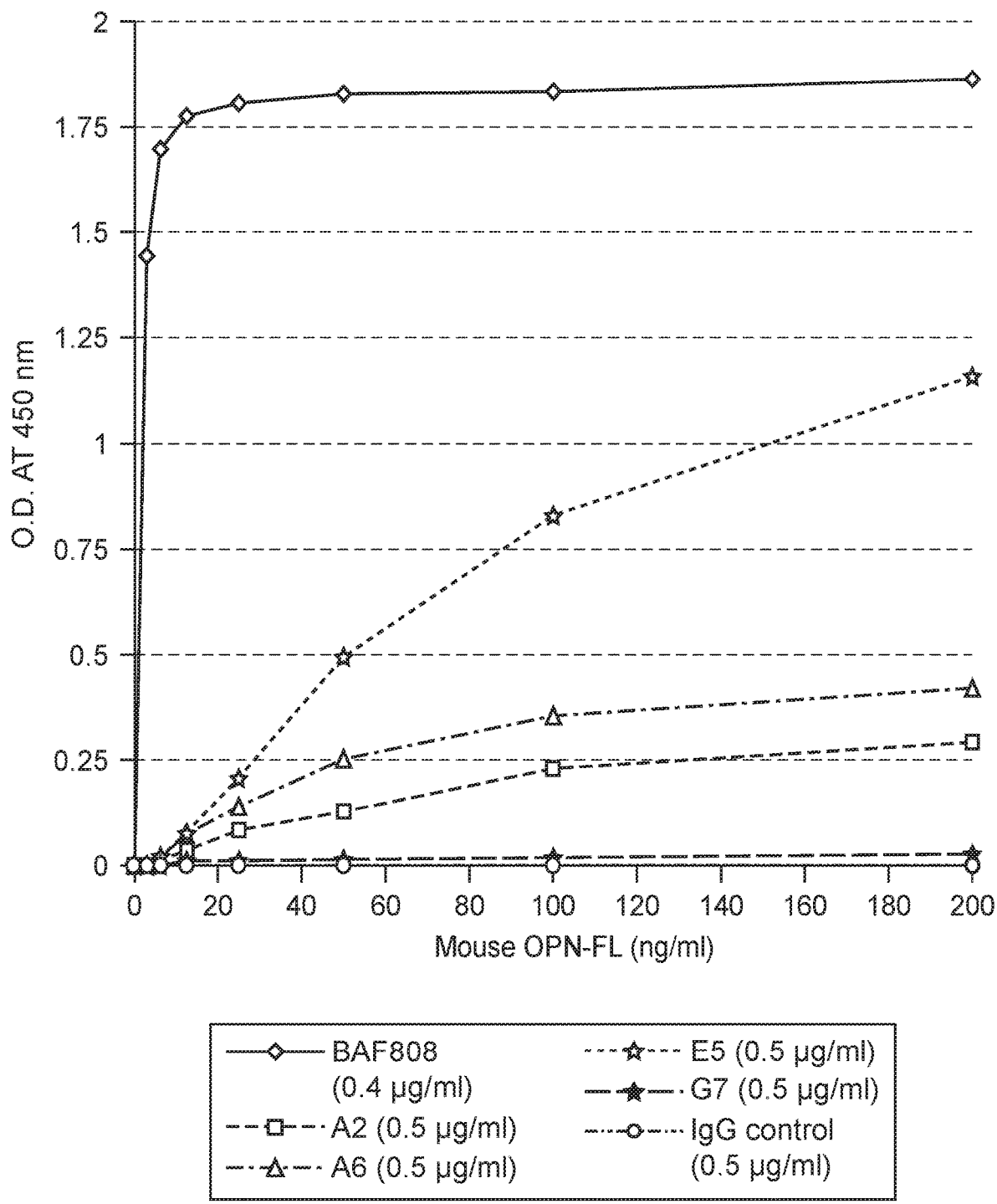
FIG. 12 shows the determination of $EC_{50}$ values for the four clones in the direct binding ELISA against mouse OPN-FL. Clones A2, A6 and E5 bind to mouse OPN-FL. A goat polyclonal anti-mouse osteopontin IgG (2 µg/ml) (R&D Systems, Minneapolis, MN) in PBS buffer was coated onto 96-well ELISA plates, and nonspecific binding sites were blocked with 1% BSA in PBS for 1 hr. The recombinant mouse osteopontin protein (R&D Systems, Minneapolis, MN) was diluted with 1% BSA in PBS (starting from 200 ng/ml and diluted down) and incubated for 2 hrs. After washing with 0.05% Tween 20 in PBS, samples were incubated with purified antibodies A2, A6, E5, G7 or IgG control (500 ng/ml) in PBS with 1% BSA for 1 hr. After washing with 0.05% Tween 20 in PBS, the samples were incubated with peroxidase-conjugated goat anti-rabbit IgG antibody (100 ng/ml) in PBS with 1% BSA for 1 hr. After washing, tetramethylbenzidine substrate was incubated for 10 min followed by the addition of Stop Solution and measurement of absorbance at 450 nm.

The $EC_{50}$ values for the four clones in a direct binding ELISA against mouse OPN-FL was determined (FIG. 12), and all of the clones, including A2, A6 and E5 were found to bind to the mouse OPN-FL. A goat polyclonal anti-mouse osteopontin IgG (2 µg/ml) (R&D Systems, Minneapolis, MN) in PBS buffer was coated onto 96-well ELISA plates, and nonspecific binding sites were blocked with 1% BSA in PBS for 1 hr. Recombinant mouse osteopontin proteins (R&D Systems, Minneapolis, MN) were diluted with 1% BSA in PBS (starting from 200 ng/ml and diluted down) and incubated for 2 hrs. After washing with 0.05% Tween 20 in PBS, samples were incubated with purified antibodies A2, A6, E5, G7 or IgG control (500 ng/ml) in PBS with 1% BSA for 1 hr. After washing with 0.05% Tween 20 in PBS, the samples were incubated with peroxidase-conjugated goat anti-rabbit IgG antibody (100 ng/ml) in PBS with 1% BSA for 1 hr. After washing, tetramethylbenzidine substrate was incubated for 10 min followed by the addition of Stop Solution and measurement of absorbance at 450 nm.

Figure 13:
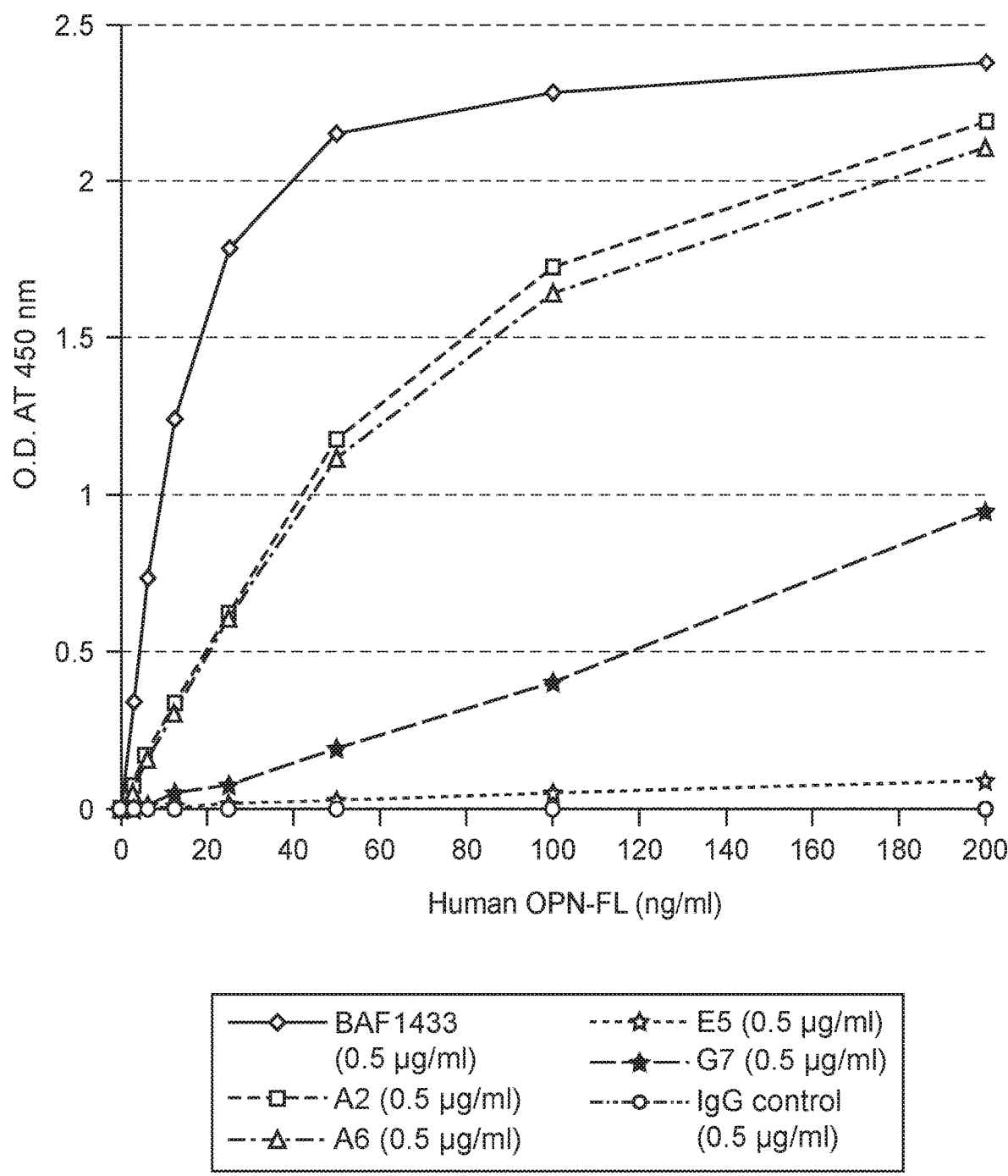
FIG. 13 shows the determination of $EC_{50}$ values for the four selected clones in the direct binding ELISA against human OPN-FL. All four clones bind to human OPN-FL. A mouse monoclonal anti-human osteopontin antibody (4 µg/ml) (R&D Systems, Minneapolis, MN) in PBS buffer was coated onto 96-well ELISA plates, and nonspecific binding sites were blocked with 1% BSA in PBS for 1 hr. Recombinant human osteopontin proteins (GST-OPN-his, purified in house) were diluted with 1% BSA in PBS (starting from 200 ng/ml and diluted down) and incubated for 2 hrs. After washing with 0.05% Tween 20 in PBS, samples were incubated with purified antibodies A2, A6, E5, G7 or IgG control (500 ng/ml) in PBS with 1% BSA for 1 hr. After washing with 0.05% Tween 20 in PBS, the samples were incubated with peroxidase-conjugated goat anti-rabbit IgG antibody (100 ng/ml) in PBS with 1% BSA for 1 hr. After washing, tetramethylbenzidine substrate was incubated for 10 min followed by the addition of Stop Solution and measurement of absorbance at 450 nm.

In addition, the $EC_{50}$ values for the four clones in a direct binding ELISA against human OPN-FL was determined, and all four clones were found to bind to the human OPN-FL (FIG. 13. A mouse monoclonal anti-human osteopontin antibody (4 µg/ml) (R&D Systems, Minneapolis, MN) in PBS buffer was coated onto 96-well ELISA plates, and nonspecific binding sites were blocked with 1% BSA in PBS for 1 hr. Recombinant human osteopontin proteins (GST-OPN-his, purified in house) were diluted with 1% BSA in PBS (starting from 200 ng/ml and diluted down) and incubated for 2 hrs. After washing with 0.05% Tween 20 in PBS, samples were incubated with purified antibodies A2, A6, E5, G7 or IgG control (500 ng/ml) in PBS with 1% BSA for 1 hr. After washing with 0.05% Tween 20 in PBS, the samples were incubated with peroxidase-conjugated goat anti-rabbit IgG antibody (100 ng/ml) in PBS with 1% BSA for 1 hr. After washing, tetramethylbenzidine substrate was incubated for 10 min followed by the addition of Stop Solution and measurement of absorbance at 450 nm.

Figure 14:
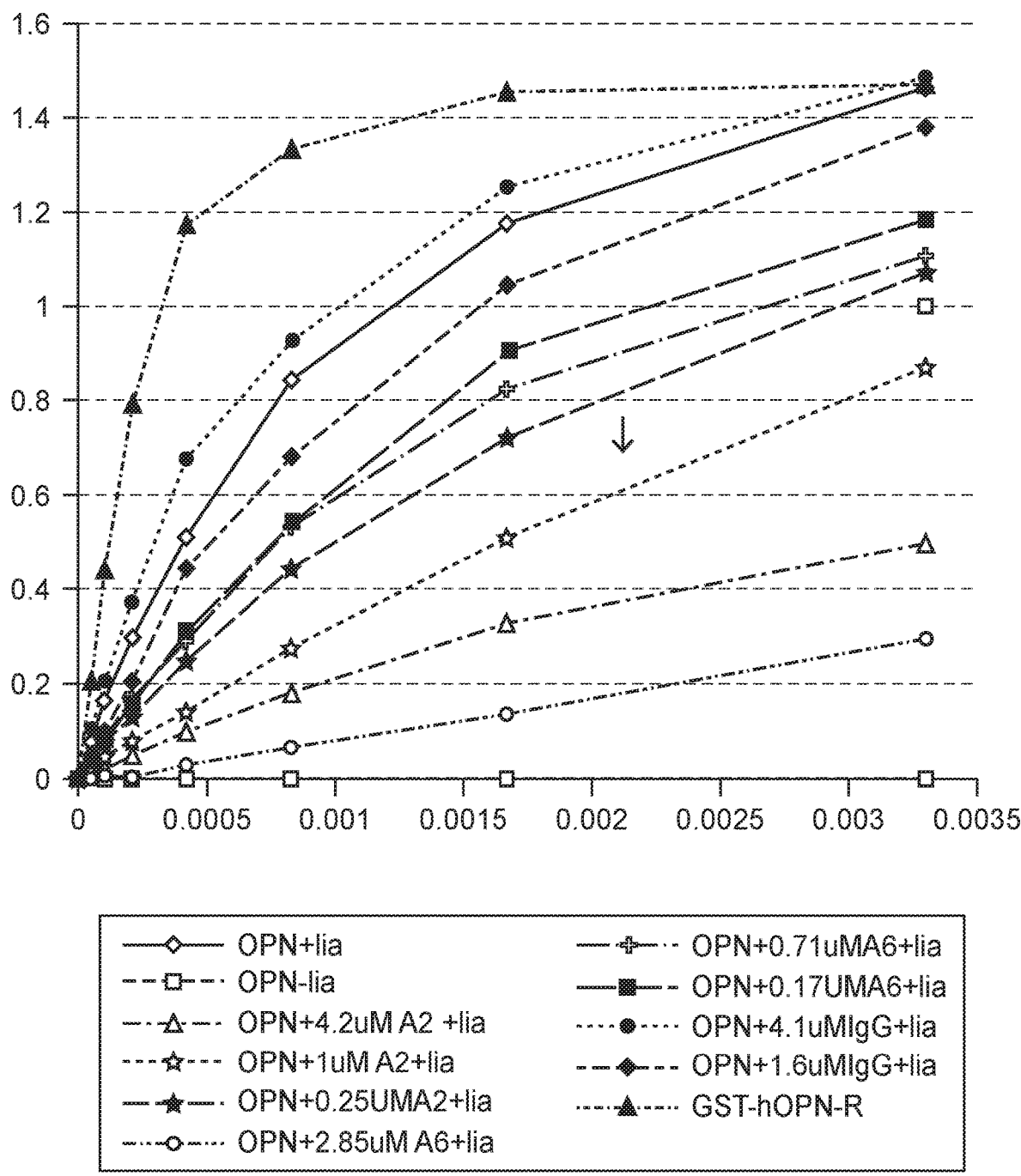
FIG. 14 shows the determination of inhibition of thrombin cleavage of human OPN-FL for the four clones by determining generation of one of the cleavage products, OPN-R, in a specific ELISA for OPN-R. All four clones inhibit thrombin cleavage of human OPN-FL. Recombinant human osteopontin protein (purified as described in Myles T. et al. (2003) J Biol Chem. 278(51):51059-51067; herein incorporated by reference) at 3.2 µM was incubated with or without purified antibodies A2, A6, E5, G7 or IgG control (concentration as indicated on data) at room temperature for 20 min. Human Thrombin (32 nM) (R&D Systems) was added to the samples and incubated at 37° C. for 10 min, followed by addition of PPACK to 4.8 µM. Samples were diluted 1/300 with 1% BSA in PBS and the OPN-R generated was measured by OPN-R specific ELISA. Human OPN-R ELISA: A mouse monoclonal anti-human osteopontin antibody (4 µg/ml) (R&D Systems, Minneapolis, MN) in PBS buffer was coated onto 96-well ELISA plates, and nonspecific binding sites were blocked with 1% BSA in PBS for 1 hr. Recombinant human OPN-R protein with a glutathione S-transferase tag (GST-OPN-R, Myles et al. (2003), supra) was diluted with 1% BSA in PBS (starting from 200 ng/ml and diluted down) as a calibration standard. The standard and samples of thrombin cleavage products (starting with 1/300 dilution and diluted further down) were incubated for 2 hrs. After washing with 0.05% Tween 20 in PBS, the samples were incubated with Biotinylated rabbit polyclonal anti-OPN-R antibody (500 ng/ml) (Sharif et al, 2009 A+R) in PBS with 1% BSA for 1 hr. After washing, the samples were incubated with peroxidase-conjugated streptavidin (100 ng/ml) in PBS with 1% BSA for 1 hr. After washing, tetramethylbenzidine substrate was incubated for 10 min followed by the addition of Stop Solution and measurement of absorbance at 450 nm. The amount of OPN-R generated in each sample was calculated from the OPN-R standard in the OPN-R ELISA and then the inhibition of thrombin cleavage of each antibody clone at different concentrations in comparison with the control without antibody was calculated and graphed.

Next, the ability of the monoclonal antibodies from the four clones to inhibit thrombin cleavage of human OPN-FL was determined by detecting inhibition of the generation of one of the cleavage products, OPN-R, in a specific ELISA for OPN-R. All four clones were found to inhibit thrombin cleavage of human OPN-FL (FIG. 14). Recombinant human osteopontin protein (3.2 µM, purified in house) was incubated with or without purified antibodies A2, A6, E5, G7 or IgG control at room temperature for 20 min. Human thrombin (32 nM) (R&D Systems) was added to the samples and incubated at 37° C. for 10 min, followed by addition of PPACK to 4.8 µM. Samples were diluted 1/300 with 1% BSA in PBS and the OPN-R generated was measured by OPN-R specific ELISA.

Figure 15:
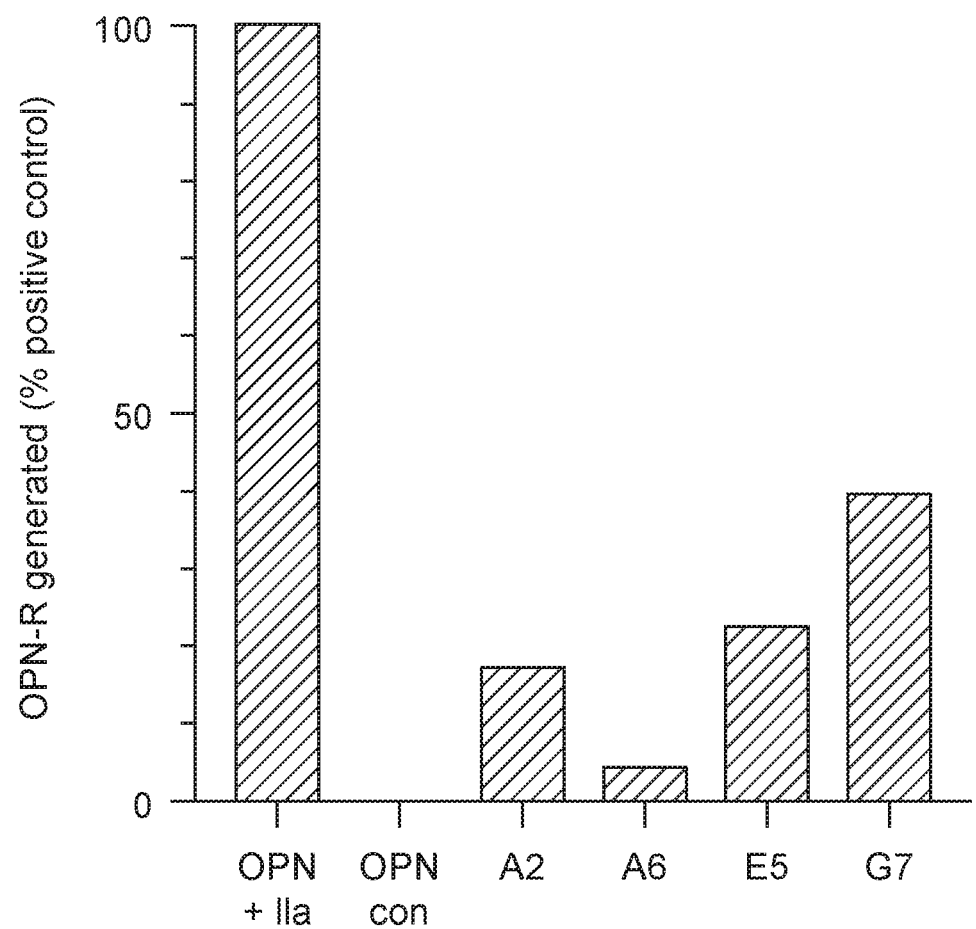
FIG. 15 shows the % inhibition for the four clones in inhibiting the cleavage of human OPN-FL based on the data from FIG. 14. A2=82%; A6=95.4%; E5=77.2% and G7=60.1%

Human OPN-R ELISA:

A mouse monoclonal anti-human osteopontin antibody (4 µg/ml) (R&D Systems, Minneapolis, MN) in PBS buffer was coated onto 96-well ELISA plates, and nonspecific binding sites were blocked with 1% BSA in PBS for 1 hr. Recombinant human OPN-R protein (GST-OPN-R, Myles et al, 2003 JBC)) was diluted with 1% BSA in PBS (starting from 200 ng/ml and diluted down) as standard. Standard and samples of thrombin cleavage products (starting with 1/300 dilution and diluted further down) were incubated for 2 hrs. After washing with 0.05% Tween 20 in PBS, the samples were incubated with biotinylated rabbit polyclonal anti-OPN-R antibody (500 ng/ml) (Sharif et al, 2009 A+R) in PBS with 1% BSA for 1 hr. After washing, the samples were incubated with peroxidase-conjugated streptavidin (100 ng/ml) in PBS with 1% BSA for 1 hr. After washing, tetramethylbenzidine substrate was incubated for 10 min followed by the addition of Stop Solution and measurement of absorbance at 450 nm. The amount of OPN-R generated in each sample was calculated from the OPN-R standard in the OPN-R ELISA and then the inhibition of thrombin cleavage of each antibody clone at different concentration was calculated and graphed. FIG. 15 shows the % inhibition for the four clones in inhibiting the cleavage of human OPN-FL: 82% for A2; 95.4% for A6; 77.2% for E5, and 60.1% for G7.

Figure 16:
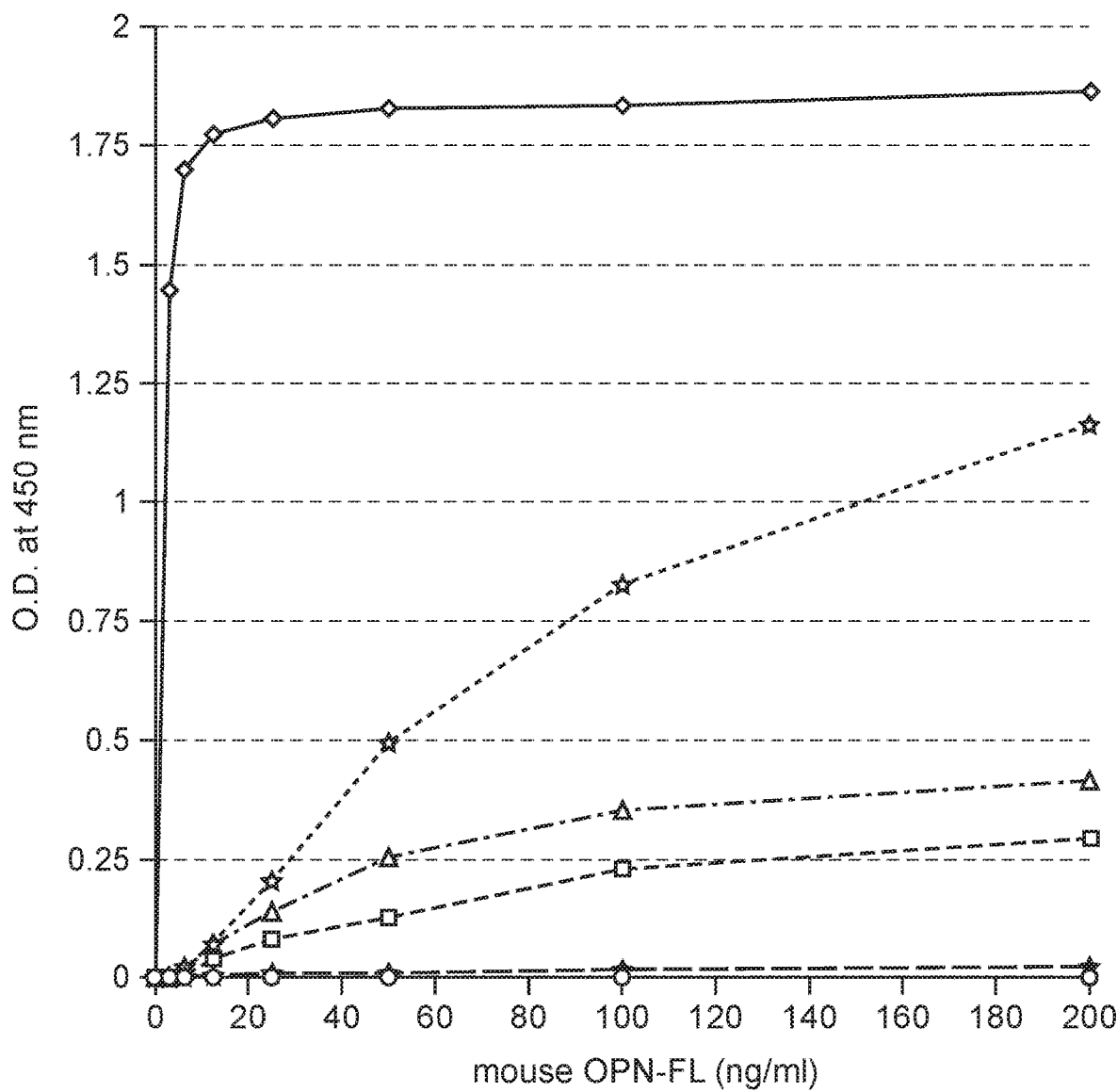
FIG. 16 shows the determination of inhibition of thrombin cleavage of mouse OPN-FL for the four clones by determining generation of one of the cleavage products, OPN-R, in a specific ELISA for OPN-R. All four clones inhibit thrombin cleavage of mouse OPN-FL. Recombinant mouse osteopontin protein (R&D systems) (2 µM) were incubated with or without purified antibodies A2, A6, E5, G7 or IgG control (2 µM) at room temperature for 20 min. Human Thrombin (20 nM) (R&D Systems) was added to the samples and incubated at 37° C. for 10 min, followed by addition of PPACK to 4.7 µM. Samples were diluted 1/100 or 1/30 with 1% BSA in PBS and the OPN-R generated was measured by the mouse OPN-R-specific ELISA. The amount of OPN-R generated in each sample was calculated from the OPN-R standard in the OPN-R ELISA and then the inhibition of thrombin cleavage of each antibody clone at different concentration was calculated and graphed.

We also evaluated the inhibition of thrombin cleavage of the mouse OPN-FL for the four clones by determining the generation of one of the cleavage products, OPN-R, in a specific ELISA for OPN-R. All four clones were found to inhibit thrombin cleavage of mouse OPN-FL (FIG. 16). Recombinant mouse osteopontin protein (R&D systems) (2 μM) were incubated with or without purified antibodies A2, A6, E5, G7 or IgG control (2 μM) at room temperature for 20 min. Human Thrombin (20 nM) (R&D Systems) was added to the samples and incubated at 37° C. for 10 min, followed by addition of PPACK to 4.7 μM. Samples were diluted 1/100 or 1/30 with 1% BSA in PBS and the OPN-R generated was measured by OPN-R specific ELISA.

Mouse OPN-R ELISA:

A goat polyclonal anti-mouse osteopontin IgG (4 μg/ml) (R&D Systems, Minneapolis, MN) in PBS buffer was coated onto 96-well ELISA plates, and nonspecific binding sites were blocked with 1% BSA in PBS for 1 hr. Samples of thrombin cleavage products (starting with 1/30 or 1/100 dilution and diluted further down) were incubated for 2 hrs. After washing with 0.05% Tween 20 in PBS, the samples were incubated with biotinylated rabbit polyclonal anti-OPN-R antibody (2 μg/ml) (Sharif et al 2009 A+R) in PBS with 1% BSA for 1 hr. After washing, the samples were incubated with peroxidase-conjugated streptavidin (100 ng/ml) in PBS with 1% BSA for 1 hr. After washing, tetramethylbenzidine substrate was incubated for 10 min followed by the addition of Stop Solution and measurement of absorbance at 450 nm. The amount of OPN-R generated in each sample was calculated from the OPN-R standard in the OPN-R ELISA and then the inhibition of thrombin cleavage of each antibody clone at different concentration was calculated and graphed.

The clones were sequenced. The amino acid sequences of the heavy and light chains of the A2, A6, E5, and G7 monoclonal antibodies and the nucleic acid sequences encoding them as well as the sequences of their CDRs were determined and are shown in SEQ ID NOS:13-46 of the Sequence Listing.

What is claimed is:

1. An isolated antibody or an antigen-binding fragment thereof that specifically binds to osteopontin or a thrombin cleavage fragment thereof, wherein the antibody or antigen-binding fragment thereof inhibits thrombin cleavage of osteopontin or integrin binding to the thrombin cleavage fragment of osteopontin, wherein the antibody or antigen-binding fragment thereof comprises a heavy chain complementarity-determining region 1 (CDR-H1) comprising the amino acid sequence of SEQ ID NO: 29; a heavy chain complementarity-determining region 2 (CDR-H2) comprising the amino acid sequence of SEQ ID NO:30; a heavy chain complementarity-determining region 3 (CDR-H3) comprising the amino acid sequence of SEQ ID NO:31; a light chain complementarity-determining region 1 (CDR-L1) comprising the amino acid sequence of SEQ ID NO:32; a light chain complementarity-determining region 2 (CDR-L2) comprising the amino acid sequence of SEQ ID NO:33; and a light chain complementarity-determining region 3 (CDR-L3) comprising the amino acid sequence of SEQ ID NO:34;

wherein the antibody or antigen-binding fragment thereof comprises a heavy chain complementarity-determining region 1 (CDR-H1) comprising the amino acid sequence of SEQ ID NO: 35; a heavy chain complementarity-determining region 2 (CDR-H2) comprising the amino acid sequence of SEQ ID NO:36; a heavy chain complementarity-determining region 3 (CDR-H3) comprising the amino acid sequence of SEQ ID NO:37; a light chain complementarity-determining region 1 (CDR-L1) comprising the amino acid sequence of SEQ ID NO:38; a light chain complementarity-determining region 2 (CDR-L2) comprising the amino acid sequence of SEQ ID NO:39; and a light chain complementarity-determining region 3 (CDR-L3) comprising the amino acid sequence of SEQ ID NO:40; or wherein the antibody or antigen-binding fragment thereof comprises a heavy chain complementarity-determining region 1 (CDR-H1) comprising the amino acid sequence of SEQ ID NO: 41; a heavy chain complementarity-determining region 2 (CDR-H2) comprising the amino acid sequence of SEQ ID NO:42; a heavy chain complementarity-determining region 3 (CDR-H3) comprising the amino acid sequence of SEQ ID NO:43; a light chain complementarity-determining region 1 (CDR-L1) comprising the amino acid sequence of SEQ ID NO:44; a light chain complementarity-determining region 2 (CDR-L2) comprising the amino acid sequence of SEQ ID NO:45; and a light chain complementarity-determining region 3 (CDR-L3) comprising the amino acid sequence of SEQ ID NO:46.

2. The antibody or antigen-binding fragment thereof of claim 1, wherein the antibody or antigen-binding fragment thereof comprises:
   a) a heavy chain comprising the amino acid sequence of SEQ ID NO:14 or SEQ ID NO:18, or a sequence having at least 80% identity to the amino acid sequence of SEQ ID NO:14 or SEQ ID NO:18; and
   b) a light chain comprising the amino acid sequence of SEQ ID NO:16 or SEQ ID NO:20, or a sequence having at least 80% identity to the amino acid sequence of SEQ ID NO:16 or SEQ ID NO:20.

3. The antibody or antigen-binding fragment thereof of claim 1, wherein the antibody or antigen-binding fragment thereof comprises:
   a) a heavy chain comprising the amino acid sequence of SEQ ID NO:22, or a sequence having at least 80% identity to the amino acid sequence of SEQ ID NO:22; and
   b) a light chain comprising the amino acid sequence of SEQ ID NO:24 or a sequence having at least 80% identity to the amino acid sequence of SEQ ID NO:24.

4. The antibody or antigen-binding fragment thereof of claim 1, wherein the antibody or antigen-binding fragment thereof comprises:
   a) a heavy chain comprising the amino acid sequence of SEQ ID NO:26, or a sequence having at least 80% identity to the amino acid sequence of SEQ ID NO:26; and
   b) a light chain comprising the amino acid sequence of SEQ ID NO:28, or a sequence having at least 80% identity to the amino acid sequence of SEQ ID NO:28.

5. The antibody or antigen-binding fragment thereof of claim 1, wherein the antibody is selected from the group consisting of a monoclonal antibody, a polyclonal antibody, a chimeric antibody, a humanized antibody, a nanobody, a Fab fragment, a Fab' fragment, a F(ab')$_2$ fragment, a F$_v$ fragment, and a scFv fragment.

6. A composition comprising the antibody or antigen-binding fragment thereof of claim 1 and a pharmaceutically acceptable excipient or carrier.

7. The composition of claim 6, further comprising a B-Raf inhibitor, a mitogen-activated protein kinase (MEK) inhibitor, or a combination thereof.

8. A method for treating an osteopontin-associated disorder, the method comprising administering to a subject in need thereof a therapeutically effective amount of the composition of claim 6.

9. The method of claim 8, wherein the antibody is a humanized antibody.

10. The method of claim 8, further comprising administering at least one additional anti-cancer therapeutic agent.

11. The method of claim 10, wherein the anti-cancer therapeutic agent is selected from the group consisting of a chemotherapeutic agent, an immunotherapeutic agent, a biologic therapeutic agent, a pro-apoptotic agent, an angiogenesis inhibitor, a photoactive agent, a radiosensitizing agent, and a radioisotope.

12. The method of claim 8, wherein the osteopontin-associated disorder is inflammation or a cancer associated with overexpression of osteopontin.

13. The method of claim 8, wherein the osteopontin-associated disorder is cardiac hypertrophy, myocardial fibrosis, melanoma, glioblastoma, ovarian cancer, breast cancer, or lung cancer.

14. The method of claim 12, further comprising administering a B-Raf inhibitor, a mitogen-activated protein kinase (MEK) inhibitor, or a combination thereof.

15. The method of claim 13, wherein the B-Raf inhibitor is selected from the group consisting of dabrafenib, vemurafenib, sorafenib, LGX818, GDC-0879, and PLX-4720.

16. The method of claim 13, wherein the MEK inhibitor is selected from the group consisting of trametinib, cobimetinib, binimetinib, selumetinib, and PD-325901.

17. A method for inhibiting growth and/or proliferation of tumor cells in a subject comprising administering to the subject an effective amount of the antibody or antigen-binding fragment thereof of claim 1.

18. A conjugate comprising the antibody or antigen-binding fragment thereof of claim 1 and an agent selected from the group consisting of an anti-cancer therapeutic agent, a detectable label, and an imaging agent.

19. The conjugate of claim 18, wherein the anti-cancer therapeutic agent is selected from the group consisting of a cytotoxic agent, a drug, a toxin, a nuclease, a hormone, an immunomodulator, a pro-apoptotic agent, an anti-angiogenic agent, a boron compound, a photoactive agent, and a radioisotope.

* * * * *

SEQUENCE LISTING

```
<160> NUMBER OF SEQ ID NOS: 47

<210> SEQ ID NO 1
<211> LENGTH: 6
<212> TYPE: PRT
<213> ORGANISM: Artificial Sequence
<220> FEATURE:
<223> OTHER INFORMATION: osteopontin epitope

<400> SEQUENCE: 1

Ser Val Val Gly Leu Arg
1               5

<210> SEQ ID NO 2
<211> LENGTH: 6
<212> TYPE: PRT
<213> ORGANISM: Artificial Sequence
<220> FEATURE:
<223> OTHER INFORMATION: osteopontin epitope

<400> SEQUENCE: 2

Ser Lys Ser Lys Lys Phe
1               5

<210> SEQ ID NO 3
<211> LENGTH: 7
<212> TYPE: PRT
<213> ORGANISM: Artificial Sequence
<220> FEATURE:
<223> OTHER INFORMATION: osteopontin epitope

<400> SEQUENCE: 3

Ser Val Val Tyr Gly Leu Arg
1               5
```

<210> SEQ ID NO 4
<211> LENGTH: 8
<212> TYPE: PRT
<213> ORGANISM: Artificial Sequence
<220> FEATURE:
<223> OTHER INFORMATION: osteopontin epitope

<400> SEQUENCE: 4

Ser Lys Ser Lys Lys Phe Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: immunogenic peptide

<400> SEQUENCE: 5

Ser Leu Ala Tyr Gly Leu Arg
1               5

<210> SEQ ID NO 6
<211> LENGTH: 16
<212> TYPE: PRT
<213> ORGANISM: Artificial Sequence
<220> FEATURE:
<223> OTHER INFORMATION: immunogenic peptide

<400> SEQUENCE: 6

Ser Leu Ala Tyr Gly Leu Arg Ser Lys Ser Arg Ser Phe Gln Val Ser
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: immunogenic peptide

<400> SEQUENCE: 7

Ser Lys Ser Arg Ser Phe Gln Val Ser
1               5

<210> SEQ ID NO 8
<211> LENGTH: 314
<212> TYPE: PRT
<213> ORGANISM: Homo sapiens
<300> PUBLICATION INFORMATION:
<308> DATABASE ACCESSION NUMBER: NCBI/NP_001035147
<309> DATABASE ENTRY DATE: 2019-06-18
<313> RELEVANT RESIDUES IN SEQ ID NO: (1)..(314)

<400> SEQUENCE: 8

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

```
Ser His Asp His Met Asp Asp Met Asp Asp Glu Asp Asp Asp His
             85                  90                  95

Val Asp Ser Gln Asp Ser Ile Asp Ser Asn Asp Ser Asp Val Asp
            100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
            130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
        210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
                260                 265                 270

Phe His Ser His Glu Phe His Ser His Glu Asp Met Leu Val Val Asp
            275                 280                 285

Pro Lys Ser Lys Glu Glu Asp Lys His Leu Lys Phe Arg Ile Ser His
        290                 295                 300

Glu Leu Asp Ser Ala Ser Ser Glu Val Asn
305                 310

<210> SEQ ID NO 9
<211> LENGTH: 13
<212> TYPE: PRT
<213> ORGANISM: Artificial Sequence
<220> FEATURE:
<223> OTHER INFORMATION: osteopontin thrombin cleavage site

<400> SEQUENCE: 9

Ser Val Val Tyr Gly Leu Arg Ser Lys Ser Lys Lys Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: OPN-CTF region

<400> SEQUENCE: 10

Ser Lys Ser Lys Lys Phe Arg Arg Pro Asp
1               5                   10

<210> SEQ ID NO 11
<211> LENGTH: 7
<212> TYPE: PRT
<213> ORGANISM: Artificial Sequence
<220> FEATURE:
<223> OTHER INFORMATION: immunogenic peptide
```

<400> SEQUENCE: 11

Tyr Gly Leu Arg Ser Lys Ser
1               5

<210> SEQ ID NO 12

<400> SEQUENCE: 12

000

<210> SEQ ID NO 13
<211> LENGTH: 1386
<212> TYPE: DNA
<213> ORGANISM: Artificial Sequence
<220> FEATURE:
<223> OTHER INFORMATION: clone encoding A2 monoclonal antibody heavy
      chain 3
<220> FEATURE:
<221> NAME/KEY: CDS
<222> LOCATION: (1)..(1383)

<400> SEQUENCE: 13

| | | |
|---|---|---|
| atg gag act ggg ctg cgc tgg ctt ctc ctg gtc gct gtg ctc aaa ggt<br>Met Glu Thr Gly Leu Arg Trp Leu Leu Leu Val Ala Val Leu Lys Gly<br>1               5                   10                  15 | | 48 |
| gtc cag tgt cag tcg gtg aag gag tcc gag gga ggt ctc ttc aag cca<br>Val Gln Cys Gln Ser Val Lys Glu Ser Glu Gly Gly Leu Phe Lys Pro<br>            20                  25                  30 | | 96 |
| acg gat acc ctg aca ctc acc tgc aaa gcc tct gga ttc acc gtc agt<br>Thr Asp Thr Leu Thr Leu Thr Cys Lys Ala Ser Gly Phe Thr Val Ser<br>        35                  40                  45 | | 144 |
| agt tac gac atg ggc tgg ctc cgc cag gct cca ggg aac ggg ctt gaa<br>Ser Tyr Asp Met Gly Trp Leu Arg Gln Ala Pro Gly Asn Gly Leu Glu<br>    50                  55                  60 | | 192 |
| tct atc gga gcc att ggt agt gat ggt agt gag tac tat gtg agc tgg<br>Ser Ile Gly Ala Ile Gly Ser Asp Gly Ser Glu Tyr Tyr Val Ser Trp<br>65                  70                  75                  80 | | 240 |
| gcg aga ggc cga acc gcc atc acc aga aac acc aac cag aac acg gtg<br>Ala Arg Gly Arg Thr Ala Ile Thr Arg Asn Thr Asn Gln Asn Thr Val<br>                85                  90                  95 | | 288 |
| act ctg aaa atg acc agt ctg aca gcc gcg gac acg gcc acc tat ttc<br>Thr Leu Lys Met Thr Ser Leu Thr Ala Ala Asp Thr Ala Thr Tyr Phe<br>            100                 105                 110 | | 336 |
| tgt gcg aga gac tca cac tat agc tat ggc tat gat tat gat atc tgg<br>Cys Ala Arg Asp Ser His Tyr Ser Tyr Gly Tyr Asp Tyr Asp Ile Trp<br>        115                 120                 125 | | 384 |
| ggc cca ggc acc ctg gtc acc gtc tcc tca ggg caa cct aag gct cca<br>Gly Pro Gly Thr Leu Val Thr Val Ser Ser Gly Gln Pro Lys Ala Pro<br>    130                 135                 140 | | 432 |
| tca gtc ttc cca ctg gcc ccc tgc tgc ggg gac aca ccc agc tcc acg<br>Ser Val Phe Pro Leu Ala Pro Cys Cys Gly Asp Thr Pro Ser Ser Thr<br>145                 150                 155                 160 | | 480 |
| gtc acc ctg ggt tgt ctt gtg aag gga tac ctc ccg gaa ccc gtg acc<br>Val Thr Leu Gly Cys Leu Val Lys Gly Tyr Leu Pro Glu Pro Val Thr<br>                165                 170                 175 | | 528 |
| gtg acc tgg aac tcc ggc acc ctg acc aat gga gtg cgg acc ttc ccg<br>Val Thr Trp Asn Ser Gly Thr Leu Thr Asn Gly Val Arg Thr Phe Pro<br>            180                 185                 190 | | 576 |
| agc gtc agg cag tcc tcc ggg ttg tac agc ttg tct agc gtg gtg tcc<br>Ser Val Arg Gln Ser Ser Gly Leu Tyr Ser Leu Ser Ser Val Val Ser<br>        195                 200                 205 | | 624 |
| gtg acg tcg tca agc cag cct gtg act tgc aat gtg gcc cat ccg gcc | | 672 |

```
                Val Thr Ser Ser Ser Gln Pro Val Thr Cys Asn Val Ala His Pro Ala
                                    210                 215                 220 acc aac acc aag gtc gac aag acc gtg gcg cct tcc acc tgt tcc aag            720
Thr Asn Thr Lys Val Asp Lys Thr Val Ala Pro Ser Thr Cys Ser Lys
225                 230                 235                 240 ccc act tgc ccg ccg cct gag ctc ctg gga gga ccg tcc gtg ttc atc            768
Pro Thr Cys Pro Pro Pro Glu Leu Leu Gly Gly Pro Ser Val Phe Ile
                245                 250                 255 ttc cct cca aaa ccc aag gat acc ctg atg att agc cgc act ccc gaa            816
Phe Pro Pro Lys Pro Lys Asp Thr Leu Met Ile Ser Arg Thr Pro Glu
            260                 265                 270 gtc act tgc gtg gtc gtg gac gtg tcg cag gac gat cct gag gtg cag            864
Val Thr Cys Val Val Val Asp Val Ser Gln Asp Asp Pro Glu Val Gln
        275                 280                 285 ttc act tgg tac atc aac aac gaa caa gtc cgg aca gct aga cca ccg            912
Phe Thr Trp Tyr Ile Asn Asn Glu Gln Val Arg Thr Ala Arg Pro Pro
    290                 295                 300 ctg cgc gag cag cag ttc aac tca act atc cgg gtg gtg tcc acc ctg            960
Leu Arg Glu Gln Gln Phe Asn Ser Thr Ile Arg Val Val Ser Thr Leu
305                 310                 315                 320 ccg atc gcg cat cag gat tgg ctg cgg ggg aag gag ttc aag tgc aaa            1008
Pro Ile Ala His Gln Asp Trp Leu Arg Gly Lys Glu Phe Lys Cys Lys
                325                 330                 335 gtc cac aac aag gcc ctg ccc gcc ccc atc gaa aag acc atc tcc aag            1056
Val His Asn Lys Ala Leu Pro Ala Pro Ile Glu Lys Thr Ile Ser Lys
                340                 345                 350 gct cgg ggc cag cct ctg gag ccc aaa gtg tac acc atg ggc ccg cct            1104
Ala Arg Gly Gln Pro Leu Glu Pro Lys Val Tyr Thr Met Gly Pro Pro
            355                 360                 365 cgc gag gag ctc tcc tca cgc tcg gtg tcg ctg act tgc atg att aac            1152
Arg Glu Glu Leu Ser Ser Arg Ser Val Ser Leu Thr Cys Met Ile Asn
        370                 375                 380 ggc ttc tac cct tcc gac atc tcc gtg gaa tgg gag aag aac gga aaa            1200
Gly Phe Tyr Pro Ser Asp Ile Ser Val Glu Trp Glu Lys Asn Gly Lys
385                 390                 395                 400 gcc gaa gat aac tac aag acc acg ccc gcc gtg ctg gac tcc gac gga            1248
Ala Glu Asp Asn Tyr Lys Thr Thr Pro Ala Val Leu Asp Ser Asp Gly
                405                 410                 415 agc tat ttc ctg tac tcc aag ctc tcc gtc ccc act tcg gaa tgg cag            1296
Ser Tyr Phe Leu Tyr Ser Lys Leu Ser Val Pro Thr Ser Glu Trp Gln
                420                 425                 430 agg ggg gac gtg ttc act tgc tcc gtg atg cac gag gca ctc cac aac            1344
Arg Gly Asp Val Phe Thr Cys Ser Val Met His Glu Ala Leu His Asn
            435                 440                 445 cac tac acc caa aag agc att tcg cgg tca cct ggc aag taa                    1386
His Tyr Thr Gln Lys Ser Ile Ser Arg Ser Pro Gly Lys
        450                 455                 460

<210> SEQ ID NO 14
<211> LENGTH: 461
<212> TYPE: PRT
<213> ORGANISM: Artificial Sequence
<220> FEATURE:
<223> OTHER INFORMATION: Synthetic Construct

<400> SEQUENCE: 14

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30
```

-continued

```
Thr Asp Thr Leu Thr Leu Thr Cys Lys Ala Ser Gly Phe Thr Val Ser
             35                  40                  45

Ser Tyr Asp Met Gly Trp Leu Arg Gln Ala Pro Gly Asn Gly Leu Glu
 50                  55                  60

Ser Ile Gly Ala Ile Gly Ser Asp Gly Ser Glu Tyr Tyr Val Ser Trp
 65                  70                  75                  80

Ala Arg Gly Arg Thr Ala Ile Thr Arg Asn Thr Asn Gln Asn Thr Val
                 85                  90                  95

Thr Leu Lys Met Thr Ser Leu Thr Ala Ala Asp Thr Ala Thr Tyr Phe
            100                 105                 110

Cys Ala Arg Asp Ser His Tyr Ser Tyr Gly Tyr Asp Tyr Asp Ile Trp
            115                 120                 125

Gly Pro Gly Thr Leu Val Thr Val Ser Ser Gly Gln Pro Lys Ala Pro
        130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Thr Cys Pro Pro Pro Glu Leu Leu Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Ala Val Leu Asp Ser Asp Gly
            405                 410                 415

Ser Tyr Phe Leu Tyr Ser Lys Leu Ser Val Pro Thr Ser Glu Trp Gln
        420                 425                 430

Arg Gly Asp Val Phe Thr Cys Ser Val Met His Glu Ala Leu His Asn
    435                 440                 445

His Tyr Thr Gln Lys Ser Ile Ser Arg Ser Pro Gly Lys
```

<210> SEQ ID NO 15
<211> LENGTH: 714
<212> TYPE: DNA
<213> ORGANISM: Artificial Sequence
<220> FEATURE:
<223> OTHER INFORMATION: clone encoding A2 monoclonal antibody light chain 1
<220> FEATURE:
<221> NAME/KEY: CDS
<222> LOCATION: (1)..(711)

<400> SEQUENCE: 15

```
atg gac acg agg gcc ccc act cag ctg ctg ggg ctc ctg ctg ctc tgg      48
Met Asp Thr Arg Ala Pro Thr Gln Leu Leu Gly Leu Leu Leu Leu Trp
1               5                   10                  15 ctc cca ggt gcc aca ttt gcc caa gtg ctg acc cag act cca tcc cct      96
Leu Pro Gly Ala Thr Phe Ala Gln Val Leu Thr Gln Thr Pro Ser Pro
            20                  25                  30 gtg tct gca gct gtg gga ggc aca gtc agc atc agt tgc cag tcc agt     144
Val Ser Ala Ala Val Gly Gly Thr Val Ser Ile Ser Cys Gln Ser Ser
        35                  40                  45 cag agt att tat agt aac tac tta tcc tgg tat cag cag aaa cca ggg     192
Gln Ser Ile Tyr Ser Asn Tyr Leu Ser Trp Tyr Gln Gln Lys Pro Gly
    50                  55                  60 cag cct ccc aag ctc ctg atc tat tat gca tcc act ctg gca tct ggg     240
Gln Pro Pro Lys Leu Leu Ile Tyr Tyr Ala Ser Thr Leu Ala Ser Gly
65                  70                  75                  80 gtc cct tcg cgg ttc aaa ggc agt gga tct ggg aca cag ttc act ctc     288
Val Pro Ser Arg Phe Lys Gly Ser Gly Ser Gly Thr Gln Phe Thr Leu
                85                  90                  95 acc atc agc ggc gtg cag tgt gat gat gct gcc act tac tac tgt caa     336
Thr Ile Ser Gly Val Gln Cys Asp Asp Ala Ala Thr Tyr Tyr Cys Gln
            100                 105                 110 ggc act tat tat gtc act ggt tgg tac gac gct ttc ggc gga ggg acc     384
Gly Thr Tyr Tyr Val Thr Gly Trp Tyr Asp Ala Phe Gly Gly Gly Thr
        115                 120                 125 gag gtg gtg gtc aaa ggt gat cca gtt gca cct act gtc ctc atc ttc     432
Glu Val Val Val Lys Gly Asp Pro Val Ala Pro Thr Val Leu Ile Phe
    130                 135                 140 cca cca gct gct gat cag gtg gca act gga aca gtc acc atc gtg tgc     480
Pro Pro Ala Ala Asp Gln Val Ala Thr Gly Thr Val Thr Ile Val Cys
145                 150                 155                 160 gtg gct aac aag tac ttc ccg gac gtg acc gtg acc tgg gaa gtc gac     528
Val Ala Asn Lys Tyr Phe Pro Asp Val Thr Val Thr Trp Glu Val Asp
                165                 170                 175 gga acc act cag acc act ggt atc gag aac agc aag acg ccc cag aac     576
Gly Thr Thr Gln Thr Thr Gly Ile Glu Asn Ser Lys Thr Pro Gln Asn
            180                 185                 190 tcc gcc gat tgt act tat aac ctg tcc tcc aca ctg acc ctc acc tcg     624
Ser Ala Asp Cys Thr Tyr Asn Leu Ser Ser Thr Leu Thr Leu Thr Ser
        195                 200                 205 acc cag tac aat tcc cac aag gag tac act tgc aaa gtc acc cag gga     672
Thr Gln Tyr Asn Ser His Lys Glu Tyr Thr Cys Lys Val Thr Gln Gly
    210                 215                 220 acc act tca gtg gtg cag agc ttc aac cgg ggg gat tgc tga             714
Thr Thr Ser Val Val Gln Ser Phe Asn Arg Gly Asp Cys
225                 230                 235
```

<210> SEQ ID NO 16
<211> LENGTH: 237

```
<212> TYPE: PRT
<213> ORGANISM: Artificial Sequence
<220> FEATURE:
<223> OTHER INFORMATION: Synthetic Construct

<400> SEQUENCE: 16

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Ser Ile Ser Cys Gln Ser Ser
        35                  40                  45

Gln Ser Ile Tyr Ser Asn Tyr Leu Ser Trp Tyr Gln Gln Lys Pro Gly
    50                  55                  60

Gln Pro Pro Lys Leu Leu Ile Tyr Tyr Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Gln Cys Asp Asp Ala Ala Thr Tyr Tyr Cys Gln
            100                 105                 110

Gly Thr Tyr Tyr Val Thr Gly Trp Tyr Asp Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 17
<211> LENGTH: 1386
<212> TYPE: DNA
<213> ORGANISM: Artificial Sequence
<220> FEATURE:
<223> OTHER INFORMATION: clone encoding A6 monoclonal antibody heavy
      chain 1
<220> FEATURE:
<221> NAME/KEY: CDS
<222> LOCATION: (1)..(1383)

<400> SEQUENCE: 17 atg gag act ggg ctg cgc tgg ctt ctc ctg gtc gct gtg ctc aaa ggt    48
Met Glu Thr Gly Leu Arg Trp Leu Leu Leu Val Ala Val Leu Lys Gly
1               5                   10                  15 gtc cag tgt cag tcg gtg aag gag tcc gag gga ggt ctc ttc aag cca    96
Val Gln Cys Gln Ser Val Lys Glu Ser Glu Gly Gly Leu Phe Lys Pro
            20                  25                  30 acg gat acc ctg aca ctc acc tgc aaa gcc tct gga ttc acc gtc agt    144
Thr Asp Thr Leu Thr Leu Thr Cys Lys Ala Ser Gly Phe Thr Val Ser
        35                  40                  45 agt tac gac atg ggc tgg ctc cgc cag gct cca ggg aac ggg ctt gaa    192
```

```
Ser Tyr Asp Met Gly Trp Leu Arg Gln Ala Pro Gly Asn Gly Leu Glu
     50                  55                  60 tct atc gga gcc att ggt agt gat ggt agt gag tac tat gtg agc tgg      240
Ser Ile Gly Ala Ile Gly Ser Asp Gly Ser Glu Tyr Tyr Val Ser Trp
 65                  70                  75                  80 gcg aga ggc cga acc acc atc acc aga aac acc aac cag aac acg gtg      288
Ala Arg Gly Arg Thr Thr Ile Thr Arg Asn Thr Asn Gln Asn Thr Val
                     85                  90                  95 act ctg aaa atg acc agt ctg aca gcc gcg gac acg gcc acc tat ttc      336
Thr Leu Lys Met Thr Ser Leu Thr Ala Ala Asp Thr Ala Thr Tyr Phe
                100                 105                 110 tgt gcg aga gac tca cac tat agc tat ggc tat gat tat gat atc tgg      384
Cys Ala Arg Asp Ser His Tyr Ser Tyr Gly Tyr Asp Tyr Asp Ile Trp
                115                 120                 125 ggc cca ggc acc ctg gtc acc gtc tcc tca ggg caa cct aag gct cca      432
Gly Pro Gly Thr Leu Val Thr Val Ser Ser Gly Gln Pro Lys Ala Pro
            130                 135                 140 tca gtc ttc cca ctg gcc ccc tgc tgc ggg gac aca ccc agc tcc acg      480
Ser Val Phe Pro Leu Ala Pro Cys Cys Gly Asp Thr Pro Ser Ser Thr
145                 150                 155                 160 gtc acc ctg ggt tgt ctt gtg aag gga tac ctc ccg gaa ccc gtg acc      528
Val Thr Leu Gly Cys Leu Val Lys Gly Tyr Leu Pro Glu Pro Val Thr
                165                 170                 175 gtg acc tgg aac tcc ggc acc ctg acc aat gga gtg cgg acc ttc ccg      576
Val Thr Trp Asn Ser Gly Thr Leu Thr Asn Gly Val Arg Thr Phe Pro
                180                 185                 190 agc gtc agg cag tcc tcc ggg ttg tac agc ttg tct agc gtg gtg tcc      624
Ser Val Arg Gln Ser Ser Gly Leu Tyr Ser Leu Ser Ser Val Val Ser
                195                 200                 205 gtg acg tcg tca agc cag cct gtg act tgc aat gtg gcc cat ccg gcc      672
Val Thr Ser Ser Ser Gln Pro Val Thr Cys Asn Val Ala His Pro Ala
            210                 215                 220 acc aac acc aag gtc gac aag acc gtg gcg cct tcc acc tgt tcc aag      720
Thr Asn Thr Lys Val Asp Lys Thr Val Ala Pro Ser Thr Cys Ser Lys
225                 230                 235                 240 ccc act tgc ccg ccg cct gag ctc ctg gga gga ccg tcc gtg ttc atc      768
Pro Thr Cys Pro Pro Pro Glu Leu Leu Gly Gly Pro Ser Val Phe Ile
                245                 250                 255 ttc cct cca aaa ccc aag gat acc ctg atg att agc cgc act ccc gaa      816
Phe Pro Pro Lys Pro Lys Asp Thr Leu Met Ile Ser Arg Thr Pro Glu
                260                 265                 270 gtc act tgc gtg gtc gtg gac gtg tcg cag gac gat cct gag gtg cag      864
Val Thr Cys Val Val Val Asp Val Ser Gln Asp Asp Pro Glu Val Gln
                275                 280                 285 ttc act tgg tac atc aac aac gaa caa gtc cgg aca gct aga cca ccg      912
Phe Thr Trp Tyr Ile Asn Asn Glu Gln Val Arg Thr Ala Arg Pro Pro
            290                 295                 300 ctg cgc gag cag cag ttc aac tca act atc cgg gtg gtg tcc acc ctg      960
Leu Arg Glu Gln Gln Phe Asn Ser Thr Ile Arg Val Val Ser Thr Leu
305                 310                 315                 320 ccg atc gcg cat cag gat tgg ctg cgg ggg aag gag ttc aag tgc aaa     1008
Pro Ile Ala His Gln Asp Trp Leu Arg Gly Lys Glu Phe Lys Cys Lys
                325                 330                 335 gtc cac aac aag gcc ctg ccc gcc ccc atc gaa aag acc atc tcc aag     1056
Val His Asn Lys Ala Leu Pro Ala Pro Ile Glu Lys Thr Ile Ser Lys
                340                 345                 350 gct cgg ggc cag cct ctg gag ccc aaa gtg tac acc atg ggc ccg cct     1104
Ala Arg Gly Gln Pro Leu Glu Pro Lys Val Tyr Thr Met Gly Pro Pro
            355                 360                 365
```

| | | | | | | | | | | | | | | | |
|---|---|---|---|---|---|---|---|---|---|---|---|---|---|---|---|
| cgc | gag | gag | ctc | tcc | tca | cgc | tcg | gtg | tcg | ctg | act | tgc | atg | att | aac | 1152 |
| Arg | Glu | Glu | Leu | Ser | Ser | Arg | Ser | Val | Ser | Leu | Thr | Cys | Met | Ile | Asn |
| 370 | | | | 375 | | | | | 380 | | | | | |

| ggc | ttc | tac | cct | tcc | gac | atc | tcc | gtg | gaa | tgg | gag | aag | aac | gga | aaa | 1200 |
| Gly | Phe | Tyr | Pro | Ser | Asp | Ile | Ser | Val | Glu | Trp | Glu | Lys | Asn | Gly | Lys |
| 385 | | | | | 390 | | | | 395 | | | | | 400 |

| gcc | gaa | gat | aac | tac | aag | acc | acg | ccc | gcc | gtg | ctg | gac | tcc | gac | gga | 1248 |
| Ala | Glu | Asp | Asn | Tyr | Lys | Thr | Thr | Pro | Ala | Val | Leu | Asp | Ser | Asp | Gly |
| | | | 405 | | | | | 410 | | | | | 415 |

| agc | tat | ttc | ctg | tac | tcc | aag | ctc | tcc | gtc | ccc | act | tcg | gaa | tgg | cag | 1296 |
| Ser | Tyr | Phe | Leu | Tyr | Ser | Lys | Leu | Ser | Val | Pro | Thr | Ser | Glu | Trp | Gln |
| | | | 420 | | | | 425 | | | | | 430 |

| agg | ggg | gac | gtg | ttc | act | tgc | tcc | gtg | atg | cac | gag | gca | ctc | cac | aac | 1344 |
| Arg | Gly | Asp | Val | Phe | Thr | Cys | Ser | Val | Met | His | Glu | Ala | Leu | His | Asn |
| | | | 435 | | | | 440 | | | | 445 |

| cac | tac | acc | caa | aag | agc | att | tcg | cgg | tca | cct | ggc | aag | taa | | | 1386 |
| His | Tyr | Thr | Gln | Lys | Ser | Ile | Ser | Arg | Ser | Pro | Gly | Lys |
| 450 | | | | | 455 | | | | | 460 |

<210> SEQ ID NO 18
<211> LENGTH: 461
<212> TYPE: PRT
<213> ORGANISM: Artificial Sequence
<220> FEATURE:
<223> OTHER INFORMATION: Synthetic Construct

<400> SEQUENCE: 18

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Lys Ala Ser Gly Phe Thr Val Ser
        35                  40                  45

Ser Tyr Asp Met Gly Trp Leu Arg Gln Ala Pro Gly Asn Gly Leu Glu
    50                  55                  60

Ser Ile Gly Ala Ile Gly Ser Asp Gly Ser Glu Tyr Tyr Val Ser Trp
65                  70                  75                  80

Ala Arg Gly Arg Thr Thr Ile Thr Arg Asn Thr Asn Gln Asn Thr Val
                85                  90                  95

Thr Leu Lys Met Thr Ser Leu Thr Ala Ala Asp Thr Ala Thr Tyr Phe
            100                 105                 110

Cys Ala Arg Asp Ser His Tyr Ser Tyr Gly Tyr Asp Tyr Asp Ile Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

```
Pro Thr Cys Pro Pro Pro Glu Leu Leu Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Ala Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460

<210> SEQ ID NO 19
<211> LENGTH: 714
<212> TYPE: DNA
<213> ORGANISM: Artificial Sequence
<220> FEATURE:
<223> OTHER INFORMATION: clone encoding A6 monoclonal antibody light
      chain 4
<220> FEATURE:
<221> NAME/KEY: CDS
<222> LOCATION: (1)..(711)

<400> SEQUENCE: 19 atg gac acg agg gcc ccc act cag ctg ctg ggg ctc ctg ctg ctc tgg    48
Met Asp Thr Arg Ala Pro Thr Gln Leu Leu Gly Leu Leu Leu Leu Trp
1               5                   10                  15 ctc cca ggt gcc aca ttt gcc caa gtg ctg acc cag act cca tcc cct    96
Leu Pro Gly Ala Thr Phe Ala Gln Val Leu Thr Gln Thr Pro Ser Pro
                20                  25                  30 gtg tct gca gct gtg gga ggc aca gtc agc atc agt tgc cag tcc agt   144
Val Ser Ala Ala Val Gly Gly Thr Val Ser Ile Ser Cys Gln Ser Ser
            35                  40                  45 cag agt att tat agt aac tac tta tcc tgg tat cag cag aaa cca ggg   192
Gln Ser Ile Tyr Ser Asn Tyr Leu Ser Trp Tyr Gln Gln Lys Pro Gly
        50                  55                  60 cag cct ccc aag ctc ctg atc tat tat gca tcc act ctg gca tct ggg   240
Gln Pro Pro Lys Leu Leu Ile Tyr Tyr Ala Ser Thr Leu Ala Ser Gly
65                  70                  75                  80 gtc cct tcg cgg ttc aaa ggc agt gga tct ggg aca cag ttc act ctc   288
Val Pro Ser Arg Phe Lys Gly Ser Gly Ser Gly Thr Gln Phe Thr Leu
                85                  90                  95
```

```
acc atc agc ggc gtg cag tgt gat gat gct gcc act tac tac tgt caa    336
Thr Ile Ser Gly Val Gln Cys Asp Asp Ala Ala Thr Tyr Tyr Cys Gln
            100                 105                 110 ggc act tat tat gtc act ggt tgg tac gac gct ttc ggc gga ggg acc    384
Gly Thr Tyr Tyr Val Thr Gly Trp Tyr Asp Ala Phe Gly Gly Gly Thr
            115                 120                 125 gag gtg gtg gtc aaa ggt gat cca gtt gca cct act gtc ctc atc ttc    432
Glu Val Val Val Lys Gly Asp Pro Val Ala Pro Thr Val Leu Ile Phe
130                 135                 140 cca cca gct gct gat cag gtg gca act gga aca gtc acc atc gtg tgc    480
Pro Pro Ala Ala Asp Gln Val Ala Thr Gly Thr Val Thr Ile Val Cys
145                 150                 155                 160 gtg gct aac aag tac ttc ccg gac gtg acc gtg acc tgg gaa gtc gac    528
Val Ala Asn Lys Tyr Phe Pro Asp Val Thr Val Thr Trp Glu Val Asp
                165                 170                 175 gga acc act cag acc act ggt atc gag aac agc aag acg ccc cag aac    576
Gly Thr Thr Gln Thr Thr Gly Ile Glu Asn Ser Lys Thr Pro Gln Asn
            180                 185                 190 tcc gcc gat tgt act tat aac ctg tcc tcc aca ctg acc ctc acc tcg    624
Ser Ala Asp Cys Thr Tyr Asn Leu Ser Ser Thr Leu Thr Leu Thr Ser
            195                 200                 205 acc cag tac aat tcc cac aag gag tac act tgc aaa gtc acc cag gga    672
Thr Gln Tyr Asn Ser His Lys Glu Tyr Thr Cys Lys Val Thr Gln Gly
210                 215                 220 acc act tca gtg gtg cag agc ttc aac cgg ggg gat tgc tga            714
Thr Thr Ser Val Val Gln Ser Phe Asn Arg Gly Asp Cys
225                 230                 235
```

<210> SEQ ID NO 20
<211> LENGTH: 237
<212> TYPE: PRT
<213> ORGANISM: Artificial Sequence
<220> FEATURE:
<223> OTHER INFORMATION: Synthetic Construct

<400> SEQUENCE: 20

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Ser Ile Ser Cys Gln Ser Ser
            35                  40                  45

Gln Ser Ile Tyr Ser Asn Tyr Leu Ser Trp Tyr Gln Gln Lys Pro Gly
        50                  55                  60

Gln Pro Pro Lys Leu Leu Ile Tyr Tyr Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Gln Cys Asp Asp Ala Ala Thr Tyr Tyr Cys Gln
            100                 105                 110

Gly Thr Tyr Tyr Val Thr Gly Trp Tyr Asp Ala Phe Gly Gly Gly Thr
        115                 120                 125

Glu Val Val Val Lys Gly Asp Pro Val Ala Pro Thr Val Leu Ile Phe
130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175
```

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 21
<211> LENGTH: 1371
<212> TYPE: DNA
<213> ORGANISM: Artificial Sequence
<220> FEATURE:
<223> OTHER INFORMATION: clone encoding E5 monoclonal antibody heavy
      chain 1
<220> FEATURE:
<221> NAME/KEY: CDS
<222> LOCATION: (1)..(1368)
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 21

| | |
|---|---|
| atg gag act ggg ctg cgc tgg ctt ctc ctg gtc gct gtg ctc aaa ggt<br>Met Glu Thr Gly Leu Arg Trp Leu Leu Leu Val Ala Val Leu Lys Gly<br>1               5                   10                  15 | 48 |
| gtc can tgt nng tcg gtg aag gag tcc gag gga ggt ctc ttc aag cca<br>Val Xaa Cys Xaa Ser Val Lys Glu Ser Glu Gly Gly Leu Phe Lys Pro<br>            20                  25                  30 | 96 |
| acg gct acc ctg aca ctc acc tgc aca gtc tct gga ttc tcc ctc agt<br>Thr Ala Thr Leu Thr Leu Thr Cys Thr Val Ser Gly Phe Ser Leu Ser<br>        35                  40                  45 | 144 |
| agc tac gac atg agt tgg gtc cgc cag gct cca ggg aac ggg ctg gaa<br>Ser Tyr Asp Met Ser Trp Val Arg Gln Ala Pro Gly Asn Gly Leu Glu<br>    50                  55                  60 | 192 |
| tgg atc gga tac ctt agt agt gat ggt cgc gca tac tac gcg agc tgg<br>Trp Ile Gly Tyr Leu Ser Ser Asp Gly Arg Ala Tyr Tyr Ala Ser Trp<br>65                  70                  75                  80 | 240 |
| gcg aaa agc cga tcc acc atc acc aga aac acc aac ctg aac acg gtg<br>Ala Lys Ser Arg Ser Thr Ile Thr Arg Asn Thr Asn Leu Asn Thr Val<br>                85                  90                  95 | 288 |
| act ctg aaa atg acc agt ctg aca gcc gcg gac acg gcc acc tat ttc<br>Thr Leu Lys Met Thr Ser Leu Thr Ala Ala Asp Thr Ala Thr Tyr Phe<br>            100                 105                 110 | 336 |
| tgt gcg aga ggt gat aat act gct gac atc tgg ggc cca ggc acc ctg<br>Cys Ala Arg Gly Asp Asn Thr Ala Asp Ile Trp Gly Pro Gly Thr Leu<br>        115                 120                 125 | 384 |
| gtc acc gtc tcc tca ggg caa cct aag gct cca tca gtc ttc cca ctg<br>Val Thr Val Ser Ser Gly Gln Pro Lys Ala Pro Ser Val Phe Pro Leu<br>    130                 135                 140 | 432 |
| gcc ccc tgc tgc ggg gac aca ccc agc tcc acg gtc acc ctg ggt tgt<br>Ala Pro Cys Cys Gly Asp Thr Pro Ser Ser Thr Val Thr Leu Gly Cys<br>145                 150                 155                 160 | 480 |
| ctt gtg aag gga tac ctc ccg gaa ccc gtg acc gtg acc tgg aac tcc<br>Leu Val Lys Gly Tyr Leu Pro Glu Pro Val Thr Val Thr Trp Asn Ser<br>                165                 170                 175 | 528 |

```
ggc acc ctg acc aat gga gtg cgg acc ttc ccg agc gtc agg cag tcc    576
Gly Thr Leu Thr Asn Gly Val Arg Thr Phe Pro Ser Val Arg Gln Ser
            180                 185                 190 tcc ggg ttg tac agc ttg tct agc gtg gtg tcc gtg acg tcg tca agc    624
Ser Gly Leu Tyr Ser Leu Ser Ser Val Val Ser Val Thr Ser Ser Ser
        195                 200                 205 cag cct gtg act tgc aat gtg gcc cat ccg gcc acc aac acc aag gtc    672
Gln Pro Val Thr Cys Asn Val Ala His Pro Ala Thr Asn Thr Lys Val
    210                 215                 220 gac aag acc gtg gcg cct tcc acc tgt tcc aag ccc act tgc ccg ccg    720
Asp Lys Thr Val Ala Pro Ser Thr Cys Ser Lys Pro Thr Cys Pro Pro
225                 230                 235                 240 cct gag ctc ctg gga gga ccg tcc gtg ttc atc ttc cct cca aaa ccc    768
Pro Glu Leu Leu Gly Gly Pro Ser Val Phe Ile Phe Pro Pro Lys Pro
                245                 250                 255 aag gat acc ctg atg att agc cgc act ccc gaa gtc act tgc gtg gtc    816
Lys Asp Thr Leu Met Ile Ser Arg Thr Pro Glu Val Thr Cys Val Val
            260                 265                 270 gtg gac gtg tcg cag gac gat cct gag gtg cag ttc act tgg tac atc    864
Val Asp Val Ser Gln Asp Asp Pro Glu Val Gln Phe Thr Trp Tyr Ile
        275                 280                 285 aac aac gaa caa gtc cgg aca gct aga cca ccg ctg cgc gag cag cag    912
Asn Asn Glu Gln Val Arg Thr Ala Arg Pro Pro Leu Arg Glu Gln Gln
    290                 295                 300 ttc aac tca act atc cgg gtg gtg tcc acc ctg ccg atc gcg cat cag    960
Phe Asn Ser Thr Ile Arg Val Val Ser Thr Leu Pro Ile Ala His Gln
305                 310                 315                 320 gat tgg ctg cgg ggg aag gag ttc aag tgc aaa gtc cac aac aag gcc   1008
Asp Trp Leu Arg Gly Lys Glu Phe Lys Cys Lys Val His Asn Lys Ala
                325                 330                 335 ctg ccc gcc ccc atc gaa aag acc atc tcc aag gct cgg ggc cag cct   1056
Leu Pro Ala Pro Ile Glu Lys Thr Ile Ser Lys Ala Arg Gly Gln Pro
            340                 345                 350 ctg gag ccc aaa gtg tac acc atg ggc ccg cct cgc gag gag ctc tcc   1104
Leu Glu Pro Lys Val Tyr Thr Met Gly Pro Pro Arg Glu Glu Leu Ser
        355                 360                 365 tca cgc tcg gtg tcg ctg act tgc atg att aac ggc ttc tac cct tcc   1152
Ser Arg Ser Val Ser Leu Thr Cys Met Ile Asn Gly Phe Tyr Pro Ser
    370                 375                 380 gac atc tcc gtg gaa tgg gag aag aac gga aaa gcc gaa gat aac tac   1200
Asp Ile Ser Val Glu Trp Glu Lys Asn Gly Lys Ala Glu Asp Asn Tyr
385                 390                 395                 400 aag acc acg ccc gcc gtg ctg gac tcc gac gga agc tat ttc ctg tac   1248
Lys Thr Thr Pro Ala Val Leu Asp Ser Asp Gly Ser Tyr Phe Leu Tyr
                405                 410                 415 tcc aag ctc tcc gtc ccc act tcg gaa tgg cag agg ggg gac gtg ttc   1296
Ser Lys Leu Ser Val Pro Thr Ser Glu Trp Gln Arg Gly Asp Val Phe
            420                 425                 430 act tgc tcc gtg atg cac gag gca ctc cac aac cac tac acc caa aag   1344
Thr Cys Ser Val Met His Glu Ala Leu His Asn His Tyr Thr Gln Lys
        435                 440                 445 agc att tcg cgg tca cct ggc aag taa                               1371
Ser Ile Ser Arg Ser Pro Gly Lys
    450                 455

<210> SEQ ID NO 22
<211> LENGTH: 456
<212> TYPE: PRT
<213> ORGANISM: Artificial Sequence
<220> FEATURE:
<221> NAME/KEY: misc_feature
```

```
<222> LOCATION: (18)..(18)
<223> OTHER INFORMATION: The 'Xaa' at location 18 stands for Gln, or
      His.
<220> FEATURE:
<221> NAME/KEY: misc_feature
<222> LOCATION: (20)..(20)
<223> OTHER INFORMATION: The 'Xaa' at location 20 stands for Lys, Arg,
      Thr, Met, Glu, Gly, Ala, Val, Gln, Pro, Leu, Trp, or Ser.
<220> FEATURE:
<223> OTHER INFORMATION: Synthetic Construct

<400> SEQUENCE: 22

Met Glu Thr Gly Leu Arg Trp Leu Leu Leu Val Ala Val Leu Lys Gly
1               5                   10                  15

Val Xaa Cys Xaa Ser Val Lys Glu Ser Glu Gly Gly Leu Phe Lys Pro
            20                  25                  30

Thr Ala Thr Leu Thr Leu Thr Cys Thr Val Ser Gly Phe Ser Leu Ser
            35                  40                  45

Ser Tyr Asp Met Ser Trp Val Arg Gln Ala Pro Gly Asn Gly Leu Glu
        50                  55                  60

Trp Ile Gly Tyr Leu Ser Ser Asp Gly Arg Ala Tyr Tyr Ala Ser Trp
65                  70                  75                  80

Ala Lys Ser Arg Ser Thr Ile Thr Arg Asn Thr Asn Leu Asn Thr Val
                85                  90                  95

Thr Leu Lys Met Thr Ser Leu Thr Ala Ala Asp Thr Ala Thr Tyr Phe
            100                 105                 110

Cys Ala Arg Gly Asp Asn Thr Ala Asp Ile Trp Gly Pro Gly Thr Leu
        115                 120                 125

Val Thr Val Ser Ser Gly Gln Pro Lys Ala Pro Ser Val Phe Pro Leu
130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350
```

```
Leu Glu Pro Lys Val Tyr Thr Met Gly Pro Pro Arg Glu Glu Leu Ser
            355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
            435                 440                 445

Ser Ile Ser Arg Ser Pro Gly Lys
    450                 455

<210> SEQ ID NO 23
<211> LENGTH: 711
<212> TYPE: DNA
<213> ORGANISM: Artificial Sequence
<220> FEATURE:
<223> OTHER INFORMATION: clone encoding E5 monoclonal antibody light
      chain 3
<220> FEATURE:
<221> NAME/KEY: CDS
<222> LOCATION: (1)..(708)

<400> SEQUENCE: 23
```

| | | | | | | | | | | | | | | | | |
|---|---|---|---|---|---|---|---|---|---|---|---|---|---|---|---|---|
| atg | gac | acg | agg | gcc | ccc | act | cag | ctg | ctg | ggg | ctc | ctg | ctg | ctc | tgg | 48 |
| Met | Asp | Thr | Arg | Ala | Pro | Thr | Gln | Leu | Leu | Gly | Leu | Leu | Leu | Leu | Trp | |
| 1 | | | | 5 | | | | | 10 | | | | | 15 | | |
| ctc | cca | ggt | gcc | aca | ttt | gct | caa | gtg | ctg | acc | cag | act | cca | tcc | tcc | 96 |
| Leu | Pro | Gly | Ala | Thr | Phe | Ala | Gln | Val | Leu | Thr | Gln | Thr | Pro | Ser | Ser | |
| | | | 20 | | | | | 25 | | | | | 30 | | | |
| gtg | tct | gca | gct | gtg | gga | ggc | aca | gtc | acc | atc | aat | tgc | cag | tcc | agt | 144 |
| Val | Ser | Ala | Ala | Val | Gly | Gly | Thr | Val | Thr | Ile | Asn | Cys | Gln | Ser | Ser | |
| | | 35 | | | | | 40 | | | | | 45 | | | | |
| cag | agt | gtt | tat | aag | aac | aac | gac | tta | gcc | tgg | tat | cag | cag | aaa | cta | 192 |
| Gln | Ser | Val | Tyr | Lys | Asn | Asn | Asp | Leu | Ala | Trp | Tyr | Gln | Gln | Lys | Leu | |
| | 50 | | | | | 55 | | | | | 60 | | | | | |
| ggg | cag | cct | ccc | aag | ctc | ctg | atc | tat | ttt | gca | tcc | act | ctg | gca | tct | 240 |
| Gly | Gln | Pro | Pro | Lys | Leu | Leu | Ile | Tyr | Phe | Ala | Ser | Thr | Leu | Ala | Ser | |
| 65 | | | | | 70 | | | | | 75 | | | | | 80 | |
| ggg | gtc | cca | tcg | cgg | ttc | aaa | ggc | agt | gga | tct | ggg | aca | cag | ttc | act | 288 |
| Gly | Val | Pro | Ser | Arg | Phe | Lys | Gly | Ser | Gly | Ser | Gly | Thr | Gln | Phe | Thr | |
| | | | | 85 | | | | | 90 | | | | | 95 | | |
| ctc | acc | atc | agc | gac | ctg | gag | tgt | gac | gat | gct | gcc | act | tat | tac | tgt | 336 |
| Leu | Thr | Ile | Ser | Asp | Leu | Glu | Cys | Asp | Asp | Ala | Ala | Thr | Tyr | Tyr | Cys | |
| | | | 100 | | | | | 105 | | | | | 110 | | | |
| gca | ggc | ggt | tat | agt | ggt | cct | gtt | ggt | gct | ttc | ggc | gga | ggg | acc | gag | 384 |
| Ala | Gly | Gly | Tyr | Ser | Gly | Pro | Val | Gly | Ala | Phe | Gly | Gly | Gly | Thr | Glu | |
| | | 115 | | | | | 120 | | | | | 125 | | | | |
| gtg | gtg | gtc | aag | agt | gat | cca | gtt | gca | cct | act | gtc | ctc | atc | ttc | cca | 432 |
| Val | Val | Val | Lys | Ser | Asp | Pro | Val | Ala | Pro | Thr | Val | Leu | Ile | Phe | Pro | |
| | 130 | | | | | 135 | | | | | 140 | | | | | |
| cca | gct | gct | gat | cag | gtg | gca | act | gga | aca | gtc | acc | atc | gtg | tgc | gtg | 480 |
| Pro | Ala | Ala | Asp | Gln | Val | Ala | Thr | Gly | Thr | Val | Thr | Ile | Val | Cys | Val | |
| 145 | | | | | 150 | | | | | 155 | | | | | 160 | |
| gct | aac | aag | tac | ttc | ccg | gac | gtg | acc | gtg | acc | tgg | gaa | gtc | gac | gga | 528 |
| Ala | Asn | Lys | Tyr | Phe | Pro | Asp | Val | Thr | Val | Thr | Trp | Glu | Val | Asp | Gly | |
| | | | | 165 | | | | | 170 | | | | | 175 | | |

```
acc act cag acc act ggt atc gag aac agc aag acg ccc cag aac tcc     576
Thr Thr Gln Thr Thr Gly Ile Glu Asn Ser Lys Thr Pro Gln Asn Ser
            180                 185                 190 gcc gat tgt act tat aac ctg tcc tcc aca ctg acc ctc acc tcg acc     624
Ala Asp Cys Thr Tyr Asn Leu Ser Ser Thr Leu Thr Leu Thr Ser Thr
            195                 200                 205 cag tac aat tcc cac aag gag tac act tgc aaa gtc acc cag gga acc     672
Gln Tyr Asn Ser His Lys Glu Tyr Thr Cys Lys Val Thr Gln Gly Thr
            210                 215                 220 act tca gtg gtg cag agc ttc aac cgg ggg gat tgc tga                 711
Thr Ser Val Val Gln Ser Phe Asn Arg Gly Asp Cys
225                 230                 235
```

<210> SEQ ID NO 24
<211> LENGTH: 236
<212> TYPE: PRT
<213> ORGANISM: Artificial Sequence
<220> FEATURE:
<223> OTHER INFORMATION: Synthetic Construct

<400> SEQUENCE: 24

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ser Ser
            35                  40                  45

Gln Ser Val Tyr Lys Asn Asn Asp Leu Ala Trp Tyr Gln Gln Lys Leu
        50                  55                  60

Gly Gln Pro Pro Lys Leu Leu Ile Tyr Phe Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Gly Tyr Ser Gly Pro Val Gly Ala Phe Gly Gly Gly Thr Glu
        115                 120                 125

Val Val Val Lys Ser Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

<210> SEQ ID NO 25
<211> LENGTH: 1383
<212> TYPE: DNA
<213> ORGANISM: Artificial Sequence
<220> FEATURE:
<223> OTHER INFORMATION: clone encoding G7 monoclonal antibody heavy
      chain 1

<220> FEATURE:
<221> NAME/KEY: CDS
<222> LOCATION: (1)..(1380)

<400> SEQUENCE: 25

```
atg gag act ggg ctg cgc tgg ctt ctc ctg gtc gct gtg ctc aaa ggt      48
Met Glu Thr Gly Leu Arg Trp Leu Leu Leu Val Ala Val Leu Lys Gly
1               5                   10                  15 gtc cag tgt cag tcg gtg aag gag tcc gag gga ggt ctc ttc aag cca      96
Val Gln Cys Gln Ser Val Lys Glu Ser Glu Gly Gly Leu Phe Lys Pro
            20                  25                  30 acg gat acc ctg aca ctc acc tgc aca gtc tct gga ttc tcc ctc agt     144
Thr Asp Thr Leu Thr Leu Thr Cys Thr Val Ser Gly Phe Ser Leu Ser
        35                  40                  45 agt tat gga gtg agc tgg gtc cgc cag gct cca ggg aac ggg ctg gag     192
Ser Tyr Gly Val Ser Trp Val Arg Gln Ala Pro Gly Asn Gly Leu Glu
    50                  55                  60 tgg atc gga ttc att gac aag tat gga cgc aca cac tac gcg agc tgg     240
Trp Ile Gly Phe Ile Asp Lys Tyr Gly Arg Thr His Tyr Ala Ser Trp
65                  70                  75                  80 gcg aaa agc cga tcc acc atc acc aga aat acc aac gag aac acg gtg     288
Ala Lys Ser Arg Ser Thr Ile Thr Arg Asn Thr Asn Glu Asn Thr Val
                85                  90                  95 act ctg aaa atg acc agt ctg aca gcc gcg gac acg gcc acc ttt ttg     336
Thr Leu Lys Met Thr Ser Leu Thr Ala Ala Asp Thr Ala Thr Phe Leu
            100                 105                 110 tgt gcg aga gat gac tat cgt cct gct tat ggt ttc gac atc tgg ggc     384
Cys Ala Arg Asp Asp Tyr Arg Pro Ala Tyr Gly Phe Asp Ile Trp Gly
        115                 120                 125 cca ggc acc ctg gtc acc gtc tcc tca ggg caa cct aag gct cca tca     432
Pro Gly Thr Leu Val Thr Val Ser Ser Gly Gln Pro Lys Ala Pro Ser
    130                 135                 140 gtc ttc cca ctg gcc ccc tgc tgc ggg gac aca ccc agc tcc acg gtc     480
Val Phe Pro Leu Ala Pro Cys Cys Gly Asp Thr Pro Ser Ser Thr Val
145                 150                 155                 160 acc ctg ggt tgt ctt gtg aag gga tac ctc ccg gaa ccc gtg acc gtg     528
Thr Leu Gly Cys Leu Val Lys Gly Tyr Leu Pro Glu Pro Val Thr Val
                165                 170                 175 acc tgg aac tcc ggc acc ctg acc aat gga gtg cgg acc ttc ccg agc     576
Thr Trp Asn Ser Gly Thr Leu Thr Asn Gly Val Arg Thr Phe Pro Ser
            180                 185                 190 gtc agg cag tcc tcc ggg ttg tac agc ttg tct agc gtg gtg tcc gtg     624
Val Arg Gln Ser Ser Gly Leu Tyr Ser Leu Ser Ser Val Val Ser Val
        195                 200                 205 acg tcg tca agc cag cct gtg act tgc aat gtg gcc cat ccg gcc acc     672
Thr Ser Ser Ser Gln Pro Val Thr Cys Asn Val Ala His Pro Ala Thr
    210                 215                 220 aac acc aag gtc gac aag acc gtg gcg cct tcc acc tgt tcc aag ccc     720
Asn Thr Lys Val Asp Lys Thr Val Ala Pro Ser Thr Cys Ser Lys Pro
225                 230                 235                 240 act tgc ccg ccg cct gag ctc ctg gga gga ccg tcc gtg ttc atc ttc     768
Thr Cys Pro Pro Pro Glu Leu Leu Gly Gly Pro Ser Val Phe Ile Phe
                245                 250                 255 cct cca aaa ccc aag gat acc ctg atg att agc cgc act ccc gaa gtc     816
Pro Pro Lys Pro Lys Asp Thr Leu Met Ile Ser Arg Thr Pro Glu Val
            260                 265                 270 act tgc gtg gtc gtg gac gtg tcg cag gac gat cct gag gtg cag ttc     864
Thr Cys Val Val Val Asp Val Ser Gln Asp Asp Pro Glu Val Gln Phe
        275                 280                 285 act tgg tac atc aac aac gaa caa gtc cgg aca gct aga cca ccg ctg     912
```

```
                    Thr Trp Tyr Ile Asn Asn Glu Gln Val Arg Thr Ala Arg Pro Pro Leu
                            290                 295                 300 cgc gag cag cag ttc aac tca act atc cgg gtg gtg tcc acc ctg ccg                   960
Arg Glu Gln Gln Phe Asn Ser Thr Ile Arg Val Val Ser Thr Leu Pro
305                 310                 315                 320 atc gcg cat cag gat tgg ctg cgg ggg aag gag ttc aag tgc aaa gtc                   1008
Ile Ala His Gln Asp Trp Leu Arg Gly Lys Glu Phe Lys Cys Lys Val
                325                 330                 335 cac aac aag gcc ctg ccc gcc ccc atc gaa aag acc atc tcc aag gct                   1056
His Asn Lys Ala Leu Pro Ala Pro Ile Glu Lys Thr Ile Ser Lys Ala
            340                 345                 350 cgg ggc cag cct ctg gag ccc aaa gtg tac acc atg ggc ccg cct cgc                   1104
Arg Gly Gln Pro Leu Glu Pro Lys Val Tyr Thr Met Gly Pro Pro Arg
        355                 360                 365 gag gag ctc tcc tca cgc tcg gtg tcg ctg act tgc atg att aac ggc                   1152
Glu Glu Leu Ser Ser Arg Ser Val Ser Leu Thr Cys Met Ile Asn Gly
    370                 375                 380 ttc tac cct tcc gac atc tcc gtg gaa tgg gag aag aac gga aaa gcc                   1200
Phe Tyr Pro Ser Asp Ile Ser Val Glu Trp Glu Lys Asn Gly Lys Ala
385                 390                 395                 400 gaa gat aac tac aag acc acg ccc gcc gtg ctg gac tcc gac gga agc                   1248
Glu Asp Asn Tyr Lys Thr Thr Pro Ala Val Leu Asp Ser Asp Gly Ser
                405                 410                 415 tat ttc ctg tac tcc aag ctc tcc gtc ccc act tcg gaa tgg cag agg                   1296
Tyr Phe Leu Tyr Ser Lys Leu Ser Val Pro Thr Ser Glu Trp Gln Arg
            420                 425                 430 ggg gac gtg ttc act tgc tcc gtg atg cac gag gca ctc cac aac cac                   1344
Gly Asp Val Phe Thr Cys Ser Val Met His Glu Ala Leu His Asn His
        435                 440                 445 tac acc caa aag agc att tcg cgg tca cct ggc aag taa                               1383
Tyr Thr Gln Lys Ser Ile Ser Arg Ser Pro Gly Lys
    450                 455                 460

<210> SEQ ID NO 26
<211> LENGTH: 460
<212> TYPE: PRT
<213> ORGANISM: Artificial Sequence
<220> FEATURE:
<223> OTHER INFORMATION: Synthetic Construct

<400> SEQUENCE: 26

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Val Ser Gly Phe Ser Leu Ser
        35                  40                  45

Ser Tyr Gly Val Ser Trp Val Arg Gln Ala Pro Gly Asn Gly Leu Glu
    50                  55                  60

Trp Ile Gly Phe Ile Asp Lys Tyr Gly Arg Thr His Tyr Ala Ser Trp
65                  70                  75                  80

Ala Lys Ser Arg Ser Thr Ile Thr Arg Asn Thr Asn Glu Asn Thr Val
                85                  90                  95

Thr Leu Lys Met Thr Ser Leu Thr Ala Ala Asp Thr Ala Thr Phe Leu
            100                 105                 110

Cys Ala Arg Asp Asp Tyr Arg Pro Ala Tyr Gly Phe Asp Ile Trp Gly
        115                 120                 125

Pro Gly Thr Leu Val Thr Val Ser Ser Gly Gln Pro Lys Ala Pro Ser
    130                 135                 140
```

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
            165                 170                 175

Thr Trp Asn Ser Gly Thr Leu Thr Asn Gly Val Arg Thr Phe Pro Ser
        180                 185                 190

Val Arg Gln Ser Ser Gly Leu Tyr Ser Leu Ser Ser Val Val Ser Val
    195                 200                 205

Thr Ser Ser Gln Pro Val Thr Cys Asn Val Ala His Pro Ala Thr
210                 215                 220

Asn Thr Lys Val Asp Lys Thr Val Ala Pro Ser Thr Cys Ser Lys Pro
225                 230                 235                 240

Thr Cys Pro Pro Pro Glu Leu Leu Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Pro Glu Val Gln Phe
    275                 280                 285

Thr Trp Tyr Ile Asn Asn Glu Gln Val Arg Thr Ala Arg Pro Pro Leu
290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Ala Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460

<210> SEQ ID NO 27
<211> LENGTH: 720
<212> TYPE: DNA
<213> ORGANISM: Artificial Sequence
<220> FEATURE:
<223> OTHER INFORMATION: clone encoding G7 monoclonal antibody light
      chain 1
<220> FEATURE:
<221> NAME/KEY: CDS
<222> LOCATION: (1)..(717)

<400> SEQUENCE: 27 atg gac acg agg gcc ccc act cag ctg ctg ggg ctc ctg ctc ctc tgg    48
Met Asp Thr Arg Ala Pro Thr Gln Leu Leu Gly Leu Leu Leu Leu Trp
1               5                   10                  15

```
ctc cca ggt gcc aca ttt gcc caa gtg ctg acc cag act gca tcg ccc        96
Leu Pro Gly Ala Thr Phe Ala Gln Val Leu Thr Gln Thr Ala Ser Pro
        20                  25                  30 gtg tct gca gct gtg gga agc aca gtc acc atc aat tgc cag gcc agt       144
Val Ser Ala Ala Val Gly Ser Thr Val Thr Ile Asn Cys Gln Ala Ser
        35                  40                  45 cag agt gtt tat aat aac aac tgg tta tcc tgg ttt cag cag aaa cca       192
Gln Ser Val Tyr Asn Asn Asn Trp Leu Ser Trp Phe Gln Gln Lys Pro
    50                  55                  60 ggg cag cct ccc aag caa ctg ata tat ggt gca tcc act ctg cca tct       240
Gly Gln Pro Pro Lys Gln Leu Ile Tyr Gly Ala Ser Thr Leu Pro Ser
65                  70                  75                  80 ggg gtc tca tcg cgg ttc aaa ggc agt gga tct ggg aca cag ttc act       288
Gly Val Ser Ser Arg Phe Lys Gly Ser Gly Ser Gly Thr Gln Phe Thr
            85                  90                  95 ctc acc atc agc gac gtg cag tgt gac gat gct gcc act tac tac tgt       336
Leu Thr Ile Ser Asp Val Gln Cys Asp Asp Ala Ala Thr Tyr Tyr Cys
        100                 105                 110 ctg ggc ggt tat cat tgg agt act gct gat tgt aat gtt ttc ggc gga       384
Leu Gly Gly Tyr His Trp Ser Thr Ala Asp Cys Asn Val Phe Gly Gly
        115                 120                 125 ggg acc gag gtg gtg gtc aaa ggt gat cca gtt gca cct act gtc ctc       432
Gly Thr Glu Val Val Val Lys Gly Asp Pro Val Ala Pro Thr Val Leu
    130                 135                 140 atc ttc cca cca gct gct gat cag gtg gca act gga aca gtc acc atc       480
Ile Phe Pro Pro Ala Ala Asp Gln Val Ala Thr Gly Thr Val Thr Ile
145                 150                 155                 160 gtg tgc gtg gct aac aag tac ttc ccg gac gtg acc gtg acc tgg gaa       528
Val Cys Val Ala Asn Lys Tyr Phe Pro Asp Val Thr Val Thr Trp Glu
            165                 170                 175 gtc gac gga acc act cag acc act ggt atc gag aac agc aag acg ccc       576
Val Asp Gly Thr Thr Gln Thr Thr Gly Ile Glu Asn Ser Lys Thr Pro
        180                 185                 190 cag aac tcc gcc gat tgt act tat aac ctg tcc tcc aca ctg acc ctc       624
Gln Asn Ser Ala Asp Cys Thr Tyr Asn Leu Ser Ser Thr Leu Thr Leu
        195                 200                 205 acc tcg acc cag tac aat tcc cac aag gag tac act tgc aaa gtc acc       672
Thr Ser Thr Gln Tyr Asn Ser His Lys Glu Tyr Thr Cys Lys Val Thr
    210                 215                 220 cag gga acc act tca gtg gtg cag agc ttc aac cgg ggg gat tgc tga       720
Gln Gly Thr Thr Ser Val Val Gln Ser Phe Asn Arg Gly Asp Cys
225                 230                 235

<210> SEQ ID NO 28
<211> LENGTH: 239
<212> TYPE: PRT
<213> ORGANISM: Artificial Sequence
<220> FEATURE:
<223> OTHER INFORMATION: Synthetic Construct

<400> SEQUENCE: 28

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Ser Thr Val Thr Ile Asn Cys Gln Ala Ser
        35                  40                  45

Gln Ser Val Tyr Asn Asn Asn Trp Leu Ser Trp Phe Gln Gln Lys Pro
    50                  55                  60

Gly Gln Pro Pro Lys Gln Leu Ile Tyr Gly Ala Ser Thr Leu Pro Ser
```

```
                65                  70                  75                  80
Gly Val Ser Ser Arg Phe Lys Gly Ser Gly Ser Gly Thr Gln Phe Thr
                    85                  90                  95

Leu Thr Ile Ser Asp Val Gln Cys Asp Asp Ala Ala Thr Tyr Tyr Cys
                100                 105                 110

Leu Gly Gly Tyr His Trp Ser Thr Ala Asp Cys Asn Val Phe Gly Gly
            115                 120                 125

Gly Thr Glu Val Val Lys Gly Asp Pro Val Ala Pro Thr Val Leu
        130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
                195                 200                 205

Thr Ser Thr Gln Tyr Asn Ser His Lys Glu Tyr Thr Cys Lys Val Thr
        210                 215                 220

Gln Gly Thr Thr Ser Val Val Gln Ser Phe Asn Arg Gly Asp Cys
225                 230                 235
```

```
<210> SEQ ID NO 29
<211> LENGTH: 9
<212> TYPE: PRT
<213> ORGANISM: Artificial Sequence
<220> FEATURE:
<223> OTHER INFORMATION: CDR-H1 of A2 monoclonal antibody

<400> SEQUENCE: 29

Phe Thr Val Ser Ser Tyr Asp Met Gly
1               5

<210> SEQ ID NO 30
<211> LENGTH: 17
<212> TYPE: PRT
<213> ORGANISM: Artificial Sequence
<220> FEATURE:
<223> OTHER INFORMATION: CDR-H2 of A2 monoclonal antibody

<400> SEQUENCE: 30

Ser Ile Gly Ala Ile Gly Ser Asp Gly Ser Glu Tyr Tyr Val Ser Trp
1               5                   10                  15

Ala

<210> SEQ ID NO 31
<211> LENGTH: 14
<212> TYPE: PRT
<213> ORGANISM: Artificial Sequence
<220> FEATURE:
<223> OTHER INFORMATION: CDR-H3 of A2 monoclonal antibody

<400> SEQUENCE: 31

Ala Arg Asp Ser His Tyr Ser Tyr Gly Tyr Asp Tyr Asp Ile
1               5                   10

<210> SEQ ID NO 32
<211> LENGTH: 9
<212> TYPE: PRT
<213> ORGANISM: Artificial Sequence
<220> FEATURE:
```

```
<223> OTHER INFORMATION: CDR-L1 of A2 monoclonal antibody

<400> SEQUENCE: 32

Gln Ser Ile Tyr Ser Asn Tyr Leu Ser
1               5

<210> SEQ ID NO 33
<211> LENGTH: 11
<212> TYPE: PRT
<213> ORGANISM: Artificial Sequence
<220> FEATURE:
<223> OTHER INFORMATION: CDR-L2 of A2 monoclonal antibody

<400> SEQUENCE: 33

Leu Leu Ile Tyr Tyr Ala Ser Thr Leu Ala Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: CDR-L3 of A2 monoclonal antibody

<400> SEQUENCE: 34

Gln Gly Thr Tyr Tyr Val Thr Gly Trp Tyr Asp Ala
1               5                   10

<210> SEQ ID NO 35
<211> LENGTH: 9
<212> TYPE: PRT
<213> ORGANISM: Artificial Sequence
<220> FEATURE:
<223> OTHER INFORMATION: CDR-H1 of E5 monoclonal antibody

<400> SEQUENCE: 35

Phe Ser Leu Ser Ser Tyr Asp Met Ser
1               5

<210> SEQ ID NO 36
<211> LENGTH: 17
<212> TYPE: PRT
<213> ORGANISM: Artificial Sequence
<220> FEATURE:
<223> OTHER INFORMATION: CDR-H2 of E5 monoclonal antibody

<400> SEQUENCE: 36

Trp Ile Gly Tyr Leu Ser Ser Asp Gly Arg Ala Tyr Tyr Ala Ser Trp
1               5                   10                  15

Ala

<210> SEQ ID NO 37
<211> LENGTH: 9
<212> TYPE: PRT
<213> ORGANISM: Artificial Sequence
<220> FEATURE:
<223> OTHER INFORMATION: CDR-H3 of E5 monoclonal antibody

<400> SEQUENCE: 37

Ala Arg Gly Asp Asn Thr Ala Asp Ile
1               5

<210> SEQ ID NO 38
<211> LENGTH: 10
<212> TYPE: PRT
<213> ORGANISM: Artificial Sequence
```

```
<220> FEATURE:
<223> OTHER INFORMATION: CDR-L1 of E5 monoclonal antibody

<400> SEQUENCE: 38

Gln Ser Val Tyr Lys Asn Asn Asp Leu Ala
1               5                   10

<210> SEQ ID NO 39
<211> LENGTH: 11
<212> TYPE: PRT
<213> ORGANISM: Artificial Sequence
<220> FEATURE:
<223> OTHER INFORMATION: CDR-L2 of E5 monoclonal antibody

<400> SEQUENCE: 39

Leu Leu Ile Tyr Phe Ala Ser Thr Leu Ala Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: CDR-L3 of E5 monoclonal antibody

<400> SEQUENCE: 40

Ala Gly Gly Tyr Ser Gly Pro Val Gly Ala
1               5                   10

<210> SEQ ID NO 41
<211> LENGTH: 9
<212> TYPE: PRT
<213> ORGANISM: Artificial Sequence
<220> FEATURE:
<223> OTHER INFORMATION: CDR-H1 of G7 monoclonal antibody

<400> SEQUENCE: 41

Phe Ser Leu Ser Ser Tyr Gly Val Ser
1               5

<210> SEQ ID NO 42
<211> LENGTH: 17
<212> TYPE: PRT
<213> ORGANISM: Artificial Sequence
<220> FEATURE:
<223> OTHER INFORMATION: CDR-H2 of G7 monoclonal antibody

<400> SEQUENCE: 42

Trp Ile Gly Phe Ile Asp Lys Tyr Gly Arg Thr His Tyr Ala Ser Trp
1               5                   10                  15

Ala

<210> SEQ ID NO 43
<211> LENGTH: 13
<212> TYPE: PRT
<213> ORGANISM: Artificial Sequence
<220> FEATURE:
<223> OTHER INFORMATION: CDR-H3 of G7 monoclonal antibody

<400> SEQUENCE: 43

Ala Arg Asp Asp Tyr Arg Pro Ala Tyr Gly Phe Asp Ile
1               5                   10

<210> SEQ ID NO 44
<211> LENGTH: 10
<212> TYPE: PRT
```

```
<213> ORGANISM: Artificial Sequence
<220> FEATURE:
<223> OTHER INFORMATION: CDR-L1 of G7 monoclonal antibody

<400> SEQUENCE: 44

Gln Ser Val Tyr Asn Asn Asn Trp Leu Ser
1               5                   10

<210> SEQ ID NO 45
<211> LENGTH: 11
<212> TYPE: PRT
<213> ORGANISM: Artificial Sequence
<220> FEATURE:
<223> OTHER INFORMATION: CDR-L2 of G7 monoclonal antibody

<400> SEQUENCE: 45

Gln Leu Ile Tyr Gly Ala Ser Thr Leu Pro Ser
1               5                   10

<210> SEQ ID NO 46
<211> LENGTH: 13
<212> TYPE: PRT
<213> ORGANISM: Artificial Sequence
<220> FEATURE:
<223> OTHER INFORMATION: CDR-L3 of G7 monoclonal antibody

<400> SEQUENCE: 46

Leu Gly Gly Tyr His Trp Ser Thr Ala Asp Cys Asn Val
1               5                   10

<210> SEQ ID NO 47
<211> LENGTH: 8
<212> TYPE: PRT
<213> ORGANISM: Artificial Sequence
<220> FEATURE:
<223> OTHER INFORMATION: immunogenic peptide

<400> SEQUENCE: 47

Tyr Arg Leu Lys Arg Ser Lys Ser
1               5
```